United States Patent [19]

Narula et al.

[11] Patent Number: 5,128,317

[45] Date of Patent: Jul. 7, 1992

[54] CAMPHONYL SPIROCYCLOOXAOCTANE-CONTAINING COMPOSITIONS, ORGANOLEPTIC USES THEREOF AND PROCESS FOR PREPARING SAME

[75] Inventors: Anubhav P. S. Narula, Hazlet; John J. De Virgilio, Freehold, both of N.J.; Carlos Benaim, Bedford Hills, N.Y.; Anton Van Ouwerkerk, Livingston; Olivier Gillotin, Denville, both of N.J.

[73] Assignee: International Flavors and Fragrances Inc., New York, N.Y.

[21] Appl. No.: 736,283

[22] Filed: Jul. 25, 1991

Related U.S. Application Data

[63] Continuation-in-part of Ser. No. 588,825, Sep. 27, 1990, Pat. No. 5,081,262.

[51] Int. Cl.$^5$ .............................................. A61K 7/46
[52] U.S. Cl. ................................. 512/13; 549/396; 549/397; 549/463; 549/465; 568/420; 568/816
[58] Field of Search .................. 512/13; 549/396, 397, 549/463, 465; 568/420, 816

[56] References Cited

U.S. PATENT DOCUMENTS 4,267,067  5/1981  Sprecker et al. ................ 252/174.11
4,269,862  5/1981  Sprecker et al. ...................... 426/536

OTHER PUBLICATIONS

Arctander, "Perfume and Flavor Chemicals" (Aroma Chemicals), 1969 (Published by the Author) Monograph 616.

Primary Examiner—James H. Reamer
Attorney, Agent, or Firm—Arthur L. Liberman

[57] ABSTRACT

Described are camphonyl spirocyclooxaoctane-containing compositions having the generic structures:

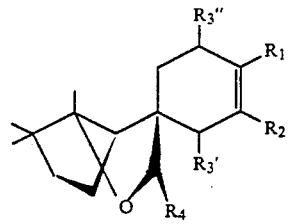

and

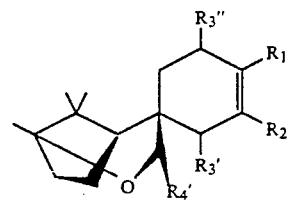

and mixtures of same with substituted cyclopentenyl-oxabicyclooctanes defined according to the generic structures:

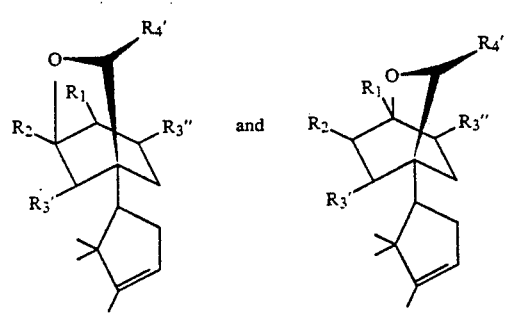

wherein $R_1$, $R_2$, $R_3'$ and $R_3''$ each represents hydrogen or methyl and $R_4'$ represents hydrogen or $C_1$-$C_5$ alkyl, processes for preparing same and uses thereof in augmenting or enhancing the aroma of perfume compositions, colognes and perfumed articles, e.g., solid or liquid anionic, cationic, nonionic or zwitterionic detergents, cosmetic preparations, fabric softener compositions, fabric softener articles, hair preparations and perfumed polymers.

15 Claims, 50 Drawing Sheets

GLC PROFILE FOR EXAMPLE I.

GLC PROFILE FOR EXAMPLE II.

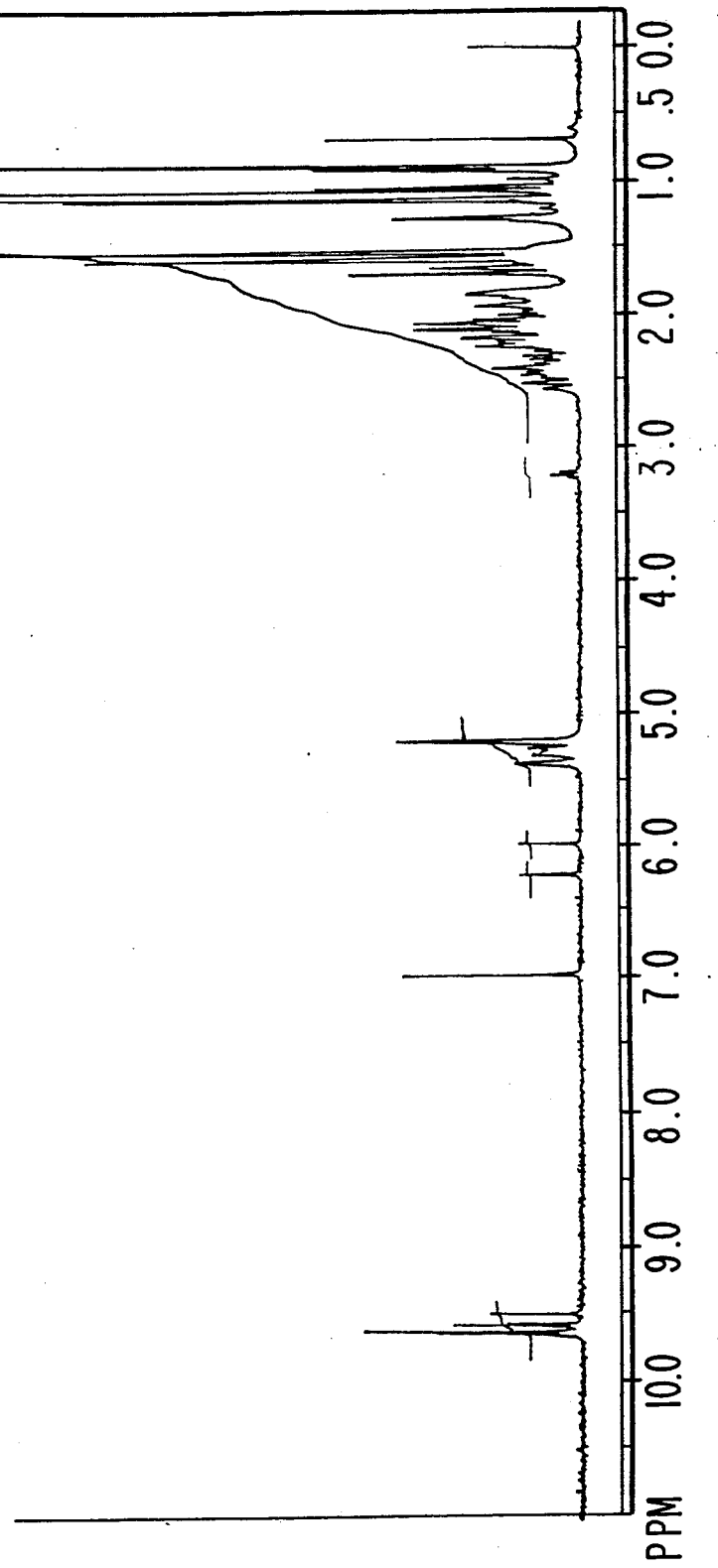

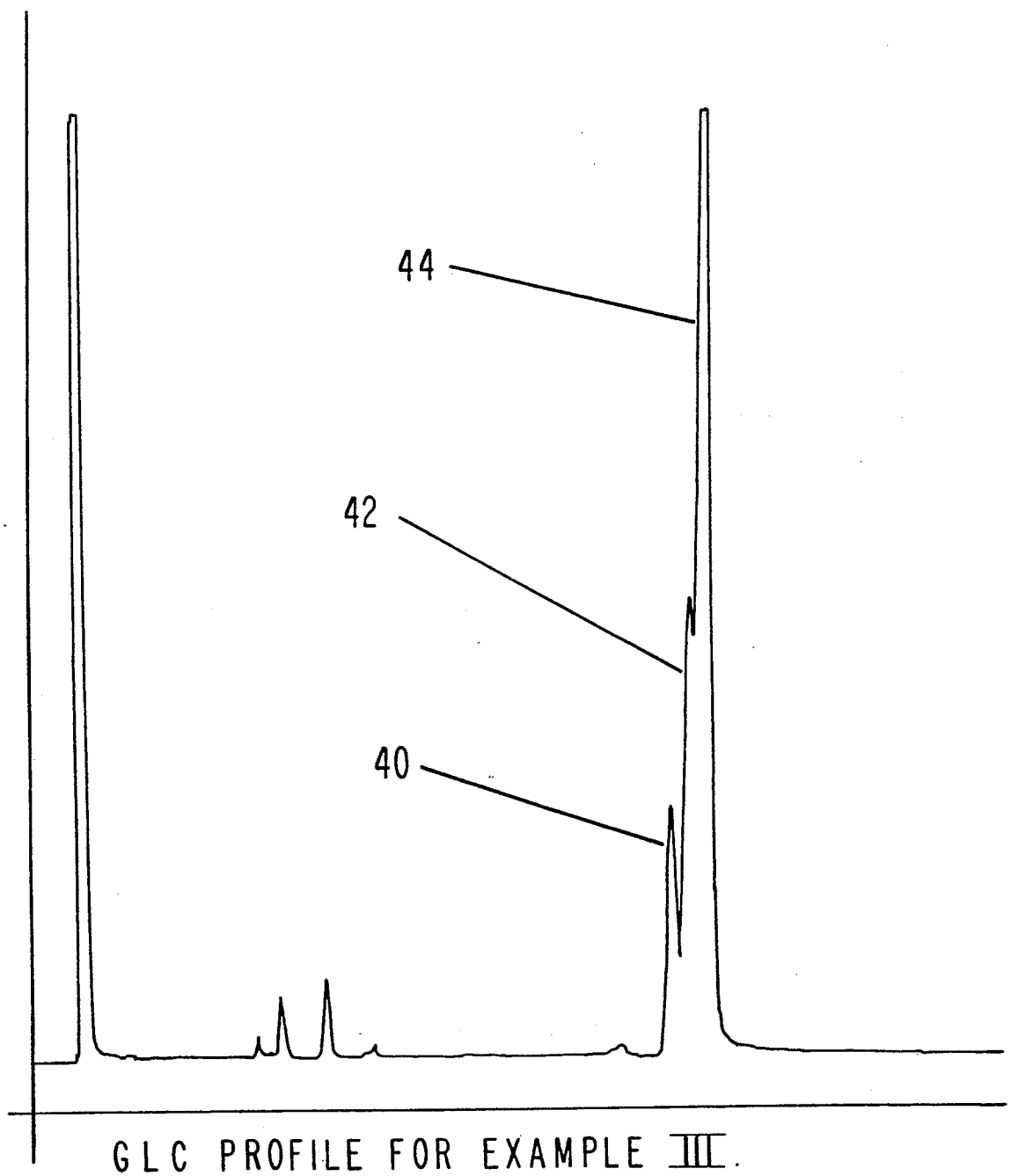

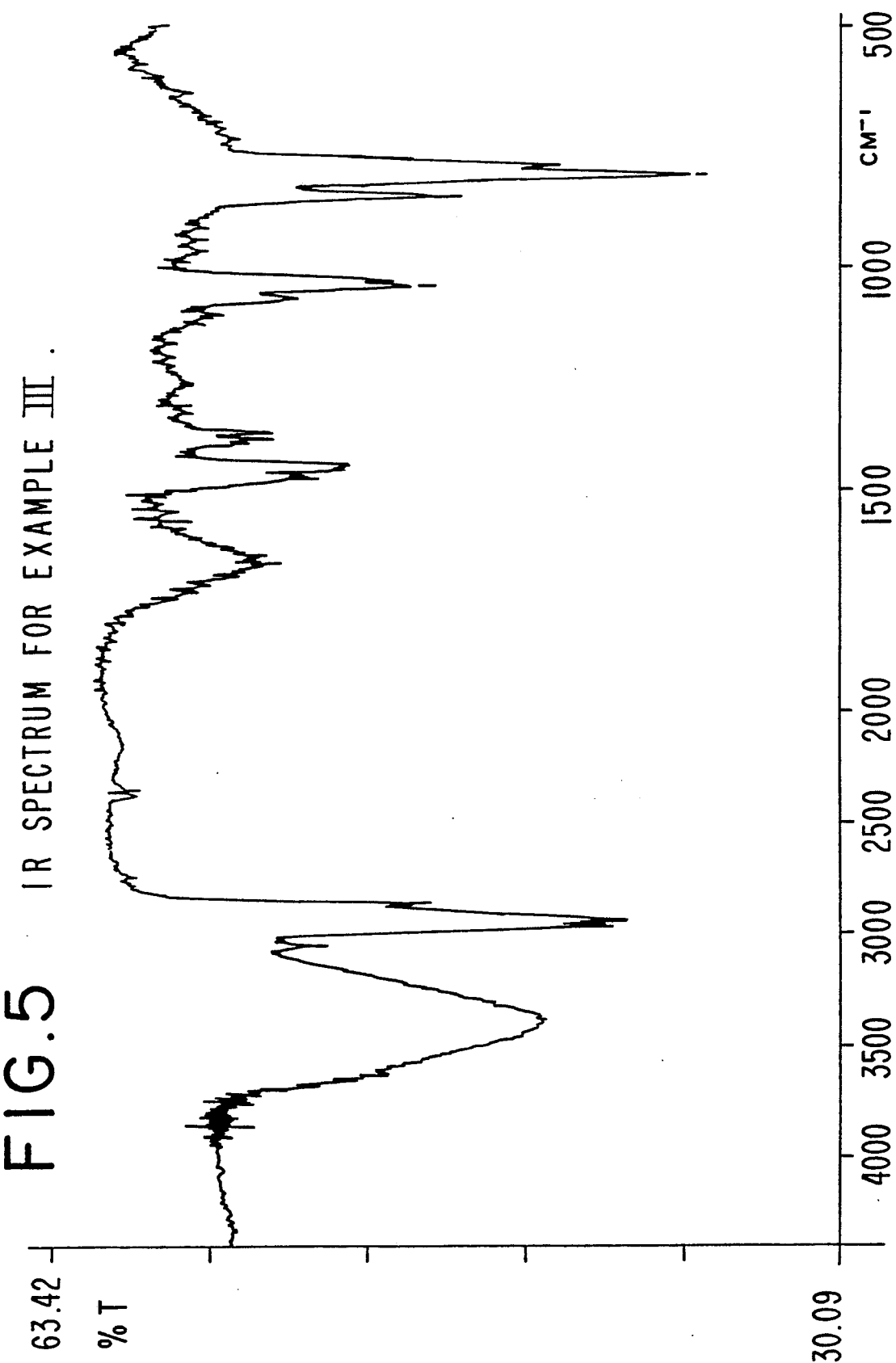
FIG.5  IR SPECTRUM FOR EXAMPLE III.

5.4 5.2
PPM 3.6 3.4
PPM

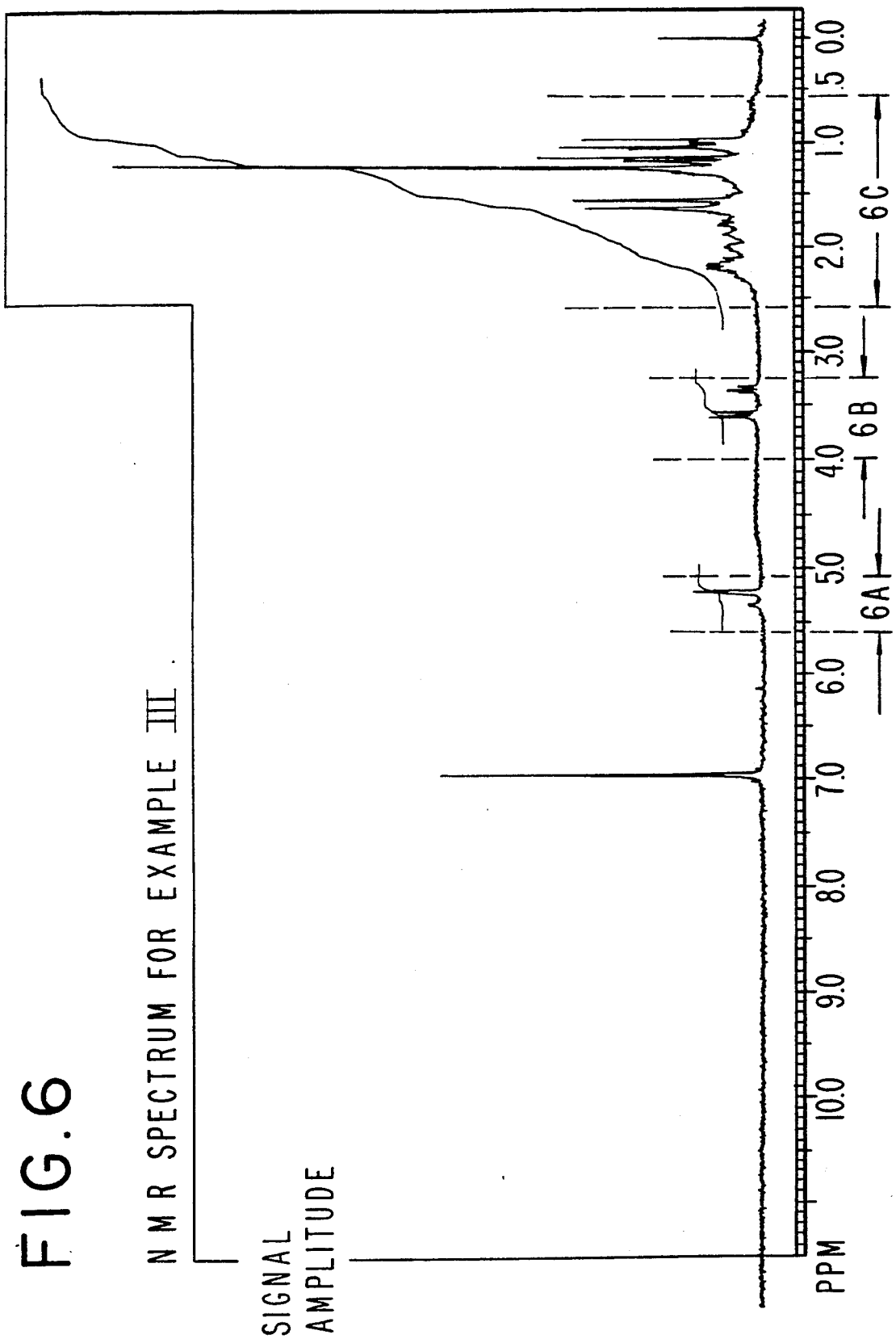

GLC PROFILE FOR EXAMPLE IV.

FIG. 8 IR SPECTRUM FOR EXAMPLE IV.

FIG. 9 NMR SPECTRUM FOR EXAMPLE IV.

GLC PROFILE FOR EXAMPLE V.

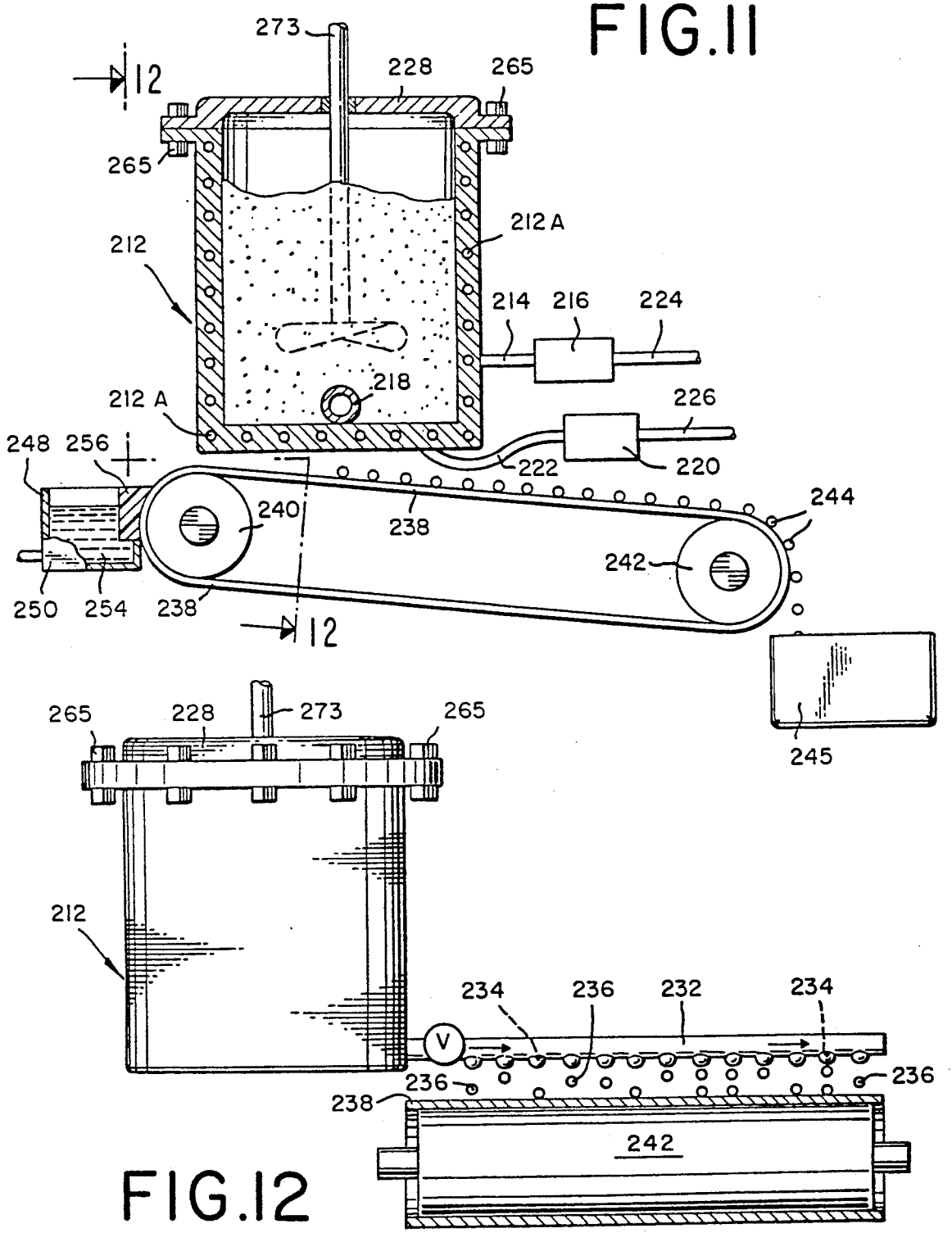

GLC PROFILE FOR EXAMPLE VII.

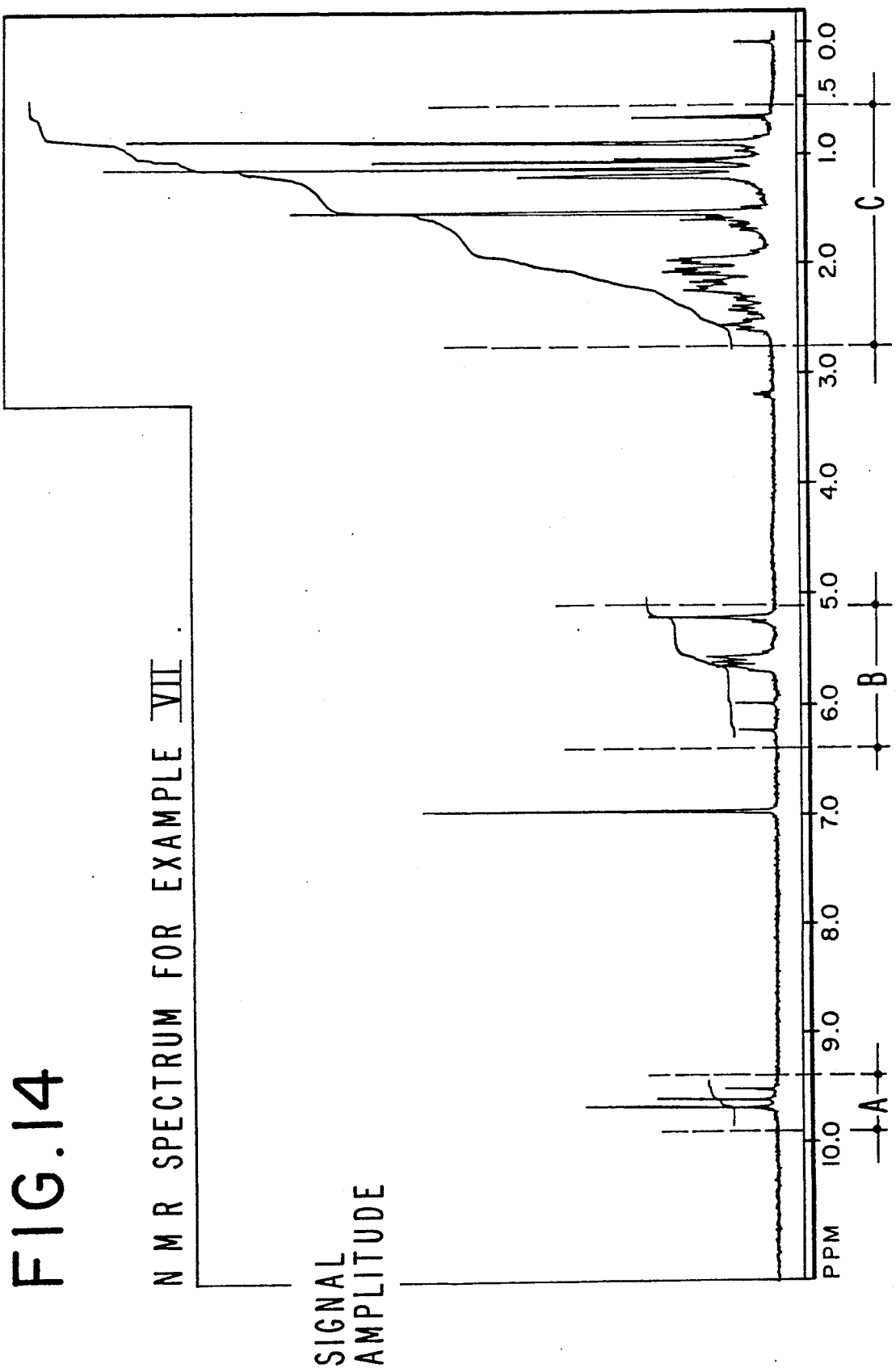

FIG.14-A 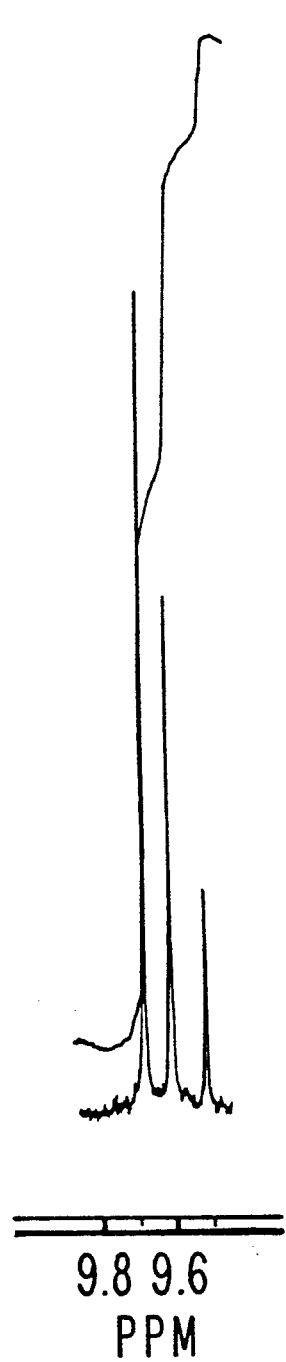
FIG.14-B 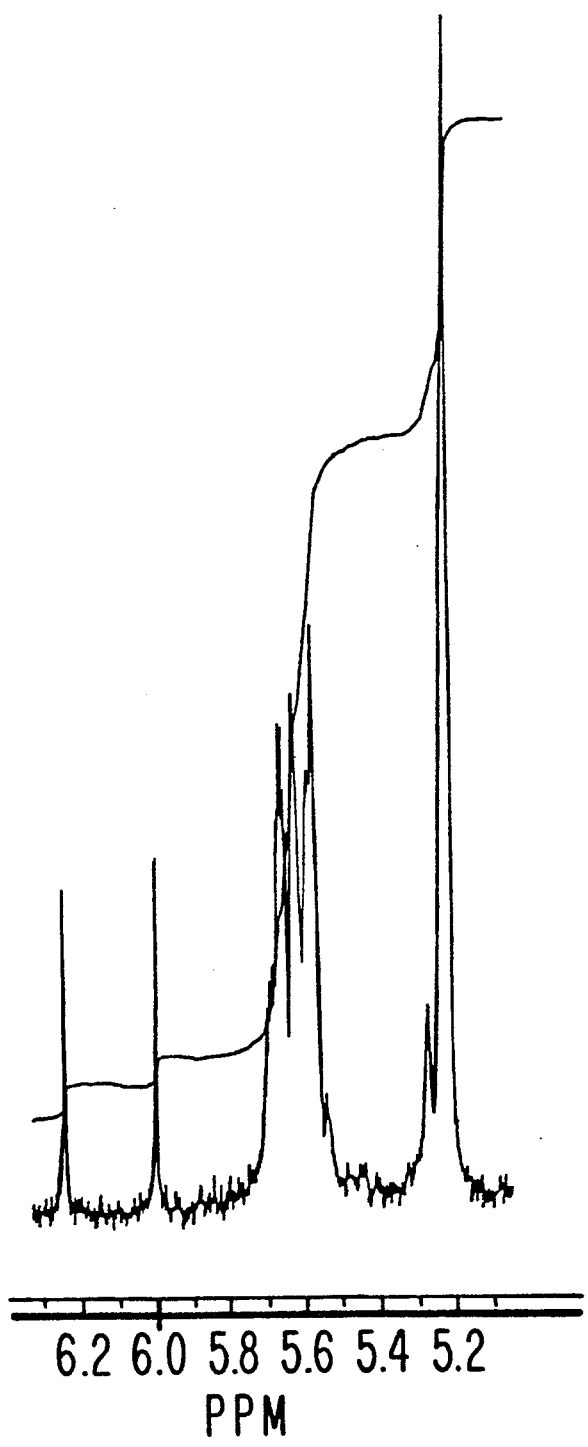

FIG.14-C
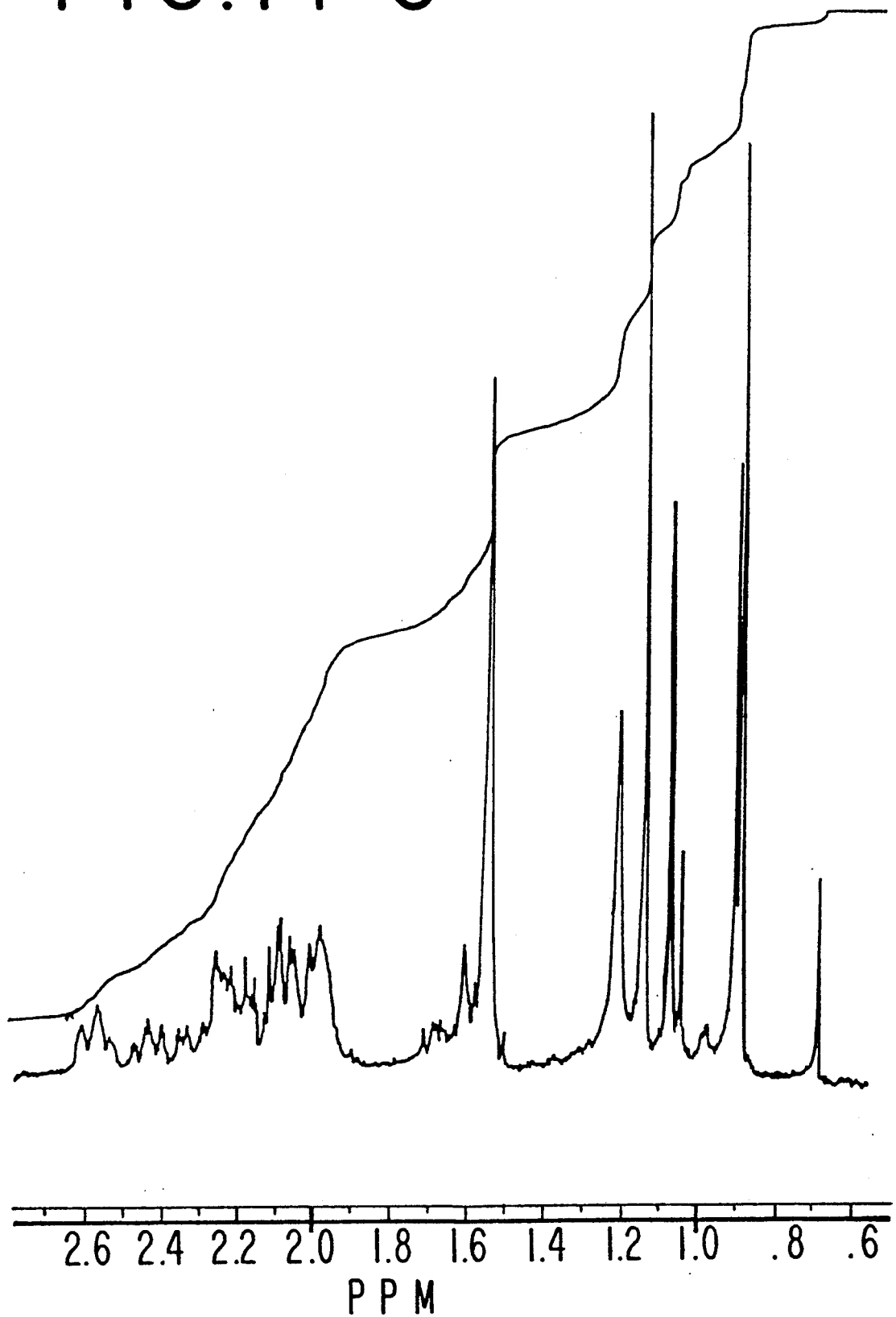

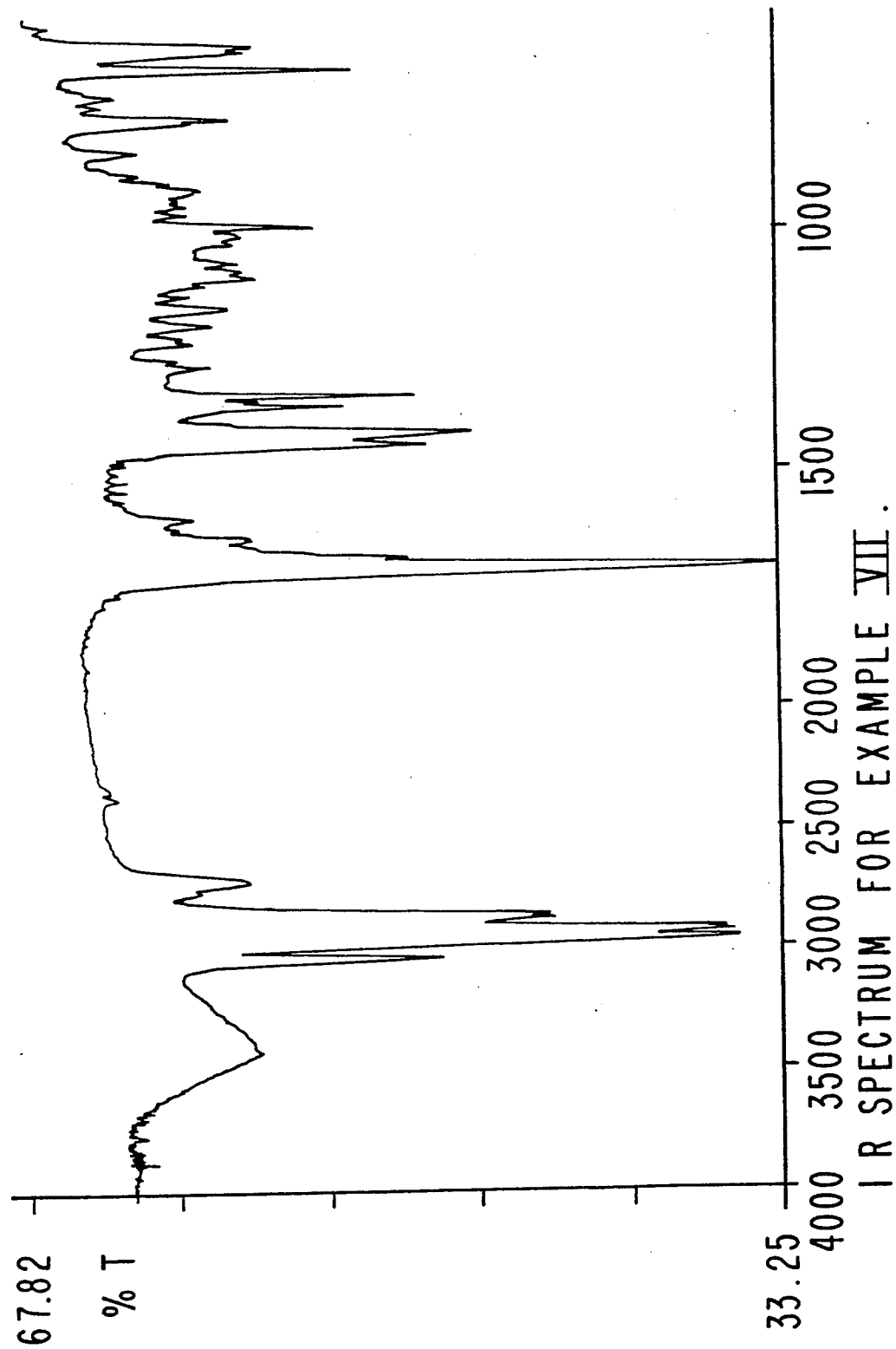

GLC PROFILE FOR EXAMPLE VIII.

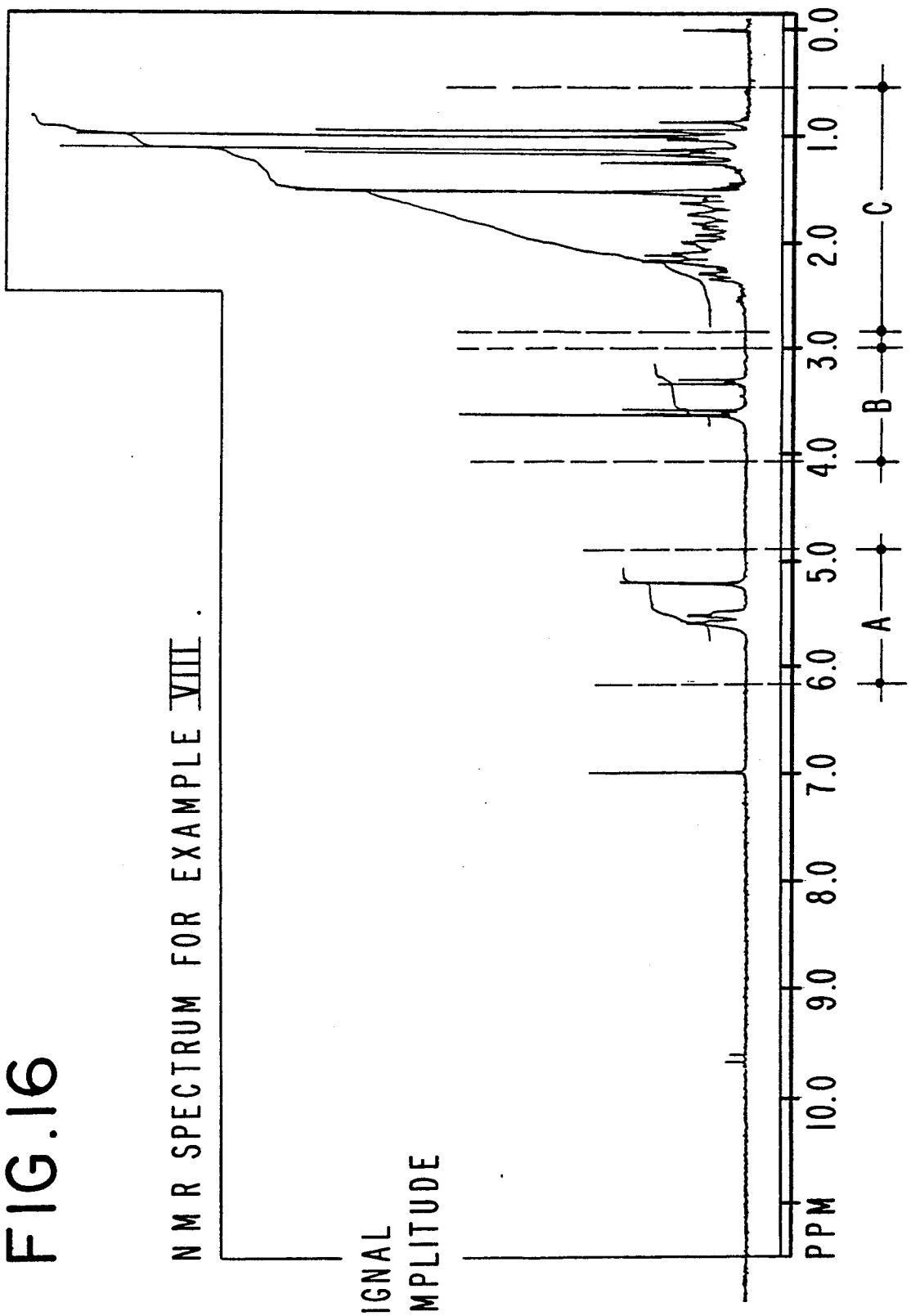
FIG. 16 NMR SPECTRUM FOR EXAMPLE VIII.

FIG.16-A
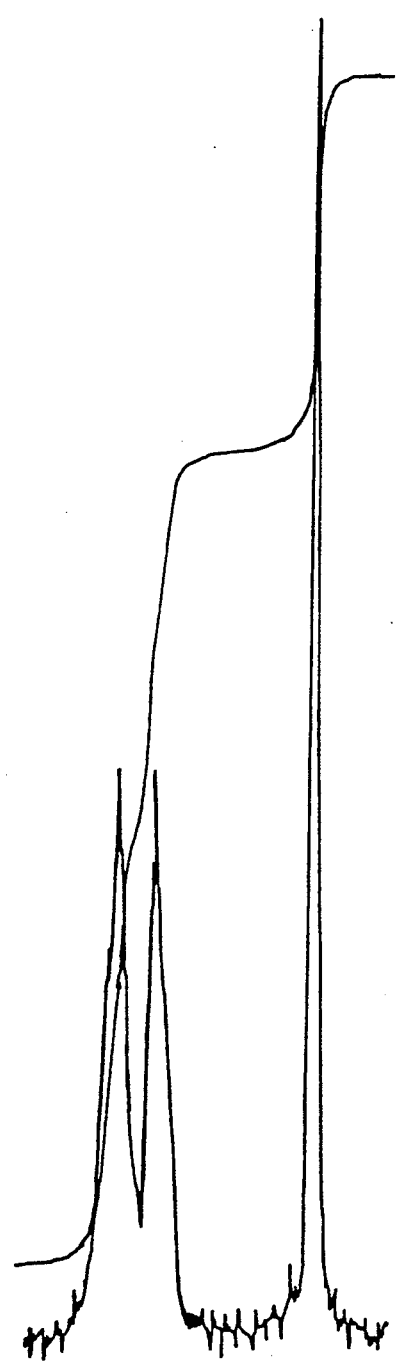
5.6  5.4  5.2
P P M
FIG.16-B
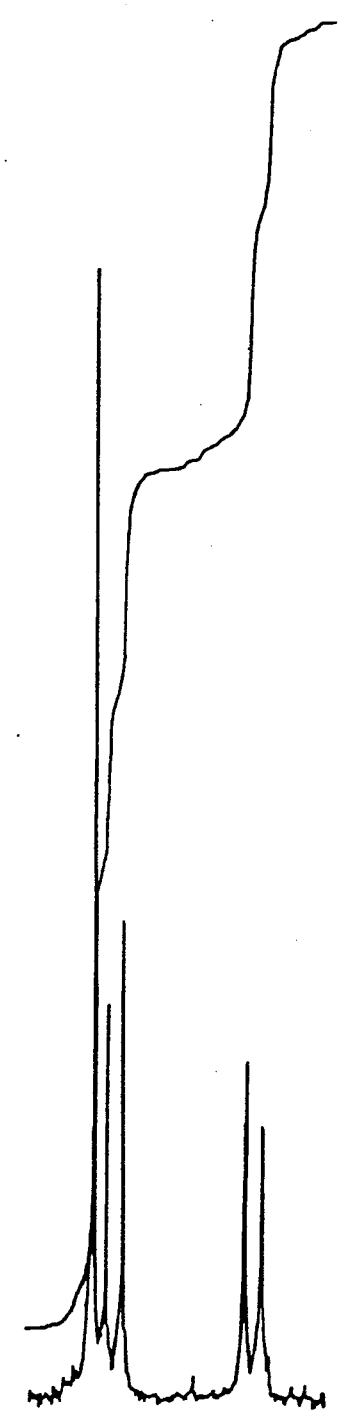
3.6  3.4
P P M

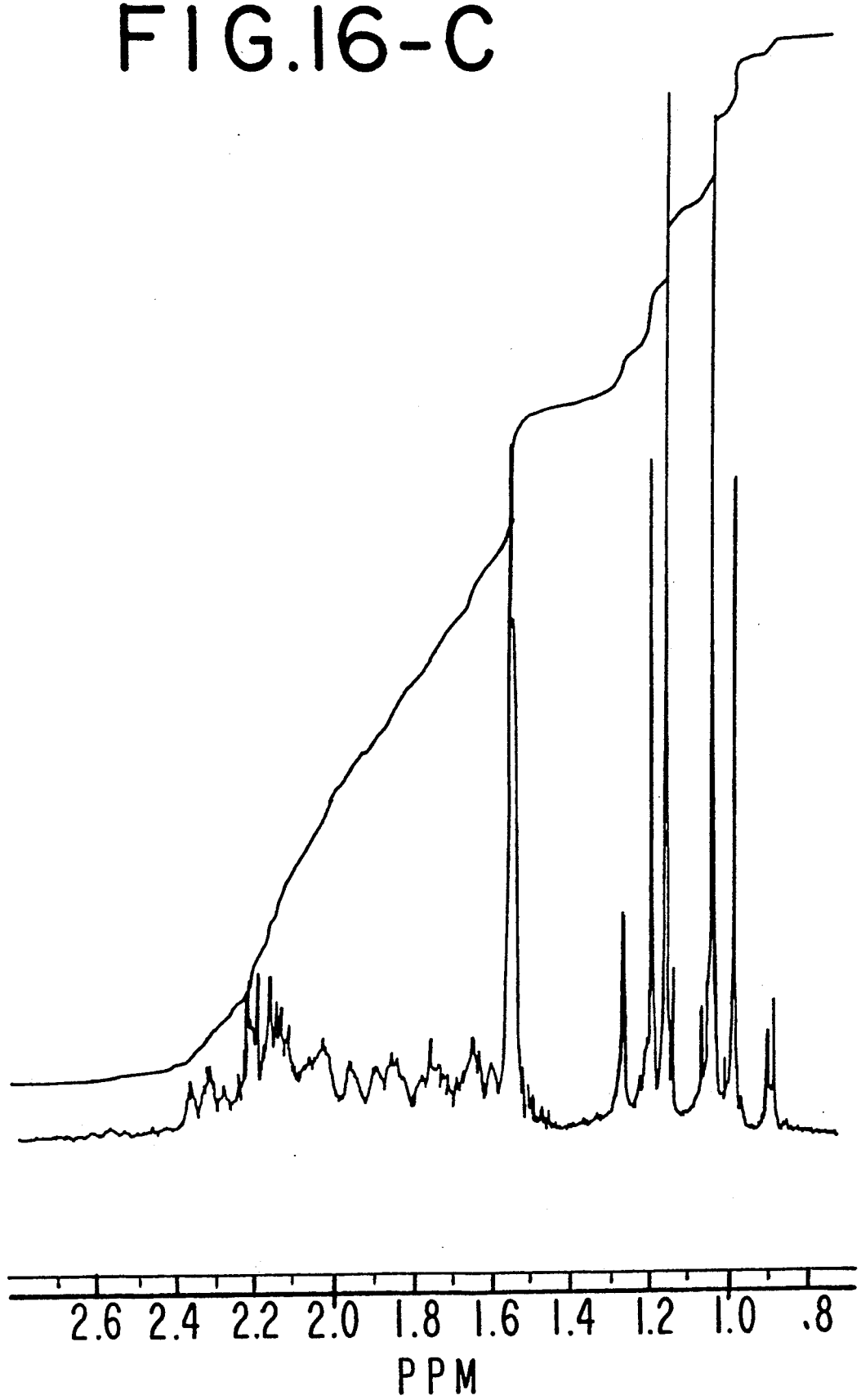
FIG.16-C

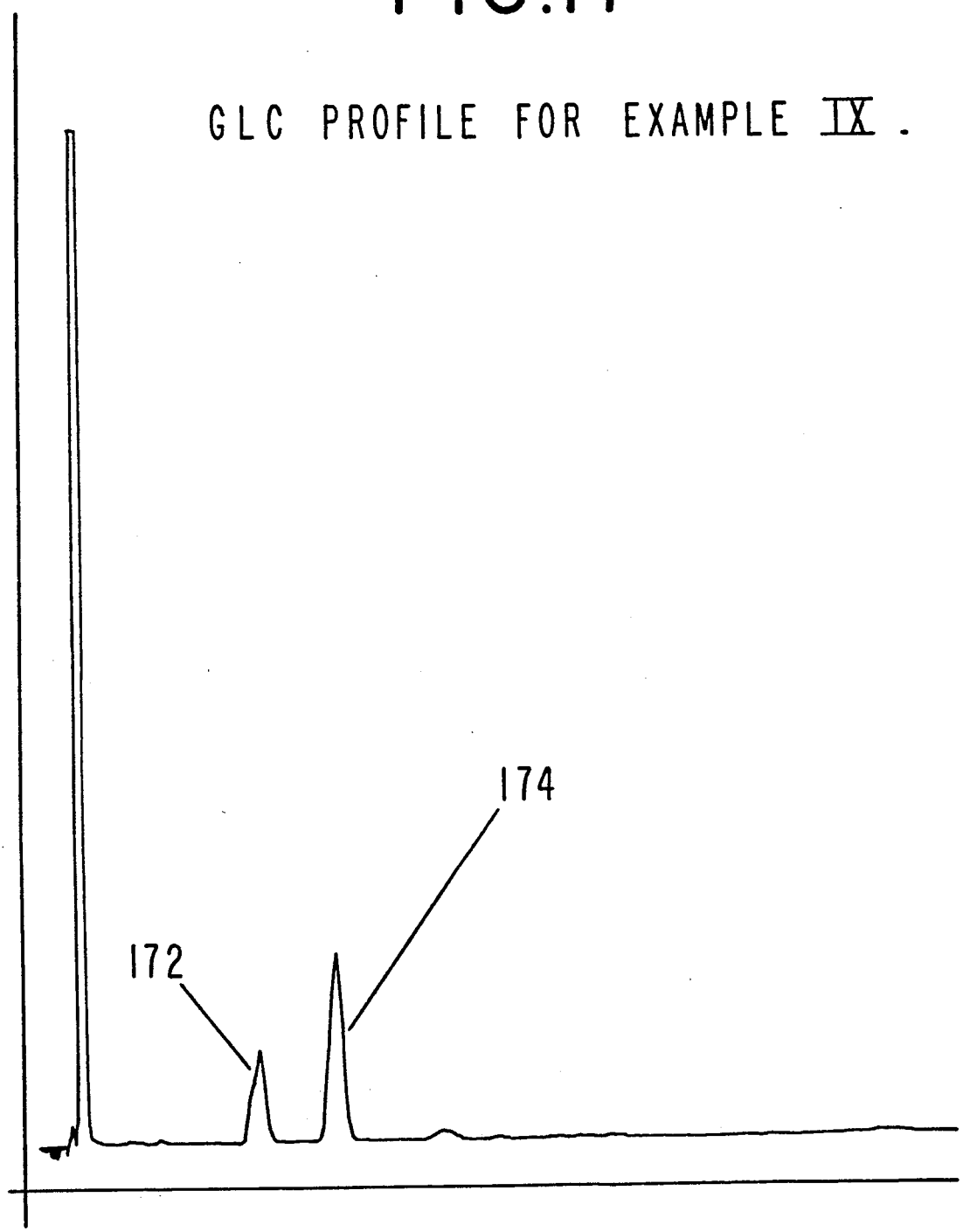

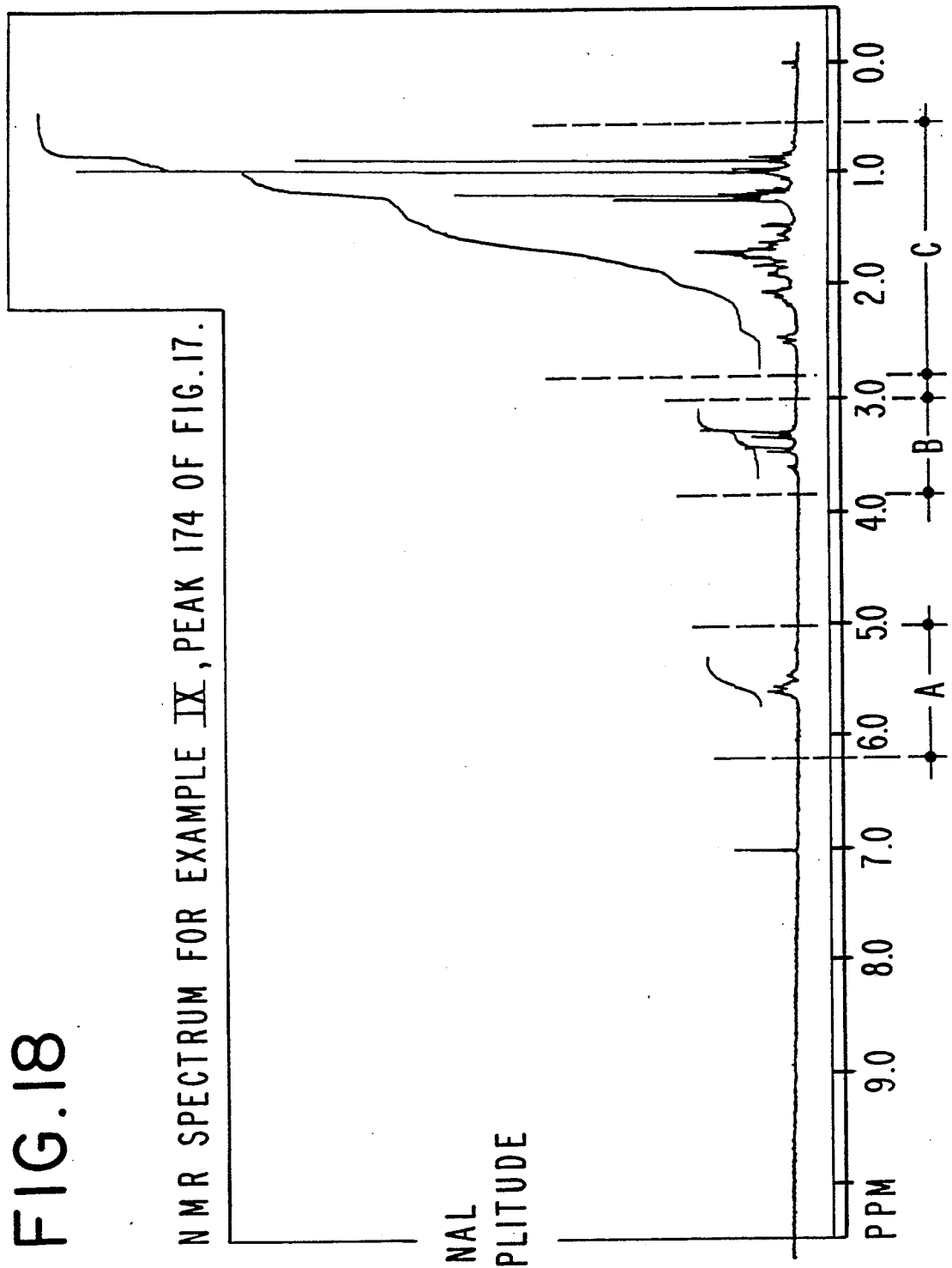
FIG. 18 NMR SPECTRUM FOR EXAMPLE IX, PEAK 174 OF FIG. 17.

FIG.18-A
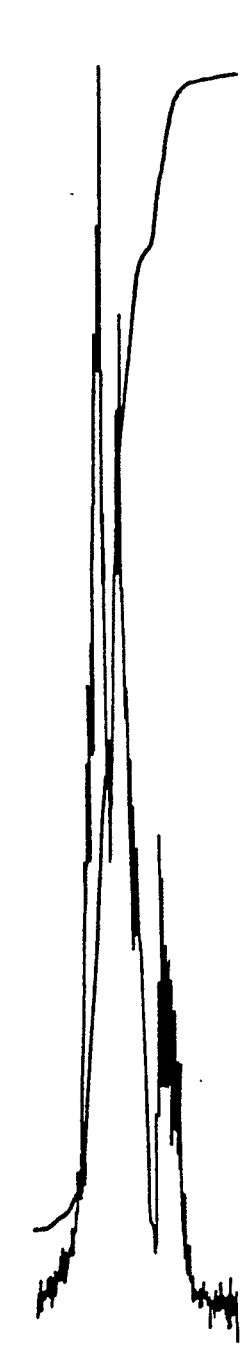
5.6  5.4
FIG.18-B
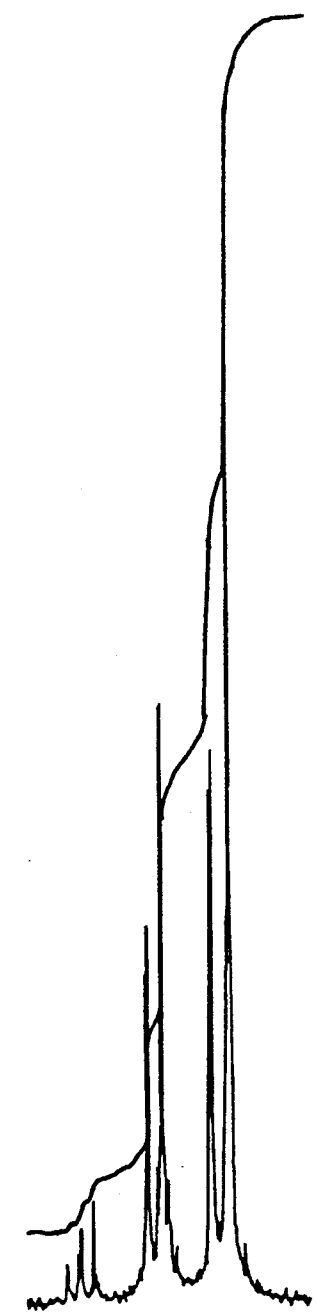
3.6  3.4  3.2

FIG. 18-C
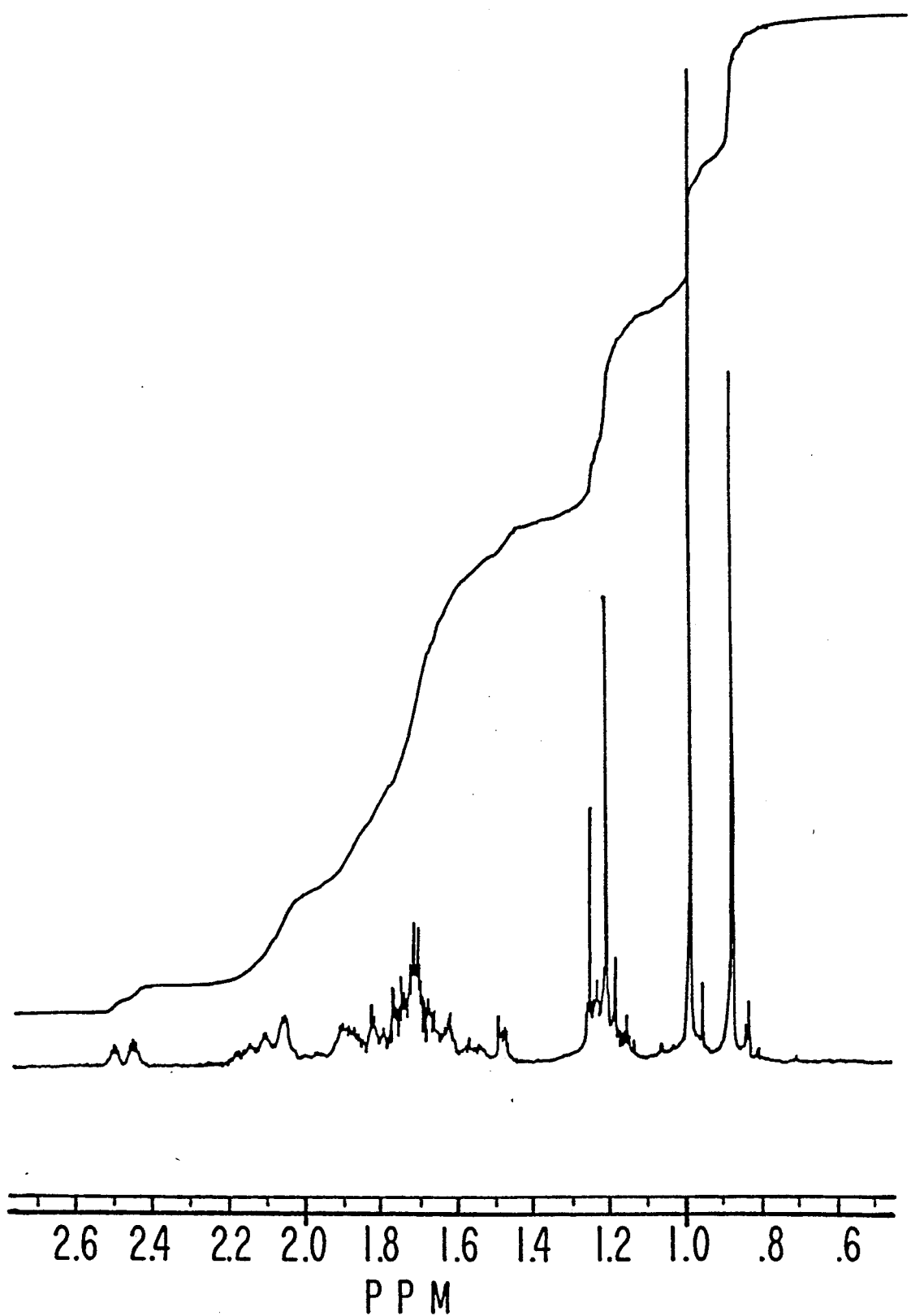

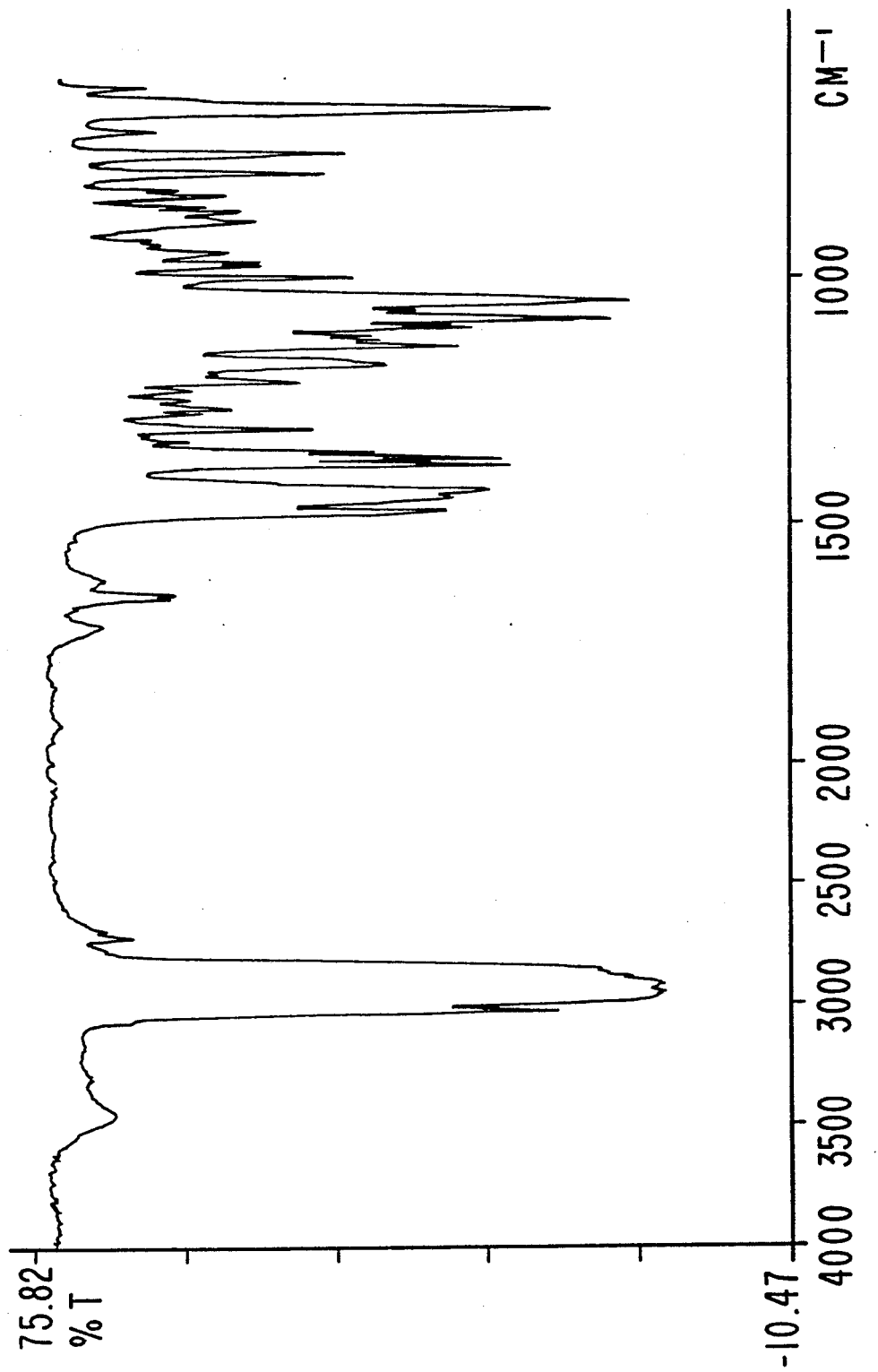

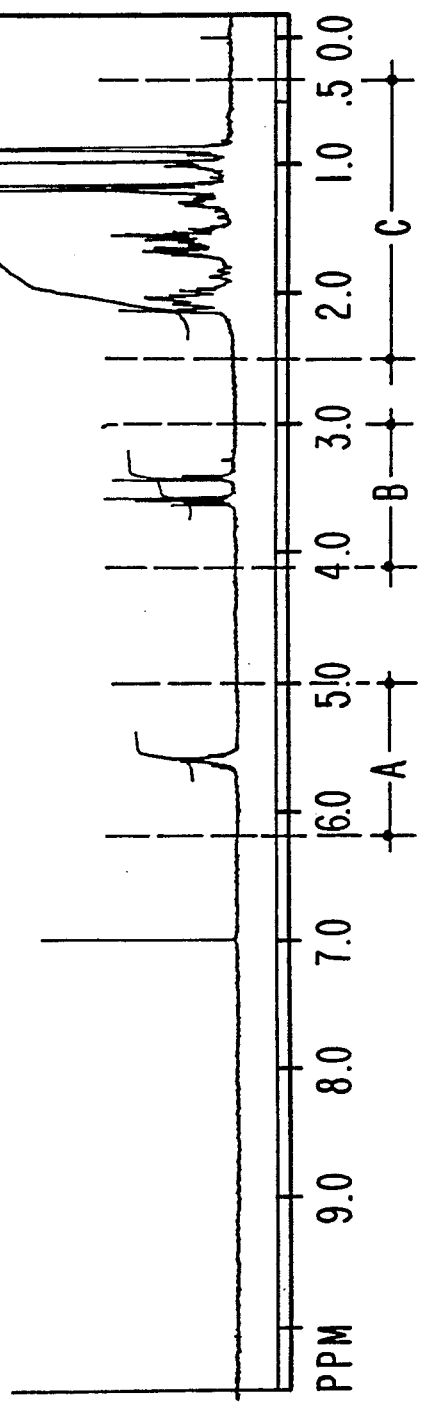

FIG.20-A
FIG.20-B
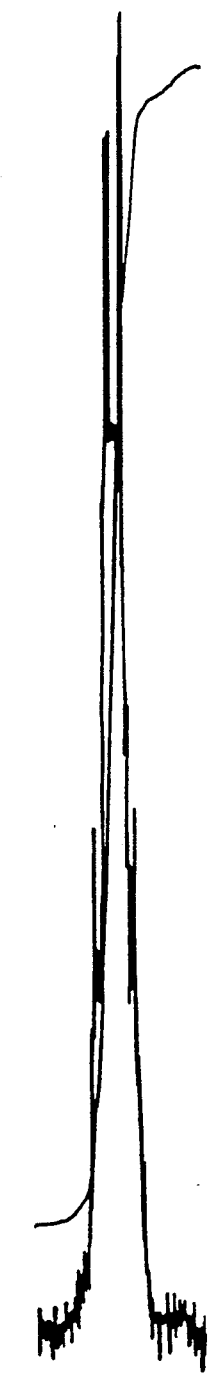
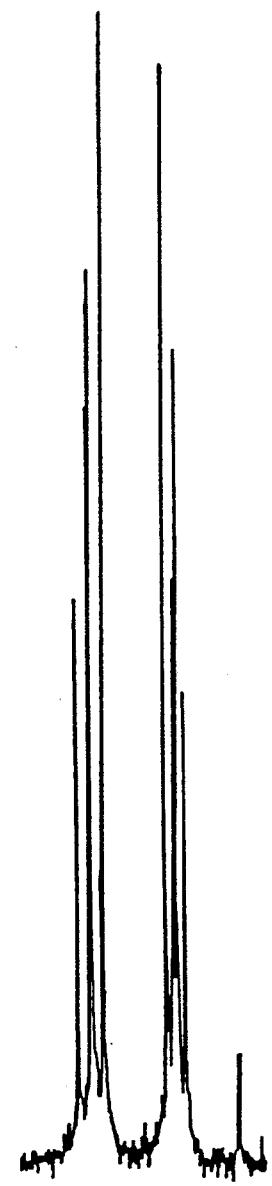
5.6
PPM
3.6  3.4
PPM

FIG. 20-C
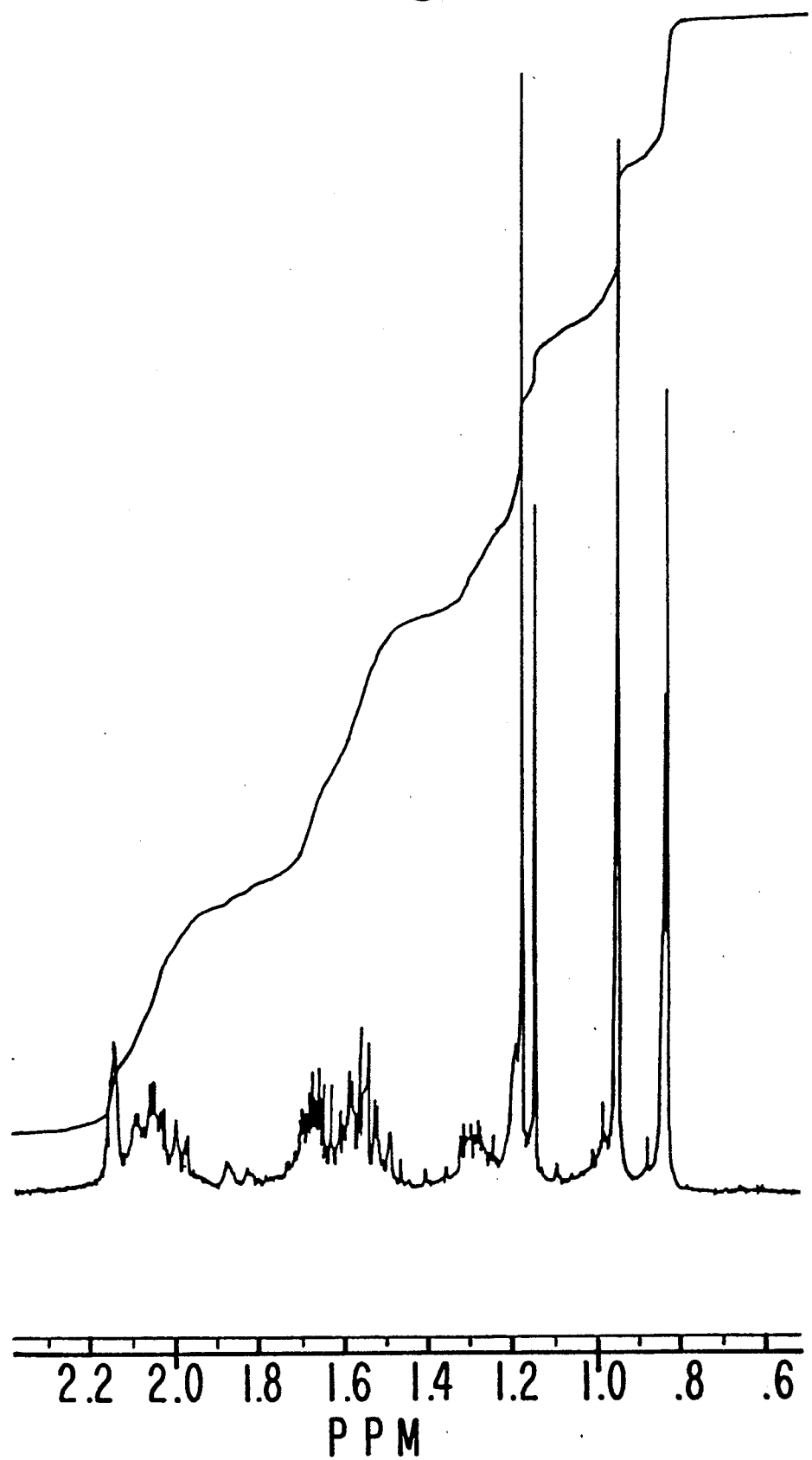

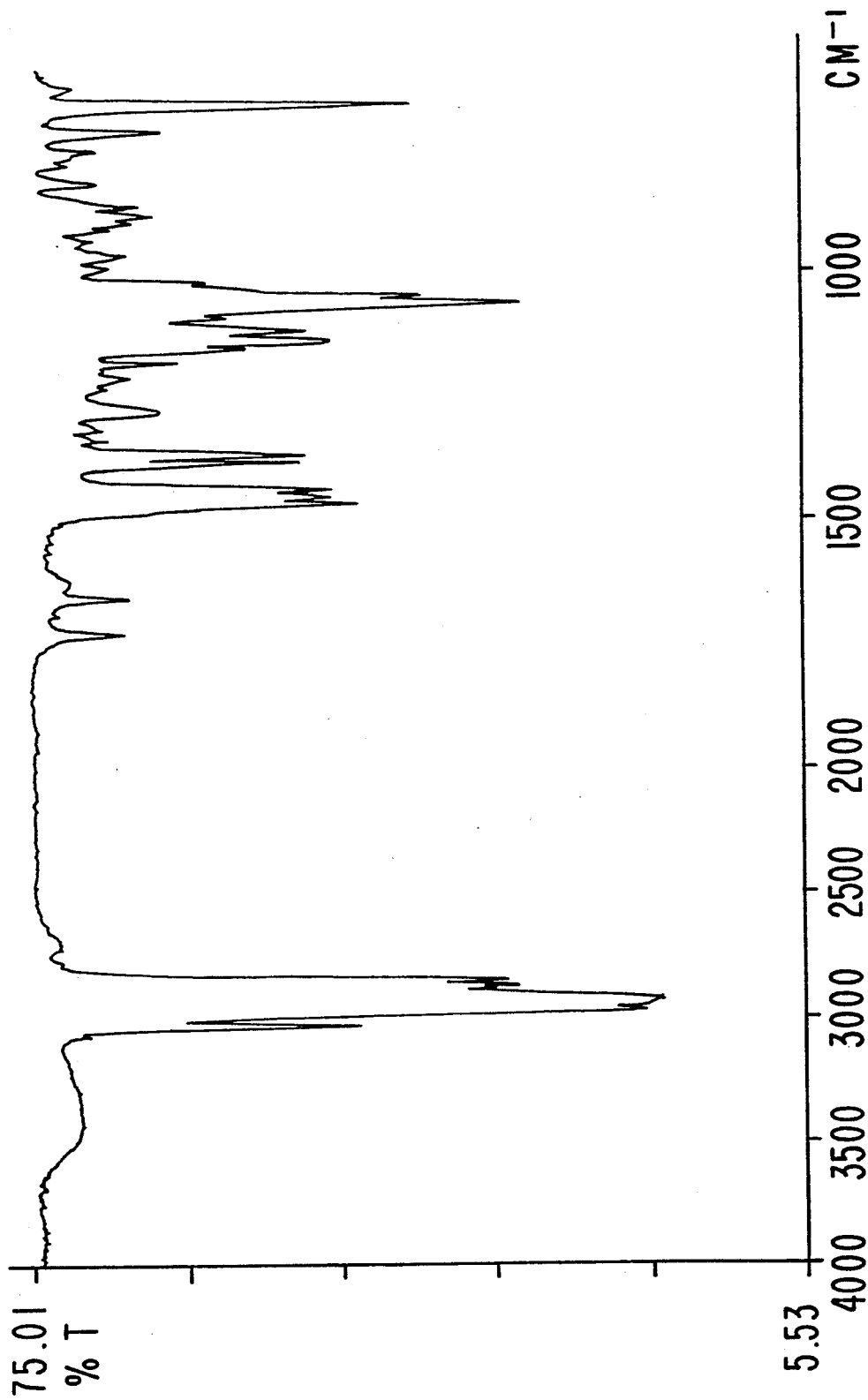

GLC PROFILE FOR EXAMPLE X.

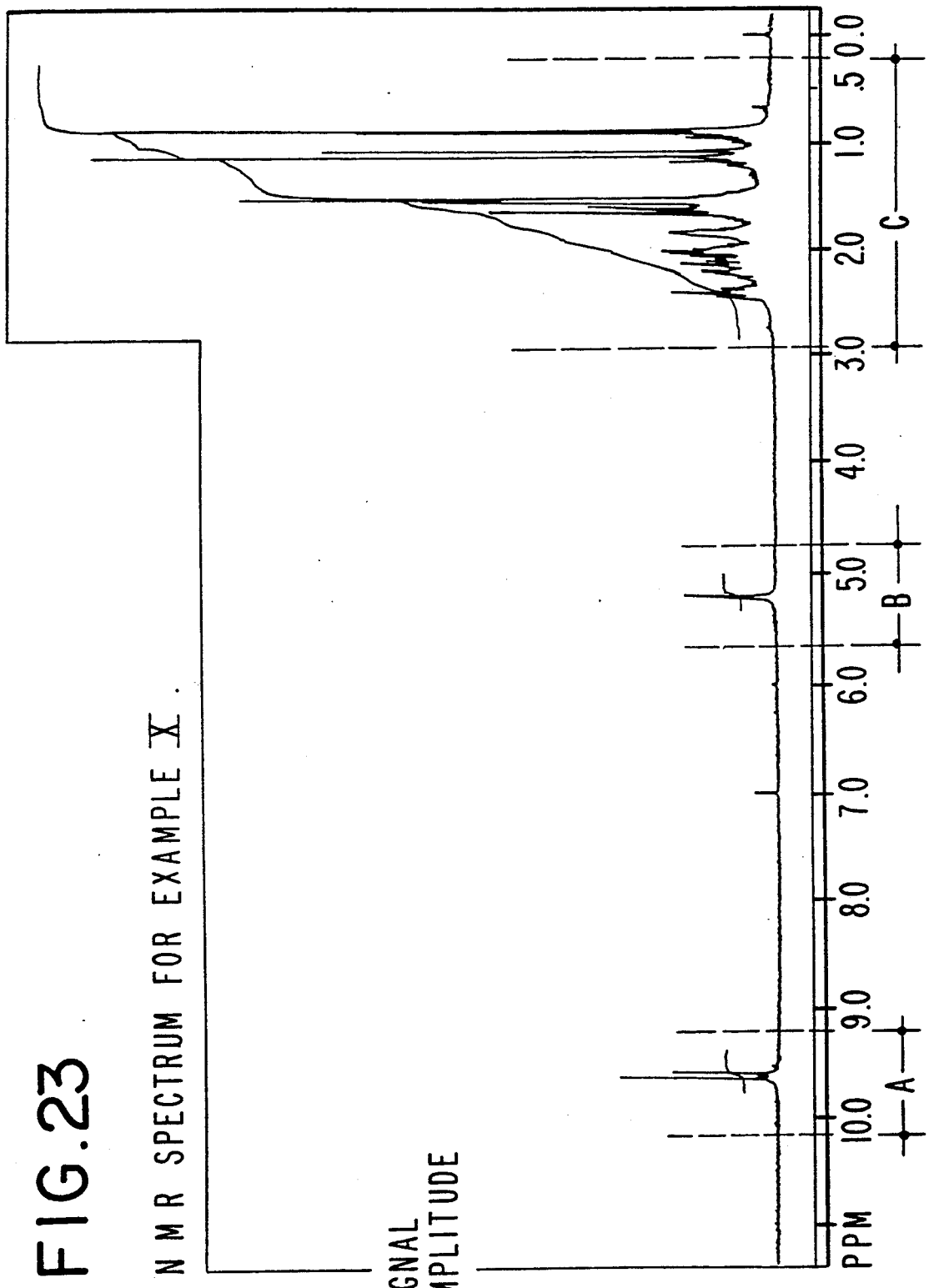
FIG. 23 NMR SPECTRUM FOR EXAMPLE X.

FIG.23-A
FIG.23-B
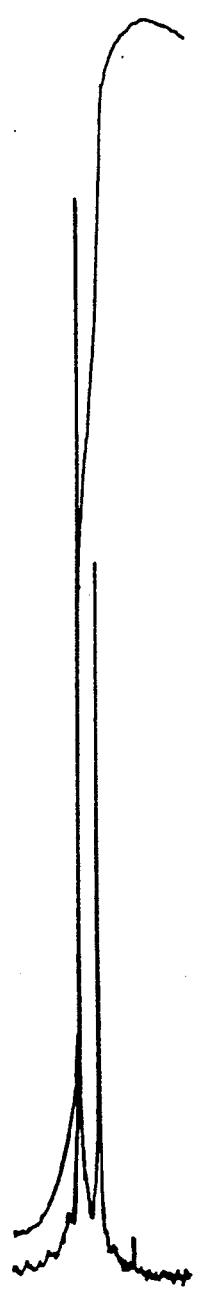
9.6
PPM
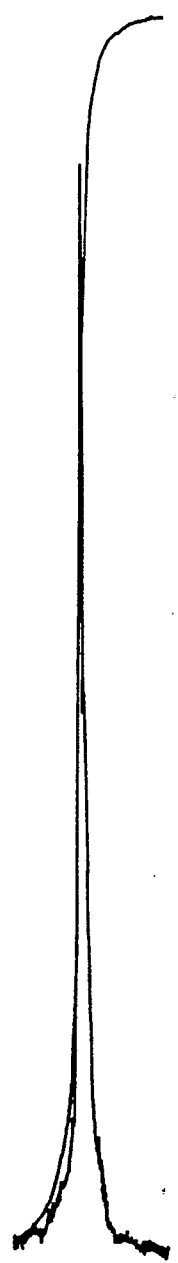
5.2
PPM

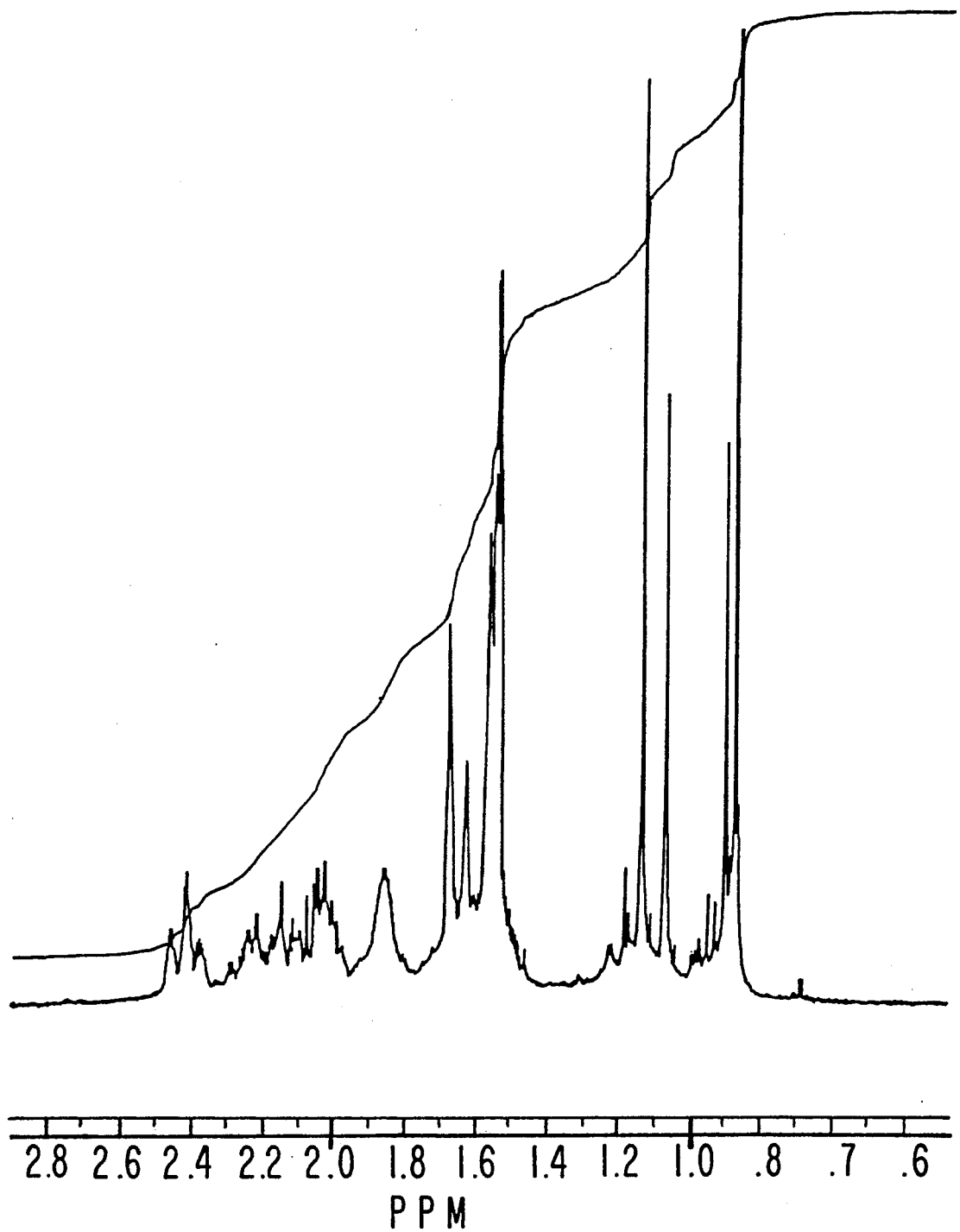
FIG.23-C

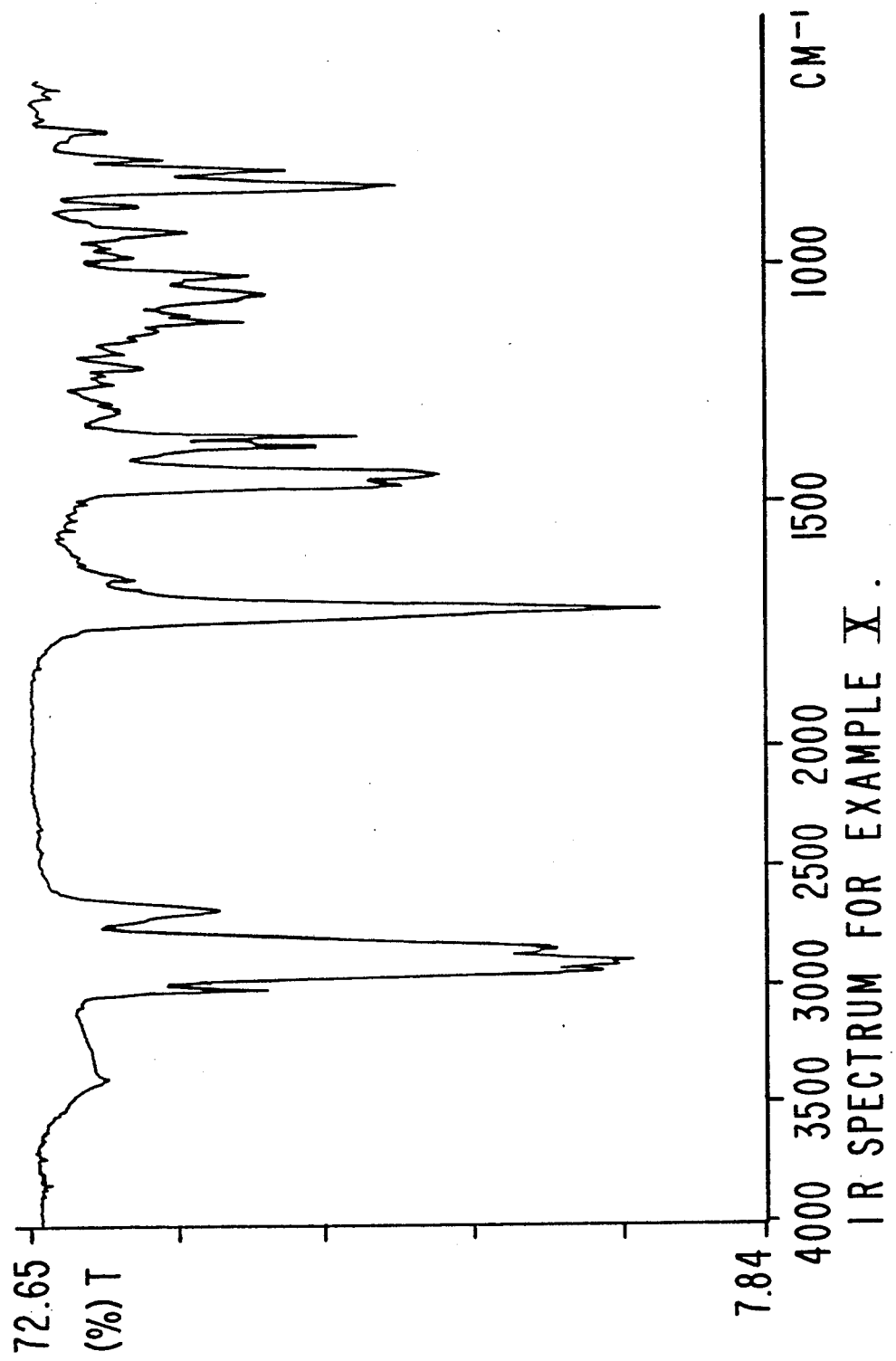
FIG. 24 IR SPECTRUM FOR EXAMPLE X.

GLC PROFILE FOR EXAMPLE XI

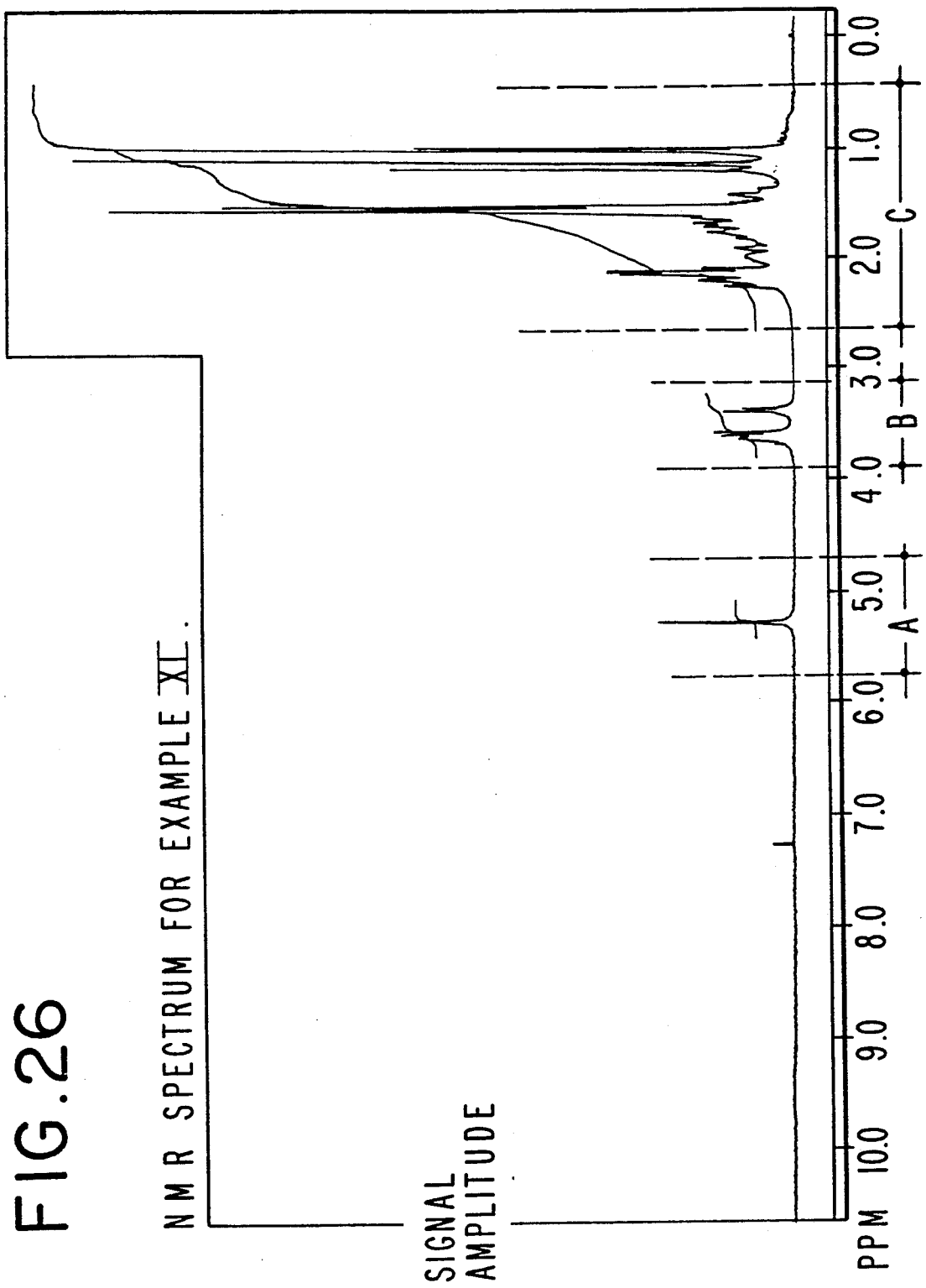
FIG. 26 NMR SPECTRUM FOR EXAMPLE XI.

FIG.26-A
FIG.26-B
5.2
PPM
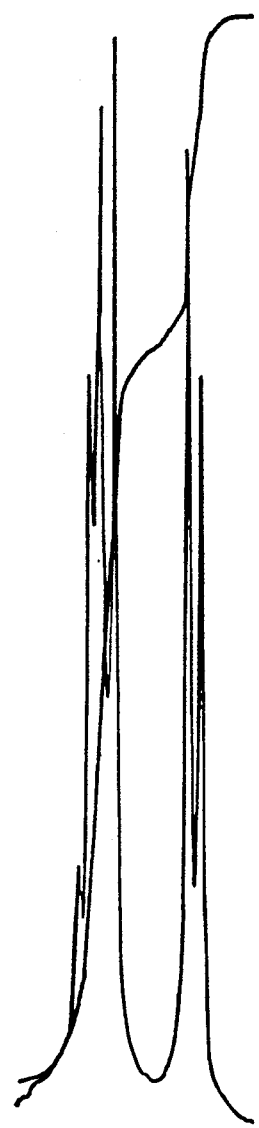
3.6 3.4
PPM

FIG.26-C
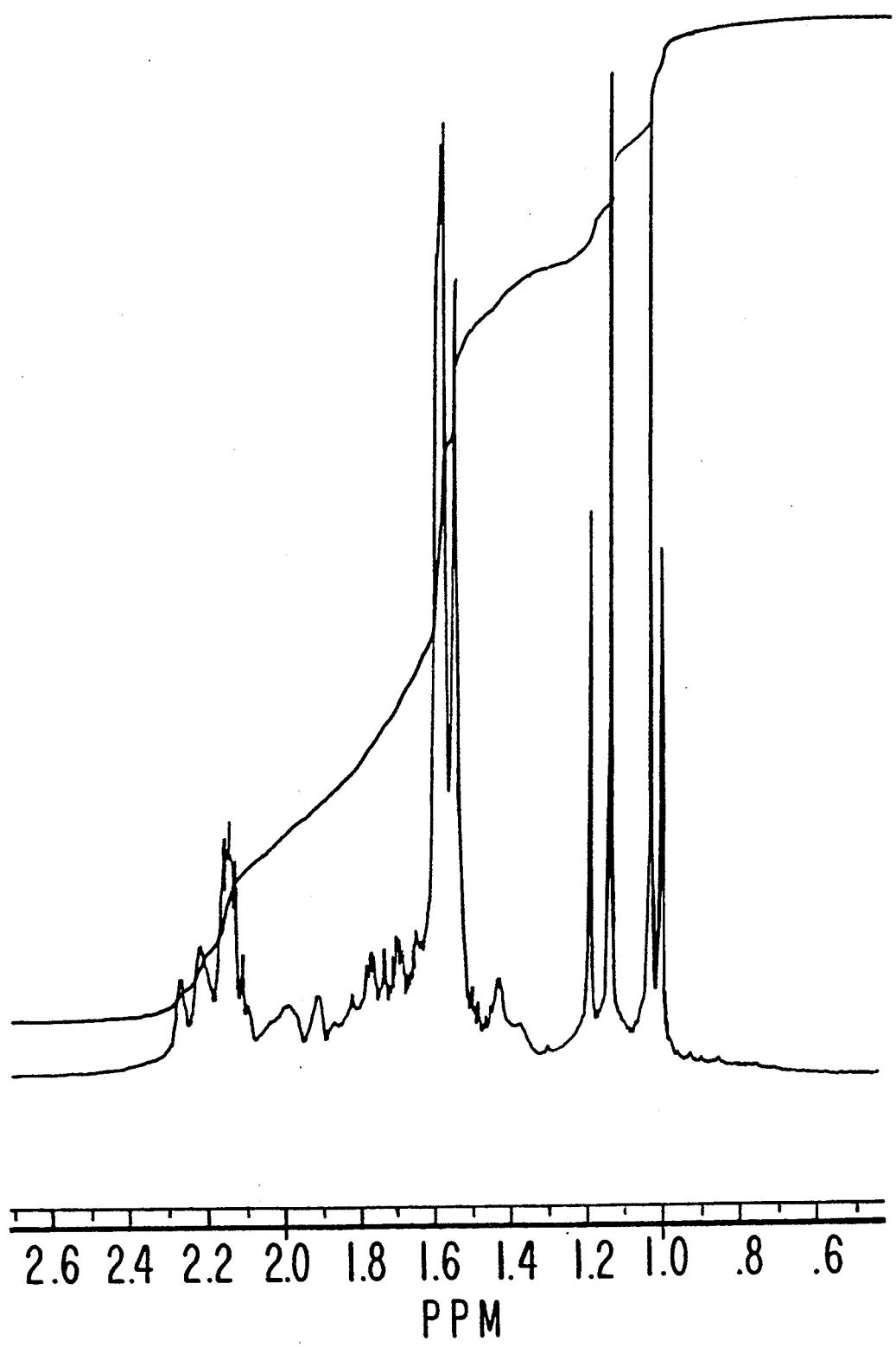

IR SPECTRUM FOR EXAMPLE XI.

GLC PROFILE FOR EXAMPLE XII.

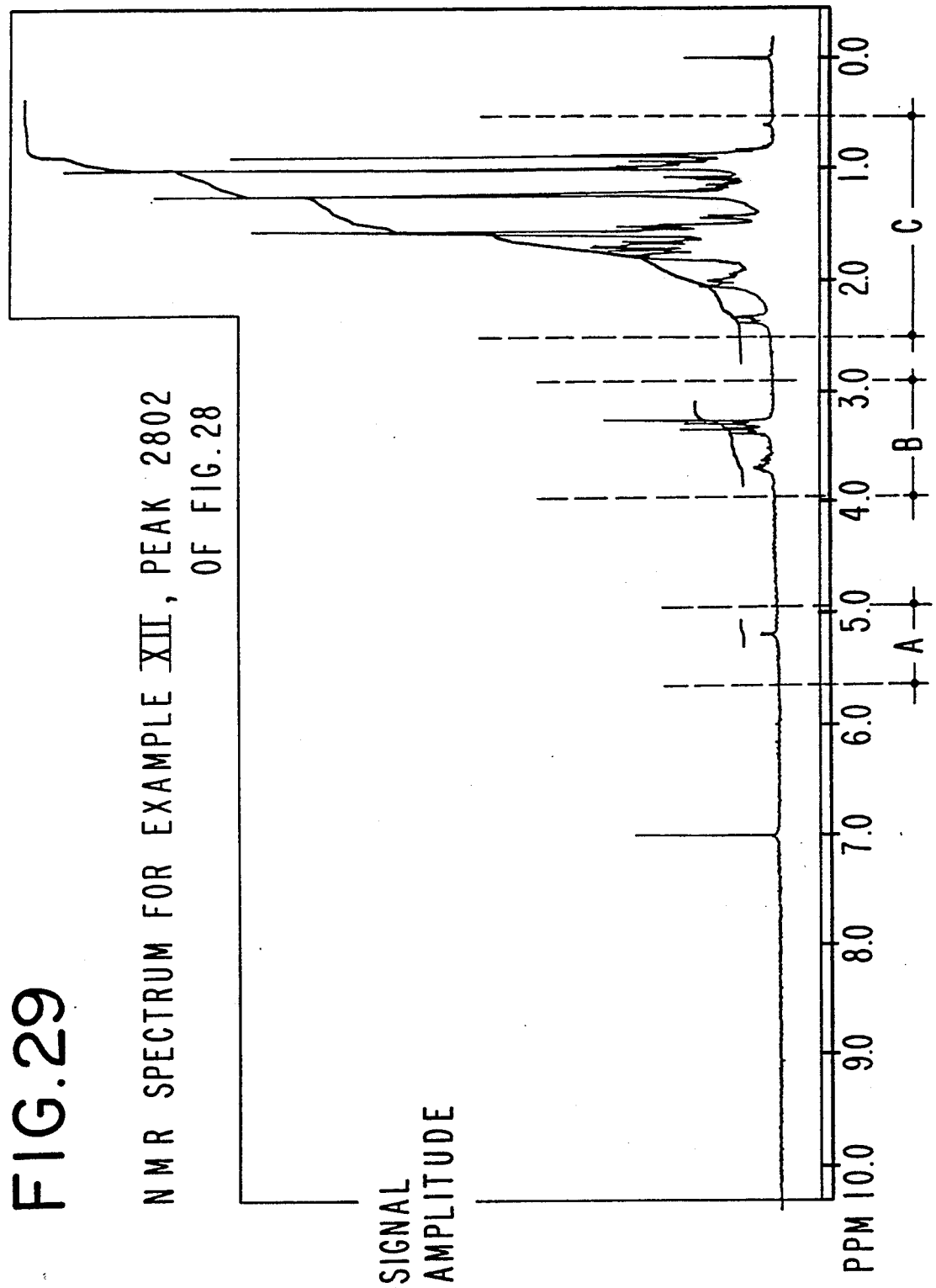
FIG. 29 NMR SPECTRUM FOR EXAMPLE XII, PEAK 2802 OF FIG. 28

FIG. 29-A
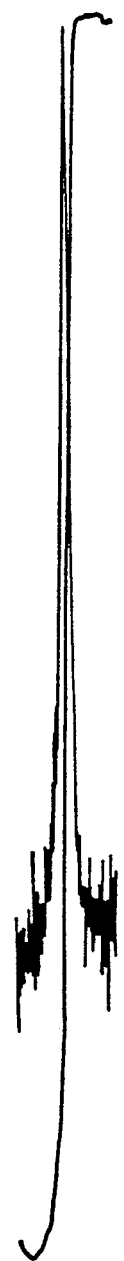
5.2
PPM
FIG. 29-B
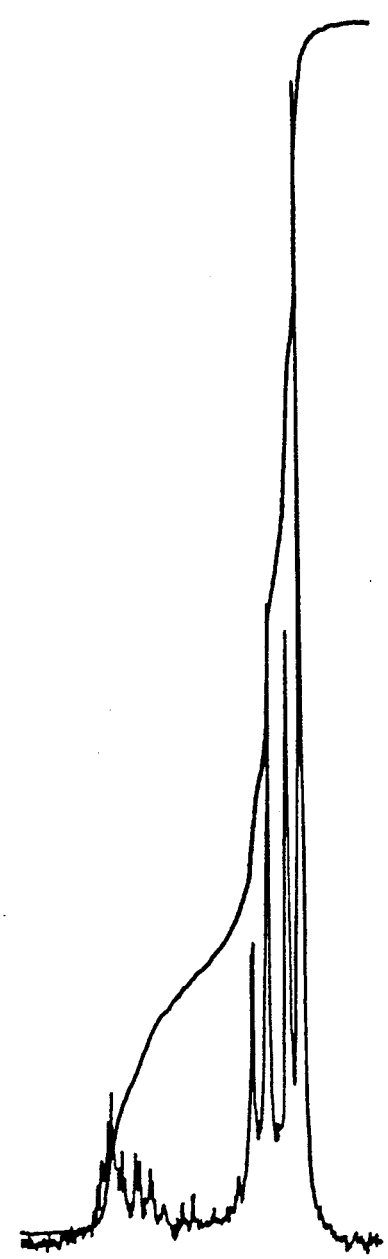
3.8 3.6 3.4 3.2
PPM

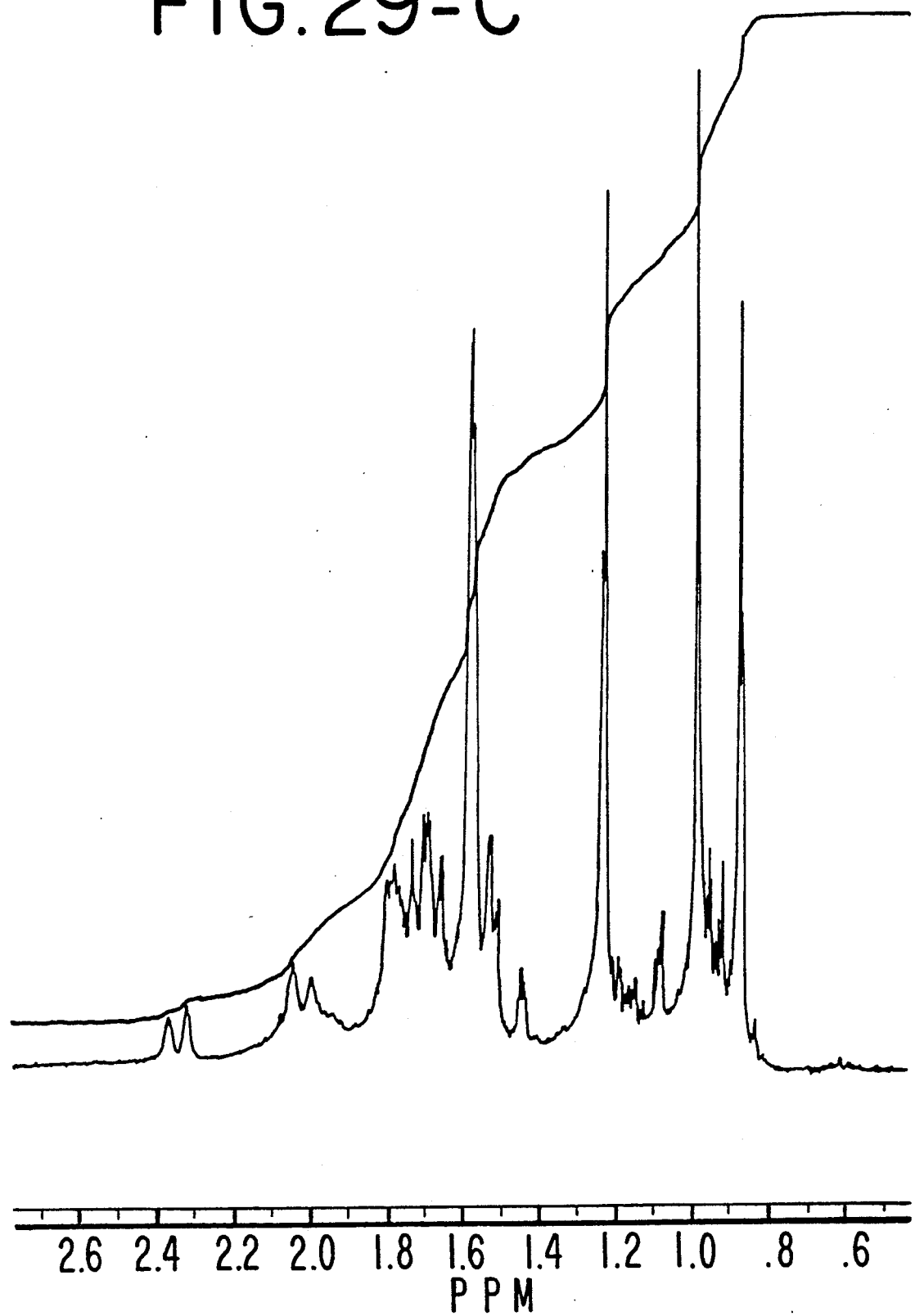
FIG. 29-C

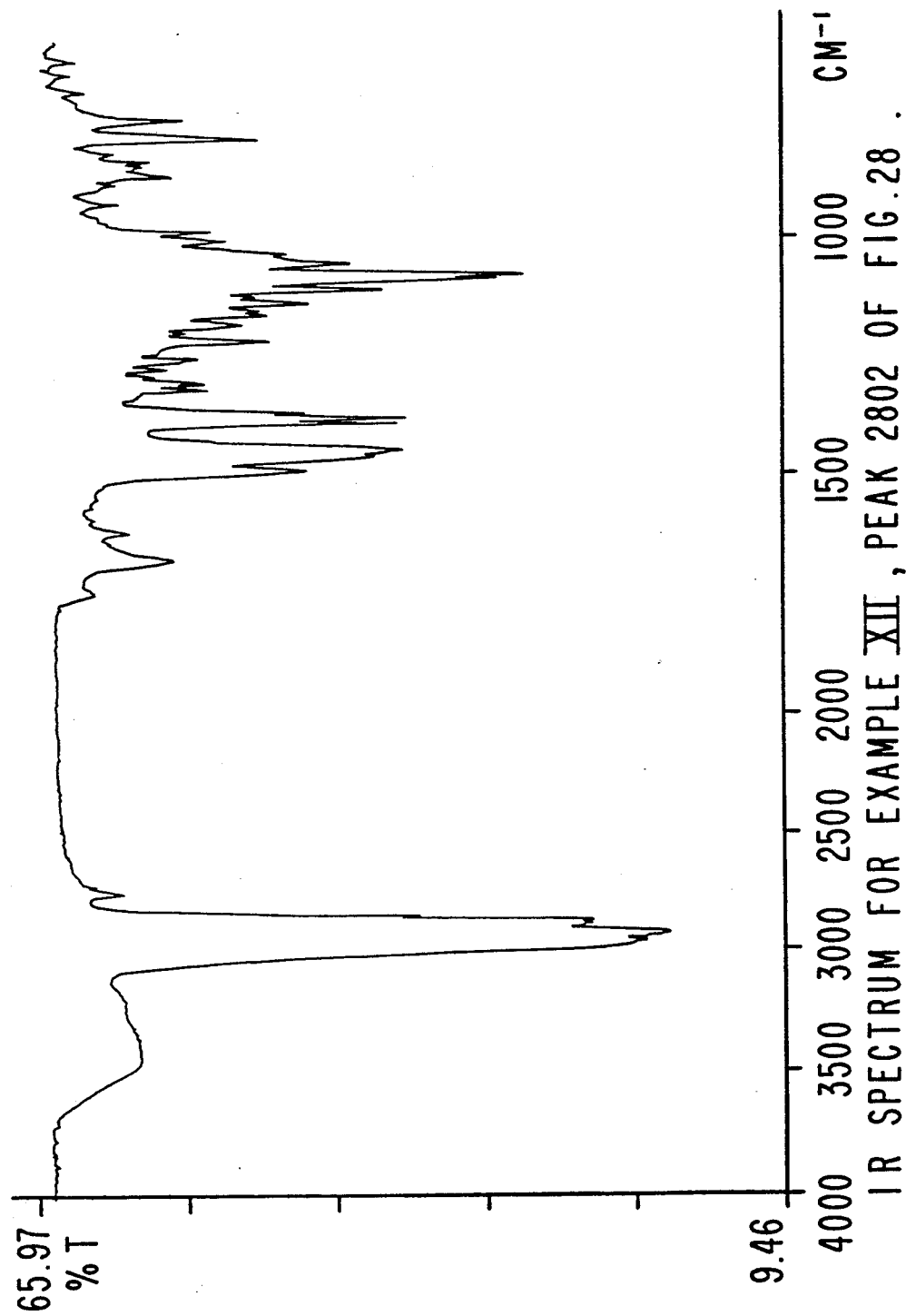

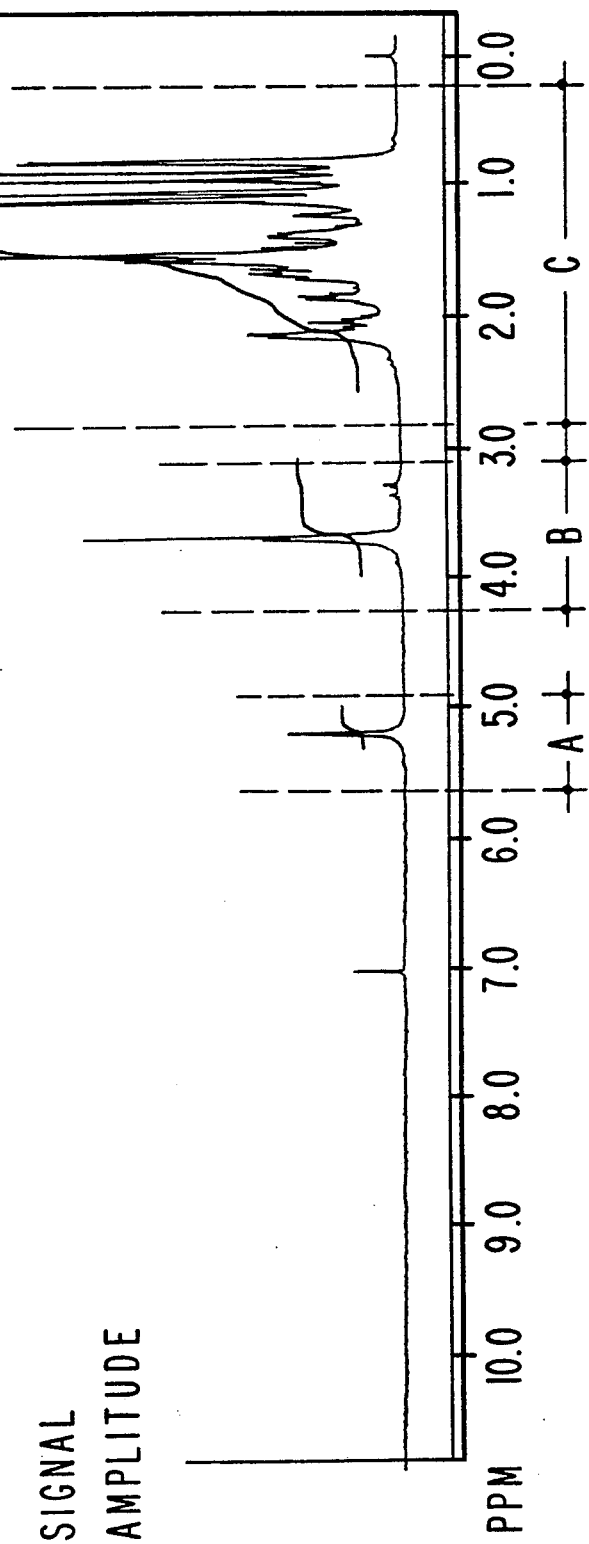
FIG. 31 NMR SPECTRUM FOR EXAMPLE XII, (PEAK 2800 OF FIG. 28).

FIG.31-A  FIG.31-B
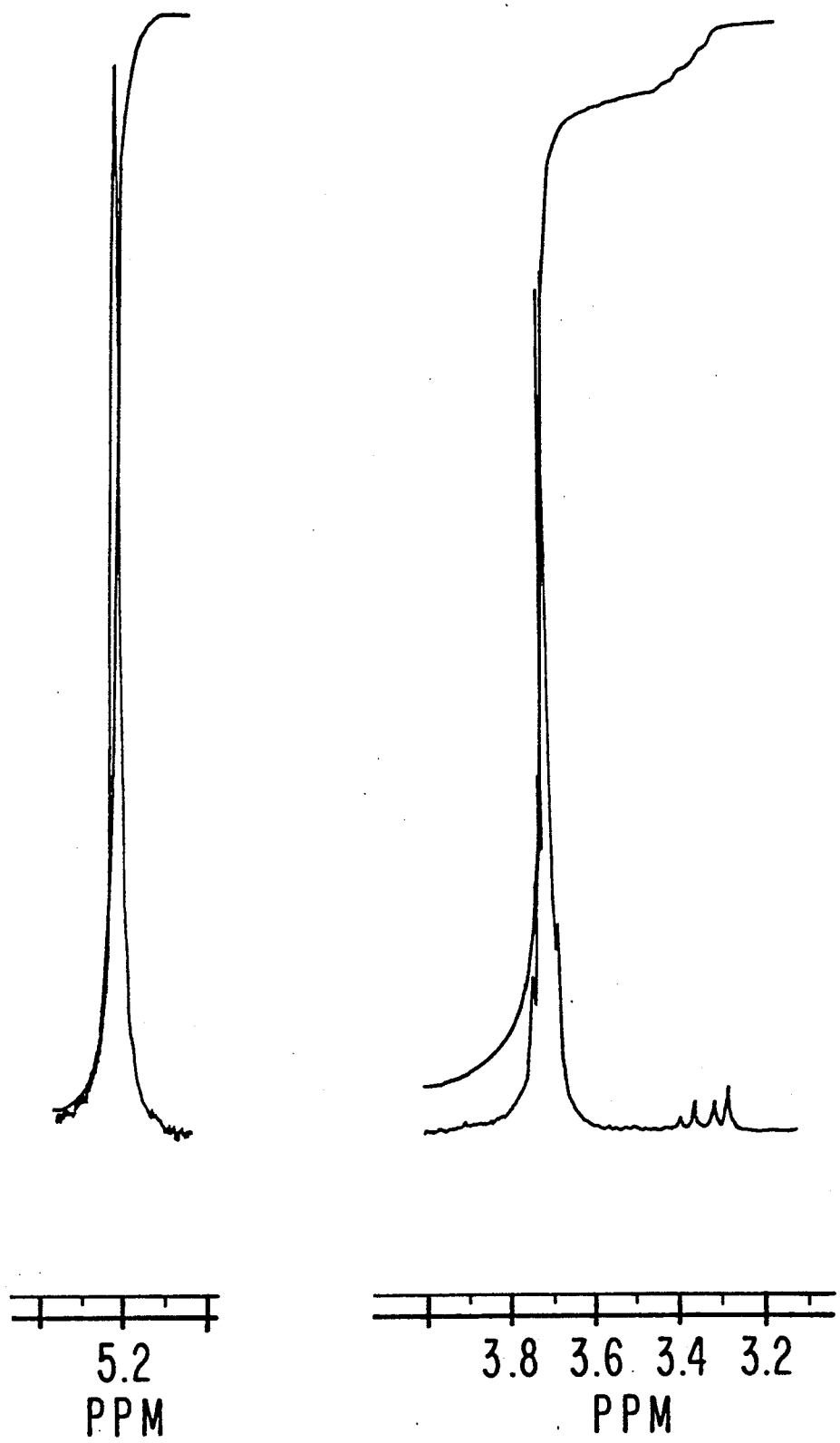

FIG. 31-C
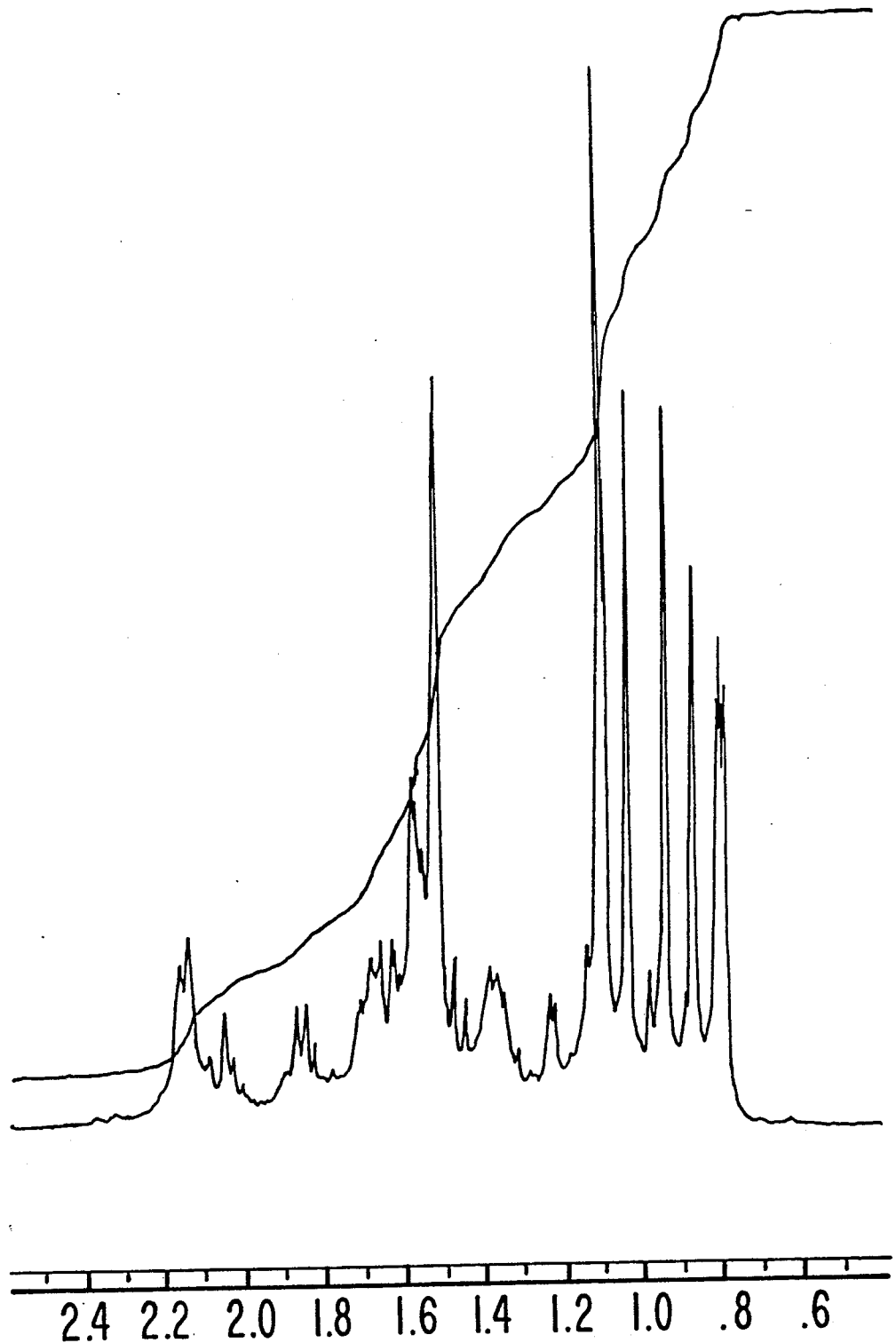

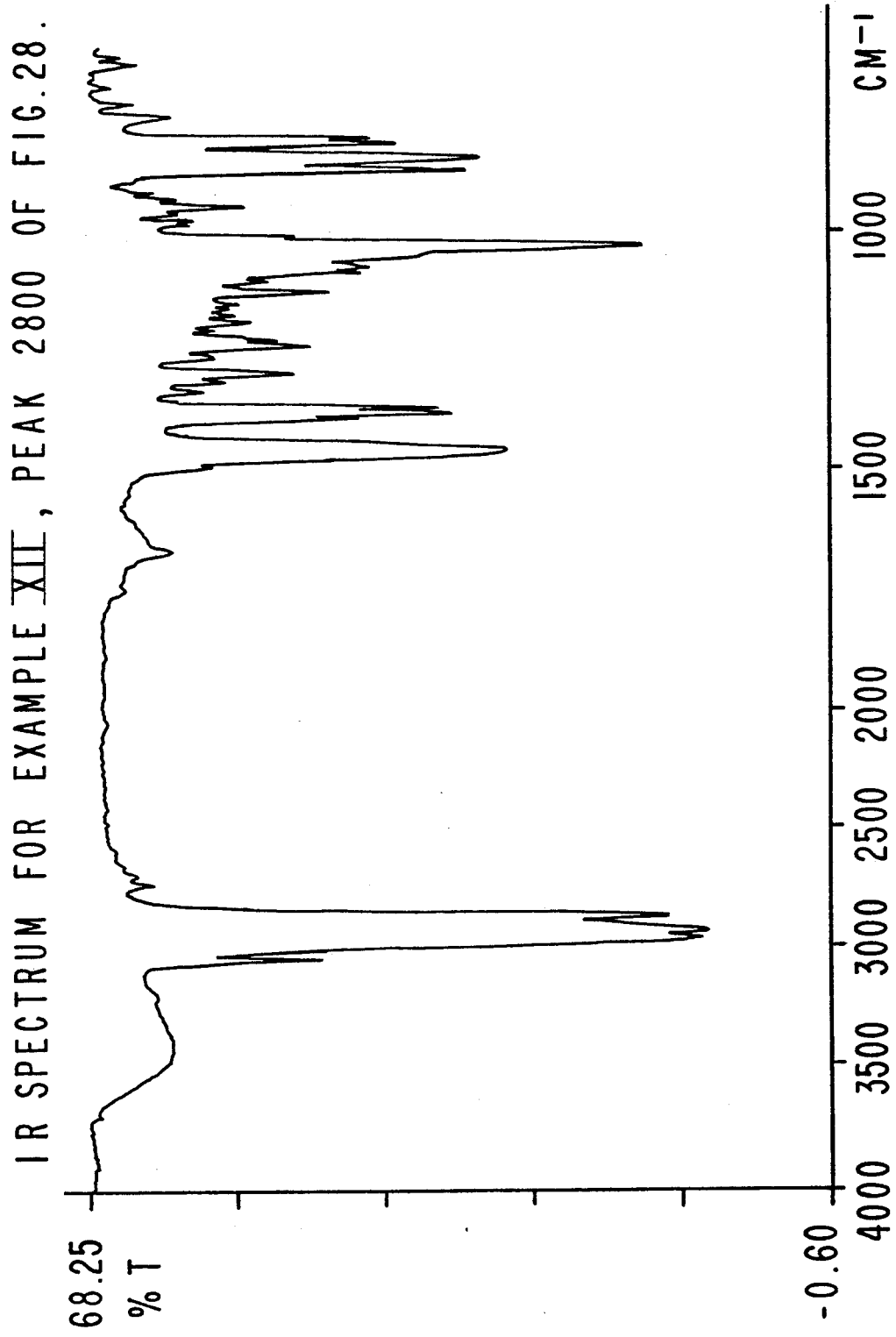

CAMPHONYL SPIROCYCLOOXAOCTANE-CONTAINING COMPOSITIONS, ORGANOLEPTIC USES THEREOF AND PROCESS FOR PREPARING SAME

This application is a continuation-in-part of application for United States Letters Patent, Ser. No. 588,825 filed on Sep. 27, 1990, now U.S. Pat. No. 5,081,262.

BACKGROUND OF THE INVENTION

This invention relates to camphonyl spirocyclooxaoctane-containing compositions and mixtures thereof with cyclopentenyl oxabicyclooctanes and uses thereof in augmenting or enhancing the aroma of perfume compositions, perfumed articles and colognes.

Cassis, Black current, piney, balsamic, animalic, camphoraceous, woody and pepper aromas, with animalic, piney, fruity, camphoraceous, woody, peppery, balsamic, terpenic and cassis topnotes are particularly desirable in augmenting or enhancing the aroma of perfume compositions, colognes and perfumed articles (e.g., solid or liquid anionic, cationic, nonionic or zwitterionic detergents, fabric softener compositions, fabric softener articles, hair preparations, cosmetic powders and perfumed polymers).

Compounds having polycyclic nuclei, e.g., oxabicyclooctane nuclei have been known for use in augmenting or enhancing the aroma of perfume compositions, perfumed articles and colognes for a number of years. Thus, the compound having the structure:

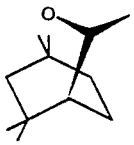

is disclosed at column 4, lines 35-40 of U.S. Pat. No. 4,269,862 (Sprecker, et al, II) to have a minty, camphor, woody and piney aroma profile. U.S. Pat. No. 4,269,862 further discloses the genus defined according to the structure:

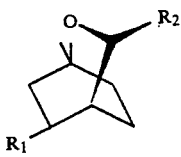

wherein $R_1$ is hydrogen or methyl and $R_2$ is $C_3$–$C_5$ alkyl or alkenyl to have utility in augmenting or enhancing the aroma of perfume compositions, colognes and perfumed articles.

Furthermore, cineole itself having the structure:

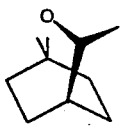

is disclosed by Arctander "Perfume and Flavor Chemicals" (Aroma Chemicals) at monograph 616 to have an eucalyptus aroma (its common name is "eucalyptol").

Nothing in the prior art, however, discloses the camphonyl spirocyclooxaoctane-containing compositions of our invention or their organoleptic uses or mixtures of such camphonyl spirocyclooxactane-containing compositions with cyclopentenyloxabicyclooctane derivatives.

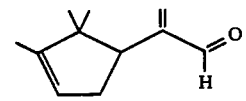

(Conditions: Carbowax column programmed at 220° C. isothermal).

Figure 2:
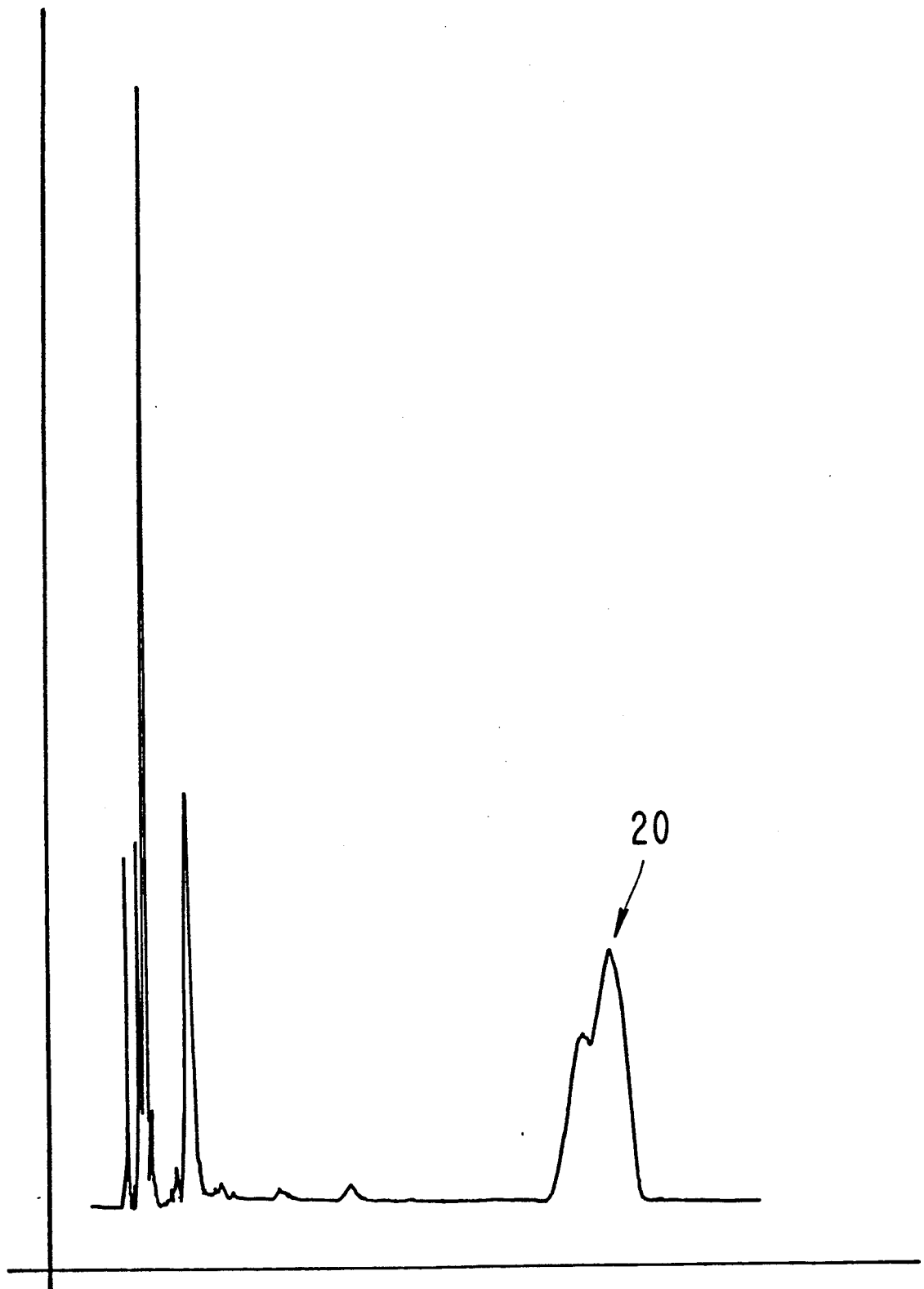

FIG. 2 is the GLC profile for the reaction product of Example II containing the mixture of compounds having the structures:

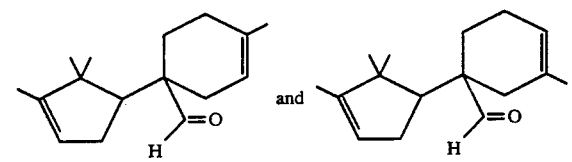

(Conditions: Carbowax column programmed at 220° C. isothermal).

FIG. 3 is the NMR spectrum for the mixture of compounds having the structures:

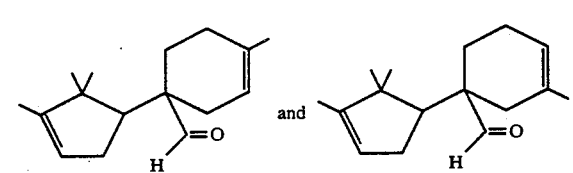

prepared according to Example II.

FIG. 4 is the GLC profile for the reaction product of Example III containing the compounds having the structures:

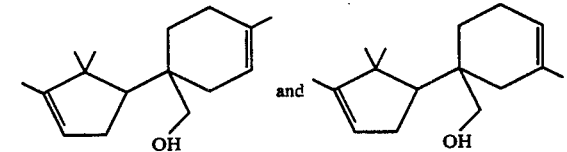

FIG. 5 is the infra-red spectrum for the mixture of compounds of Example III having the structures:

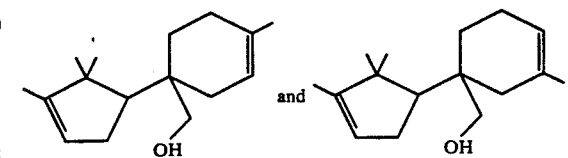

Figure 6A:
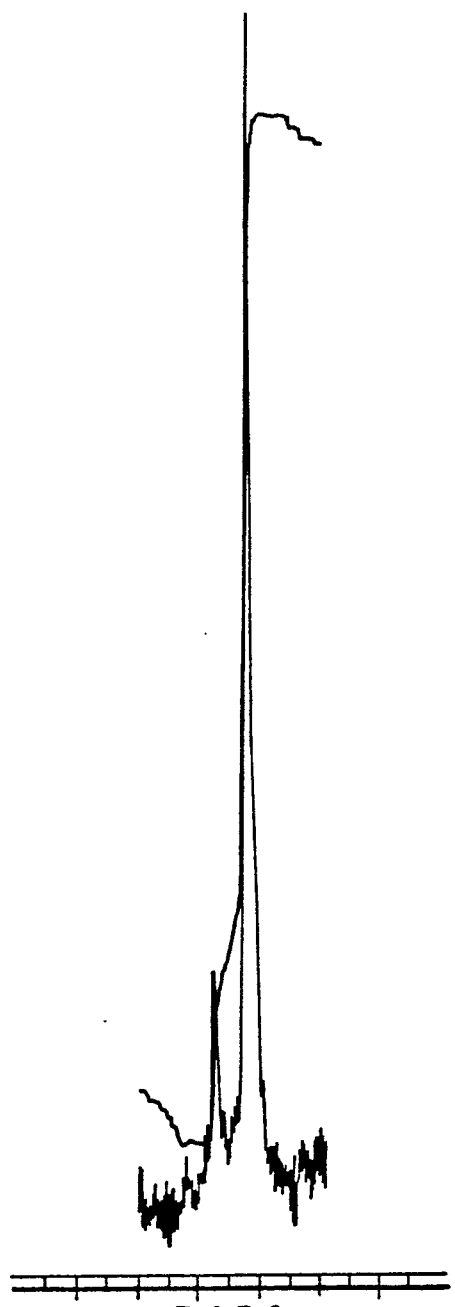
Figure 6B:
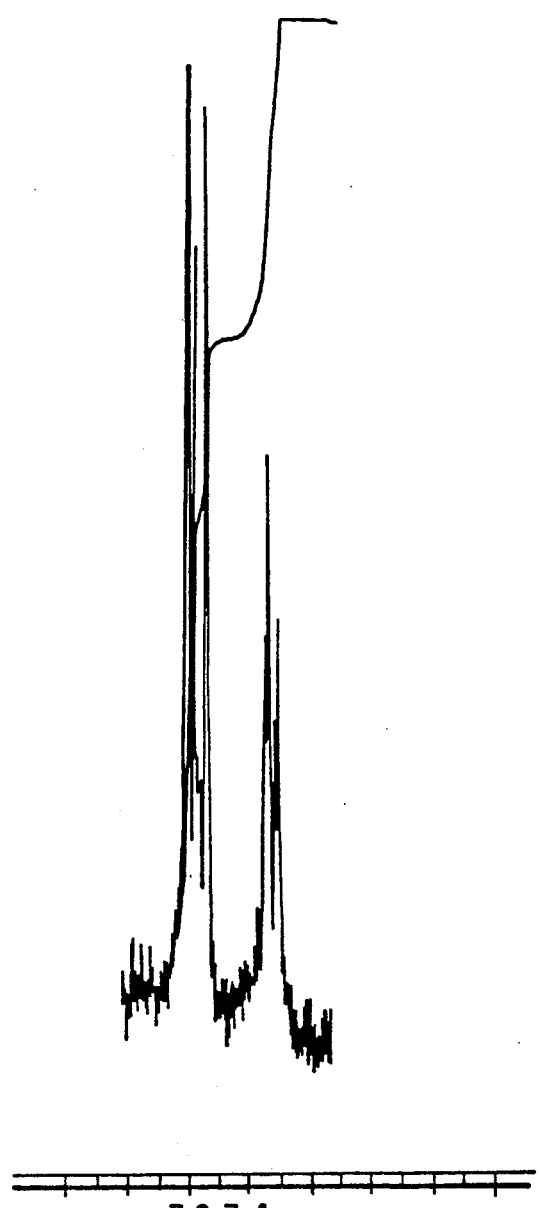
Figure 6C:
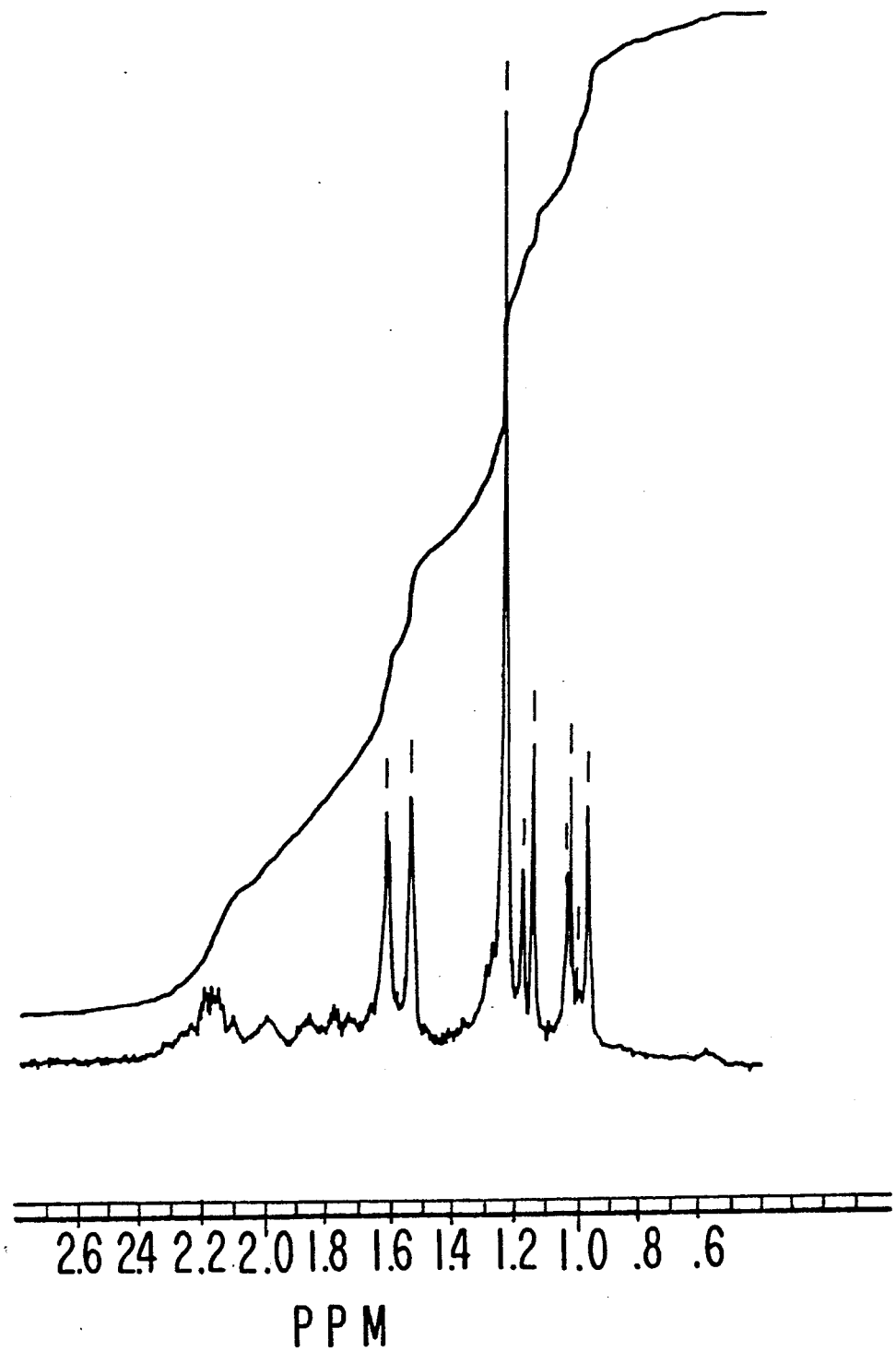

FIG. 6 is the NMR spectrum for the mixture of compounds having the structures:

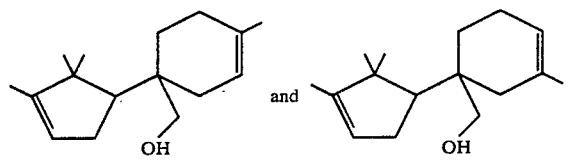

prepared according Example III.

FIGS. 6-A, 6-B and 6-C are detailed sections of the NMR spectrum of FIG. 6.

Figure 7:
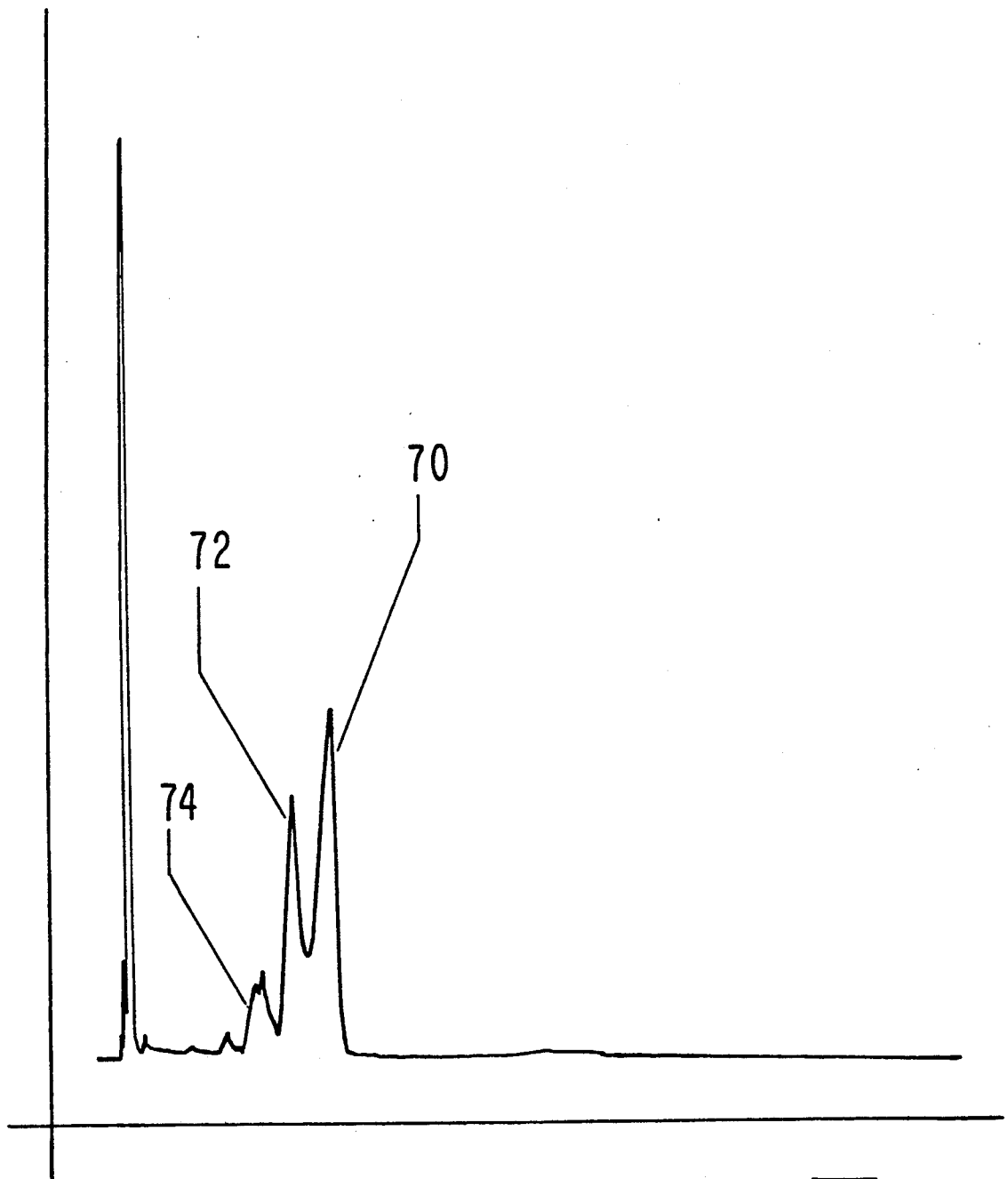

FIG. 7 is the GLC profile for the reaction product of Example IV containing the compounds having the structures:

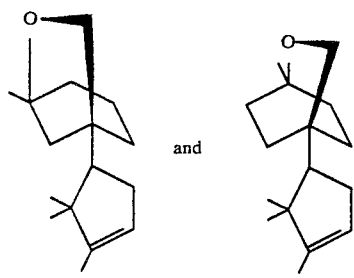

Figure 8:
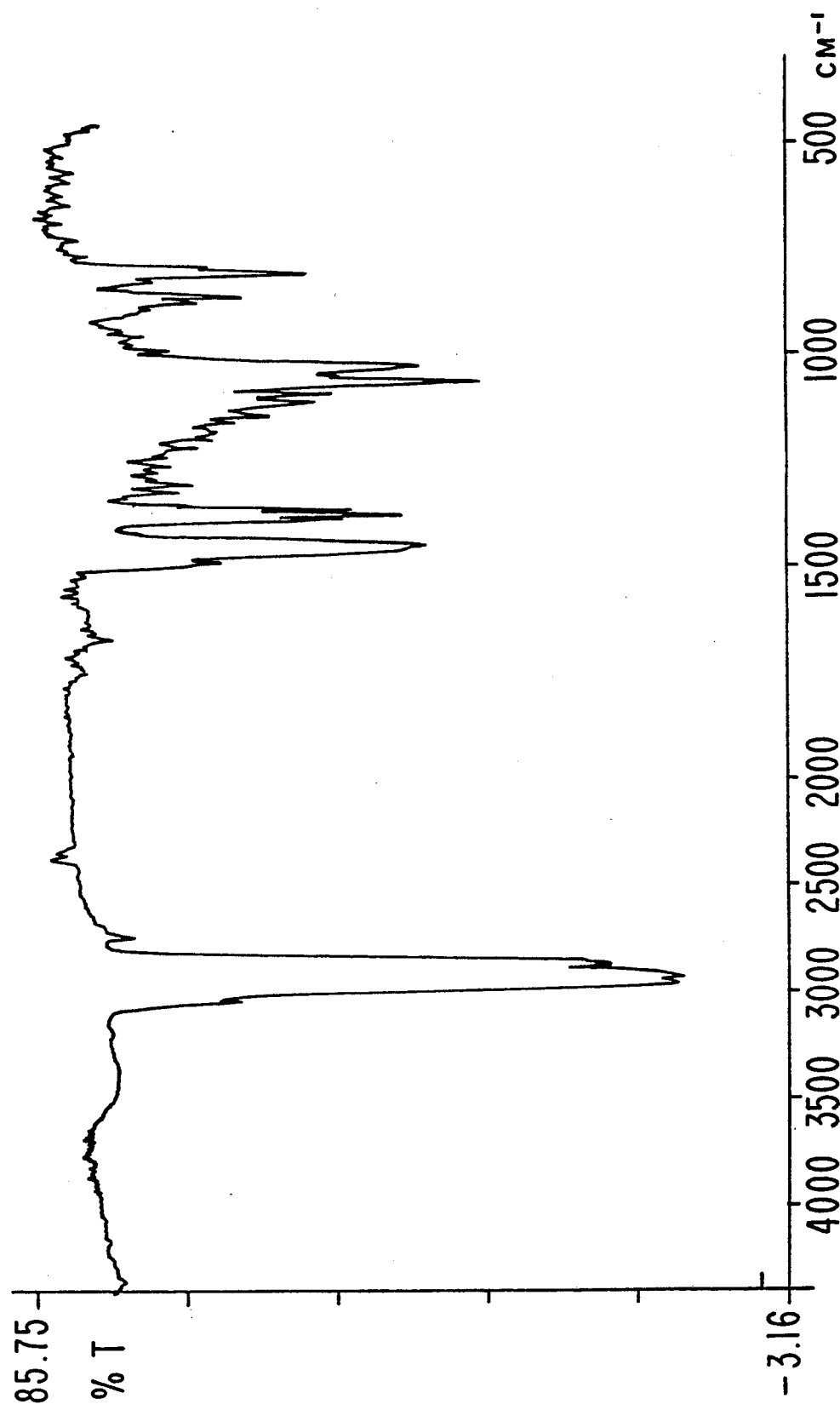

FIG. 8 is the infra-red spectrum for the mixture of compounds having the structures:

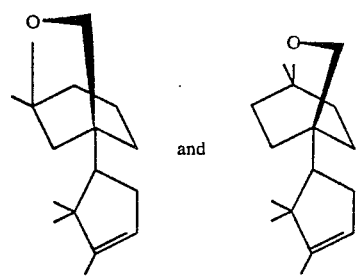

prepared according to Example IV.

Figure 9:
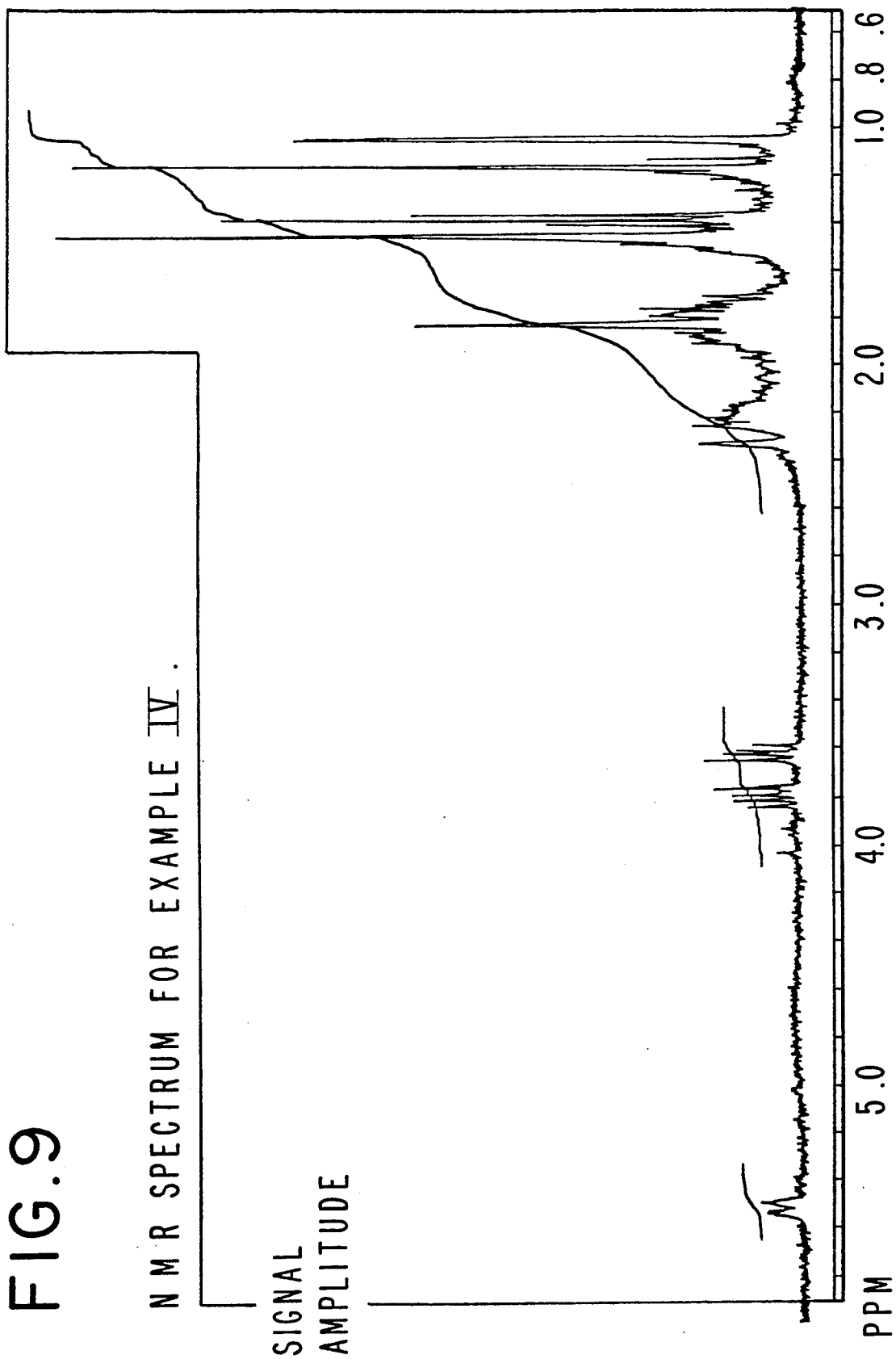

FIG. 9 is the NMR spectrum for the mixture of compounds having the structures:

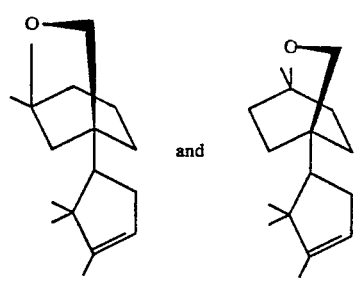

prepared according to Example IV.

Figure 10:
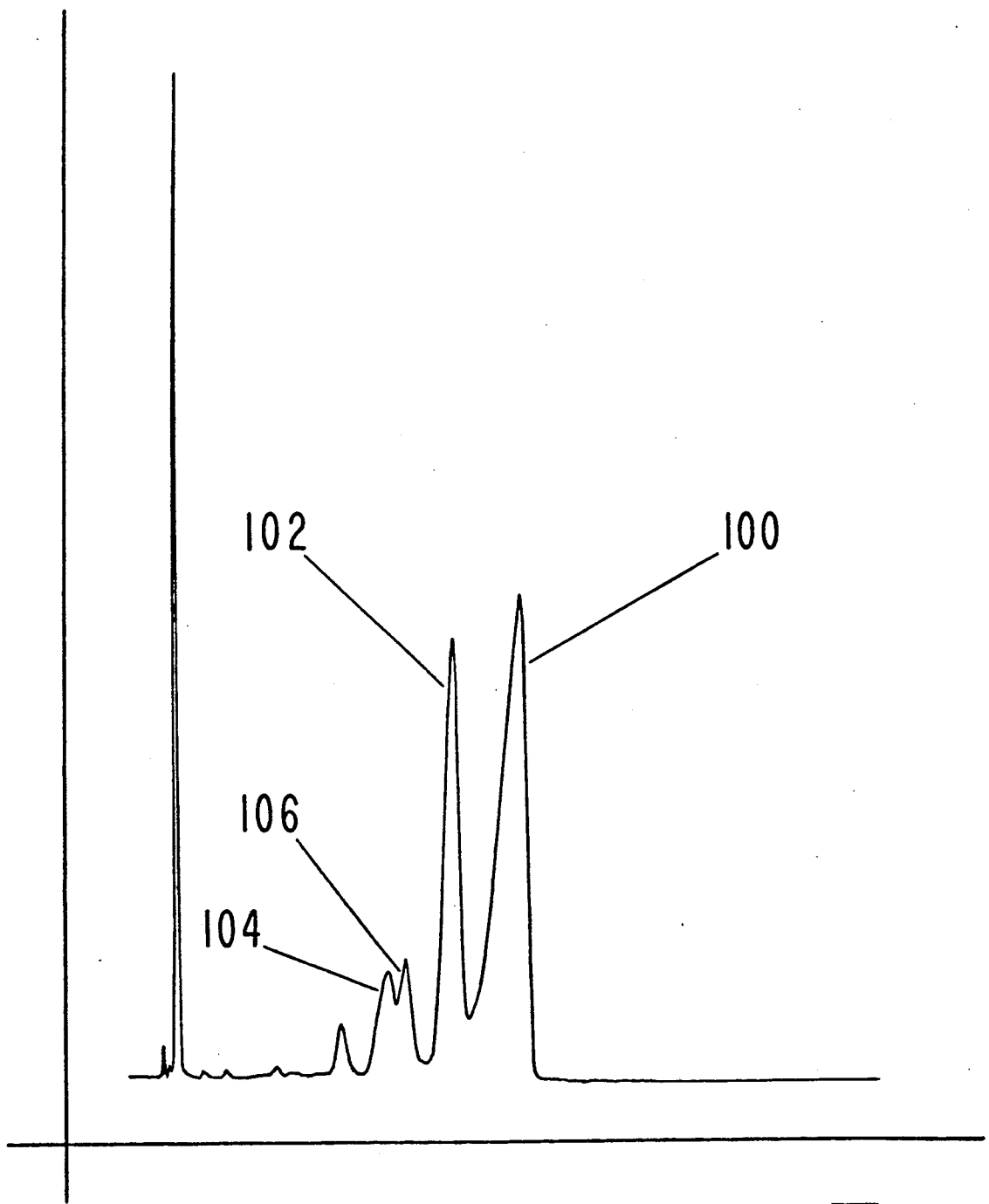

FIG. 10 is the GLC profile for the reaction product of Example V containing the compounds having the structures:

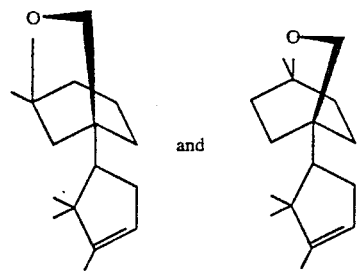

(Conditions: Carbowax column programmed at 220° C. isothermal).

FIG. 11 is a partial side elevation and partial sectional view of an apparatus for forming polymer pellets scented with one of the perfume compositions or perfumery materials of our invention containing the camphonyl spirocyclooxaoctane-containing compositions.

FIG. 12 is a section taken on line 12—12 of FIG. 11.

Figure 13:
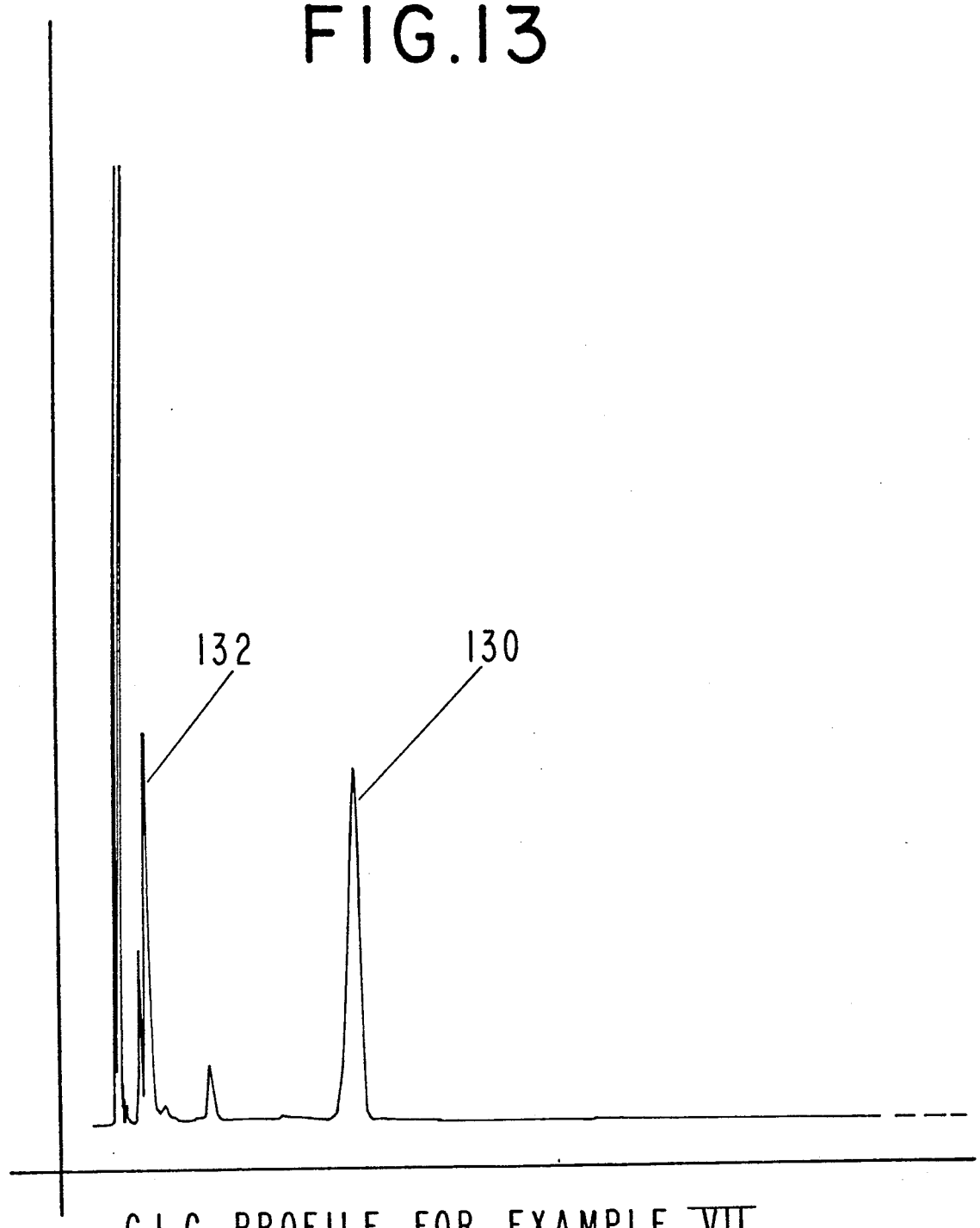

FIG. 13 is a GLC profile of the reaction product of Example VII containing the compounds having the structures:

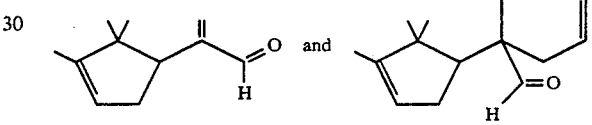

(Conditions: Carbowax column programmed at 220° C. isothermal).

FIG. 14 is the NMR spectrum for the peak indicated by reference numeral 130 for the compound having the structure:

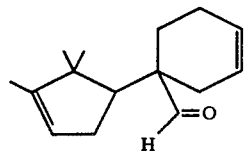

prepared according to Example VII.

FIGS. 14A, 14B and 14C are detailed sections of the NMR spectrum of FIG. 14.

FIG. 14D is the infra-red spectrum for the compound having the structure:

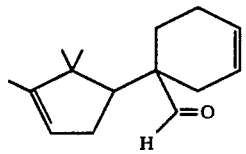

of Example VII.

Figure 15:
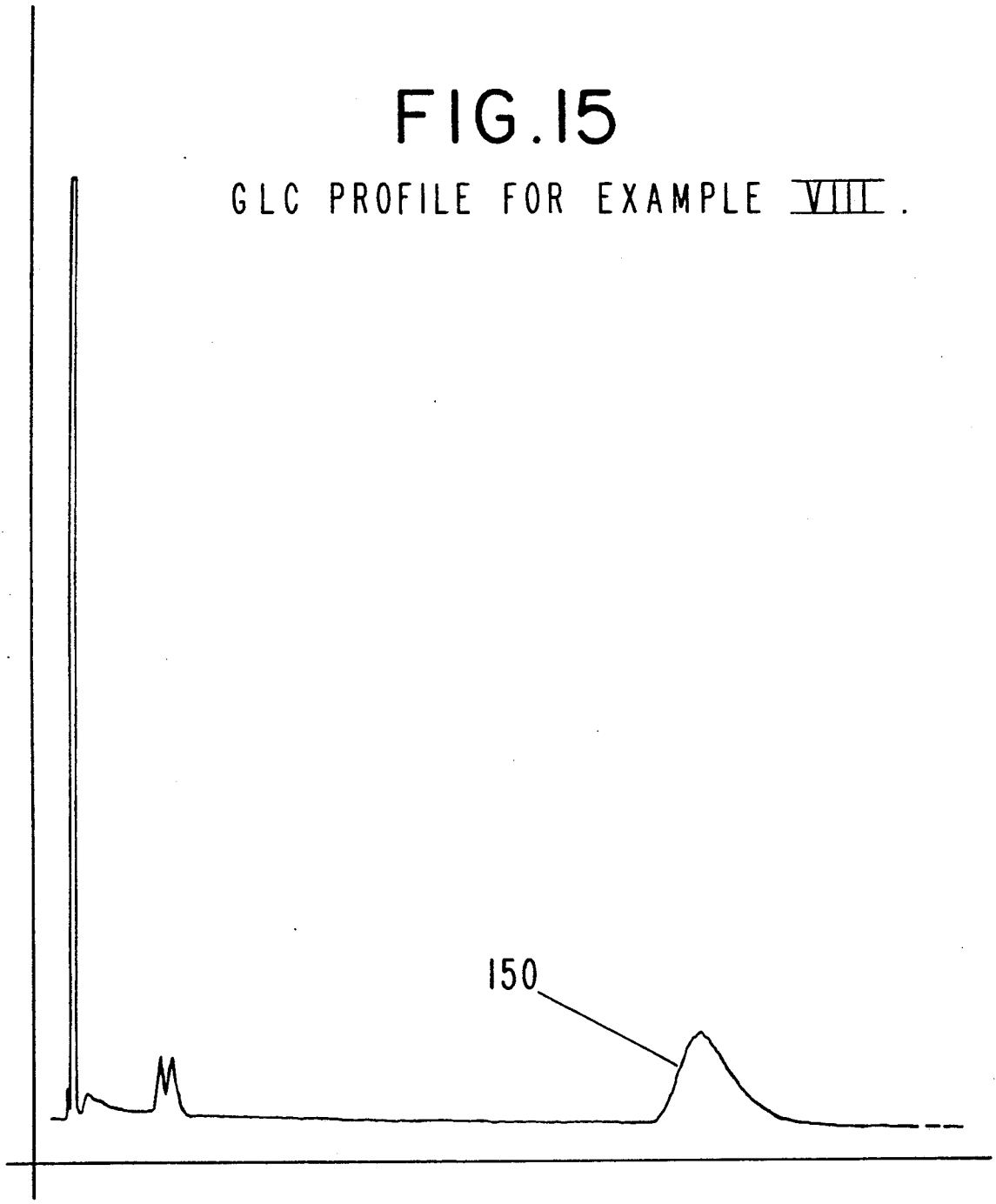

FIG. 15 is the GLC profile for the reaction product of Example VIII containing the compound having the structure:

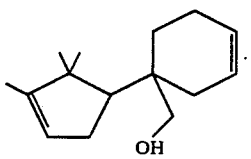

(Conditions: SE-30 column programed at 220° C. isothermal).

FIG. 16 is the NMR spectrum for the compound having the structure:

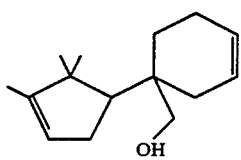

prepared according to Example VIII.

FIGS. 16A, 16B and 16C are detailed sections of the NMR spectrum of FIG. 16.

FIG. 17 is the GLC profile for the reaction product of Example IX containing the compounds having the structures:

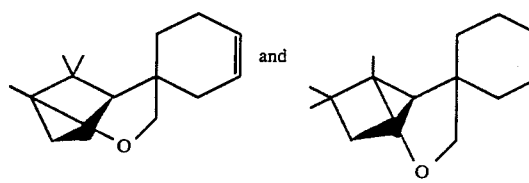

FIG. 18 is the NMR spectrum for the peak indicated by reference numeral 174 of FIG. 17 for one or both of the compounds having the structures:

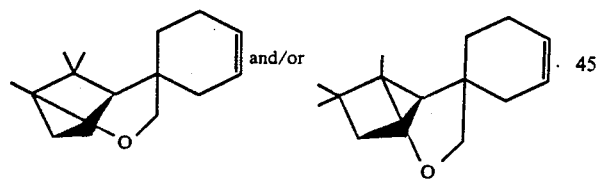

FIGS. 18A, 18B and 18C are detailed sections of the NMR spectrum of FIG. 18.

FIG. 19 is the infra-red spectrum for the peak indicated by reference numeral 174 of FIG. 17 for one or both of the compounds having the structures:

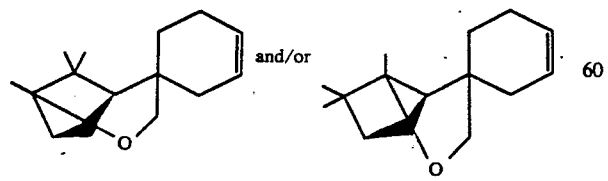

FIG. 20 is the NMR spectrum for the peak indicated by reference numeral 172 of FIG. 17 for one or both of the compounds having the structures:

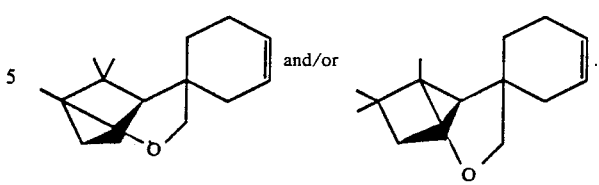

FIGS. 20A, 20B and 20C are detailed sections of the NMR spectrum of FIG. 20.

FIG. 21 is the infra-red spectrum for the peak indicated by reference numeral 172 of FIG. 17 for one or both of the compounds having the structures:

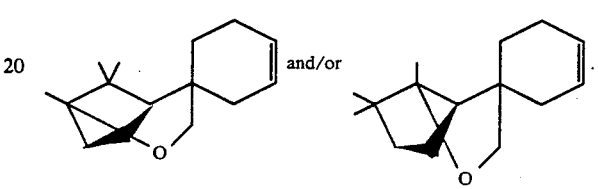

Figure 22:
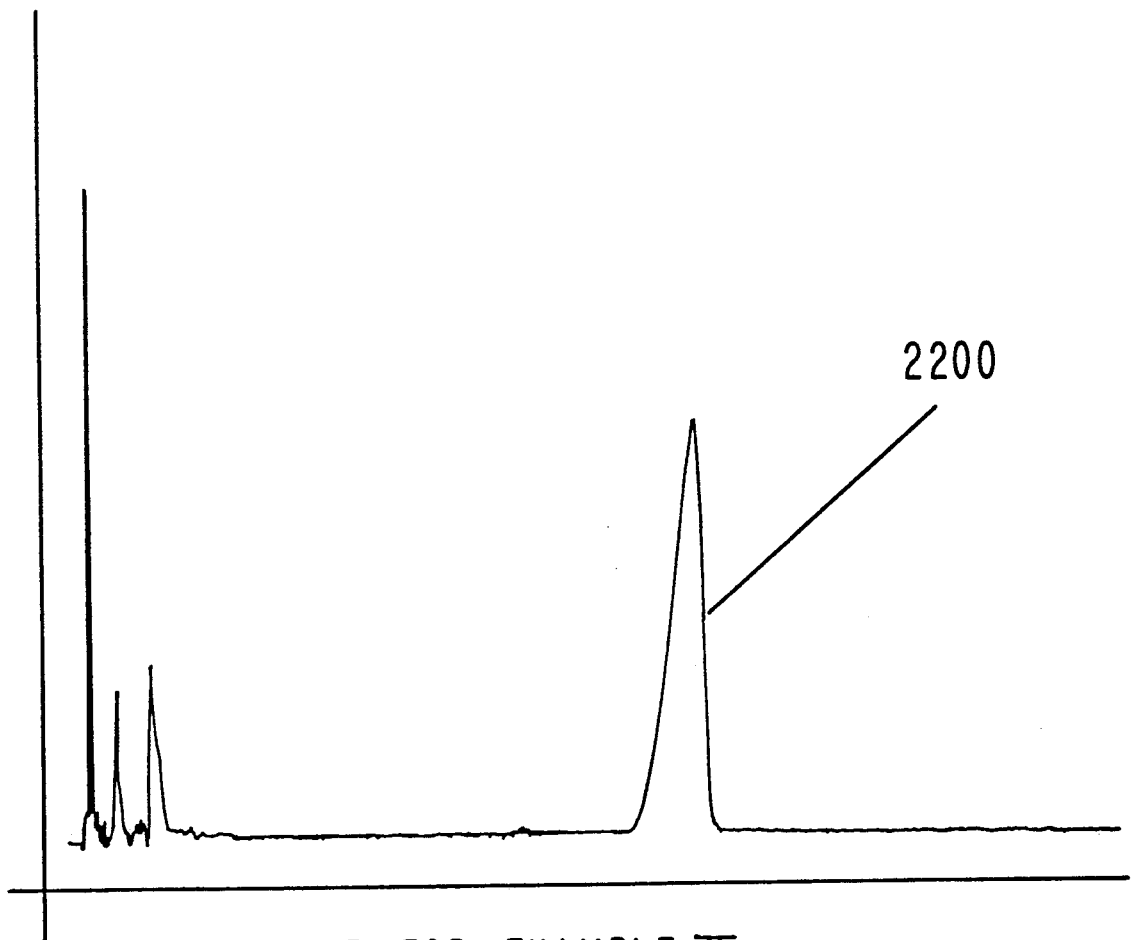

FIG. 22 is the GLC profile for the reaction product of Example X containing the compound having the structure:

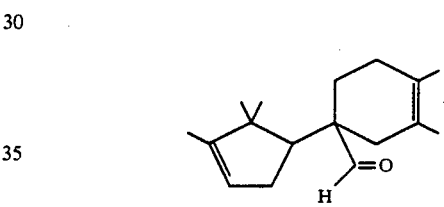

FIG. 23 is the NMR spectrum for the peak indicated by reference numeral 2200 of FIG. 22 for the compound having the structure:

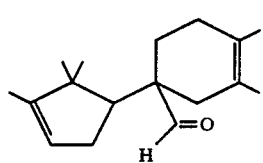

FIGS. 23A, 23B and 23C are detailed sections of the NMR spectrum of FIG. 23.

FIG. 24 is the infra-red spectrum for the compound having the structure:

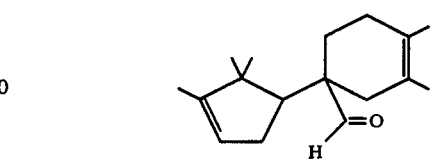

prepared according to Example X.

Figure 25:
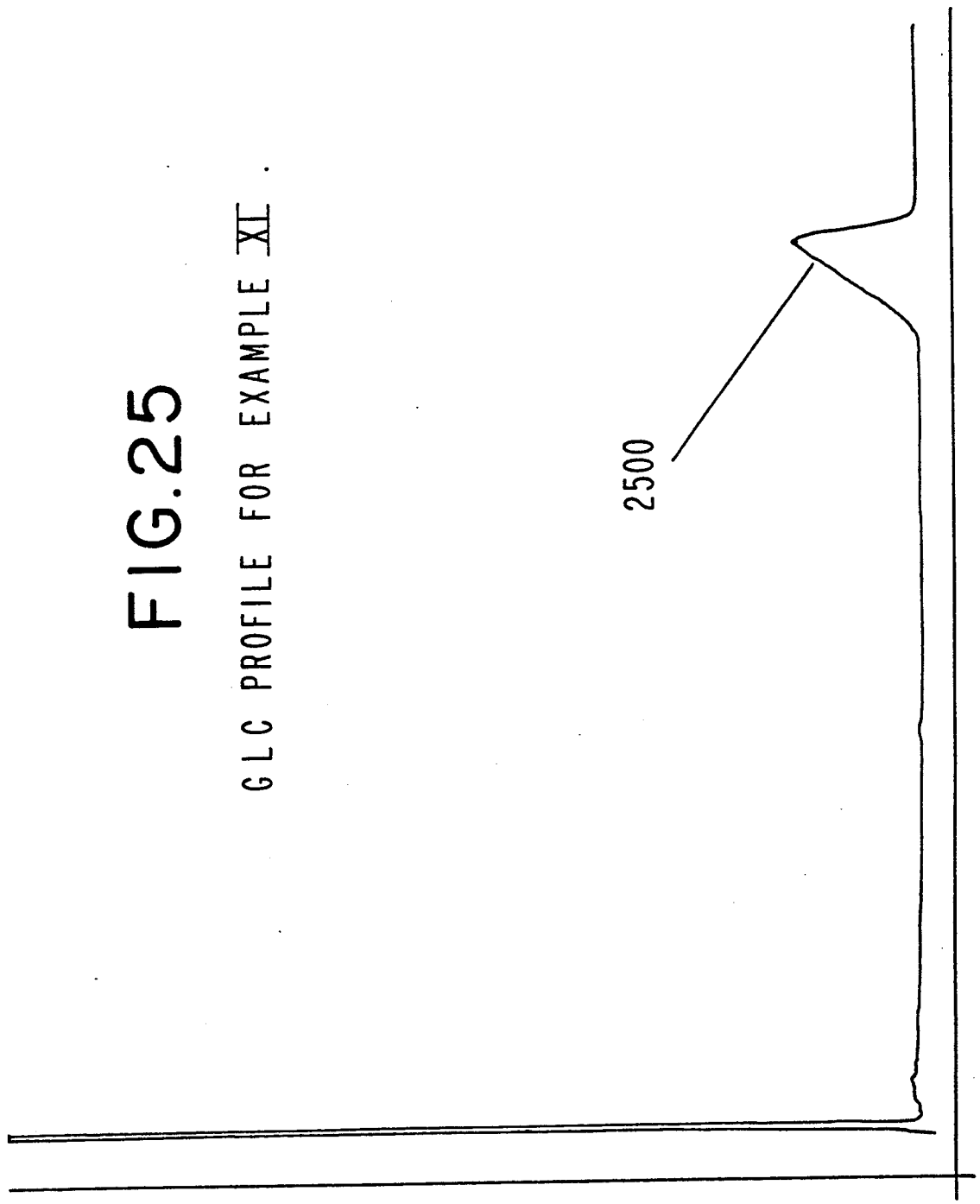

FIG. 25 is the GLC profile for the reaction product of Example XI containing the compound having the structure:

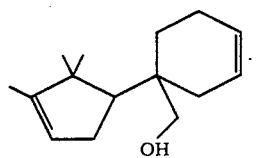

FIG. 26 is the NMR spectrum for the compound having the structure:

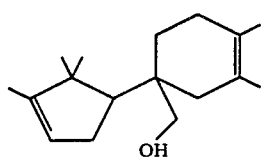

prepared according to Example XI.

FIGS. 26A, 26B and 26C are detailed sections of the NMR spectrum of FIG. 26.

Figure 27:
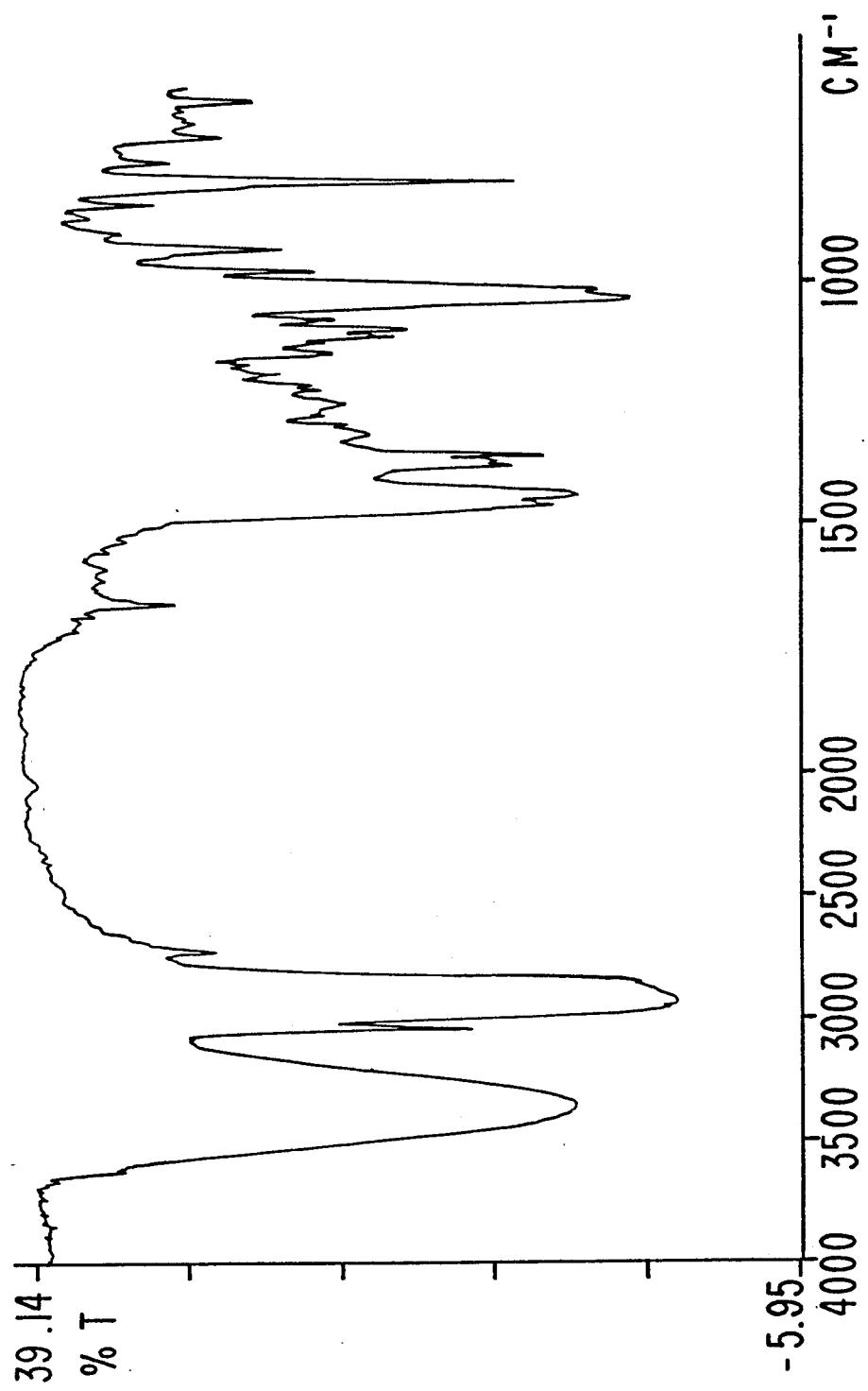

FIG. 27 is the infra-red spectrum for the compound having the structure:

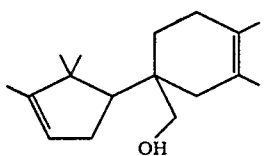

prepared according to Example XI.

Figure 28:
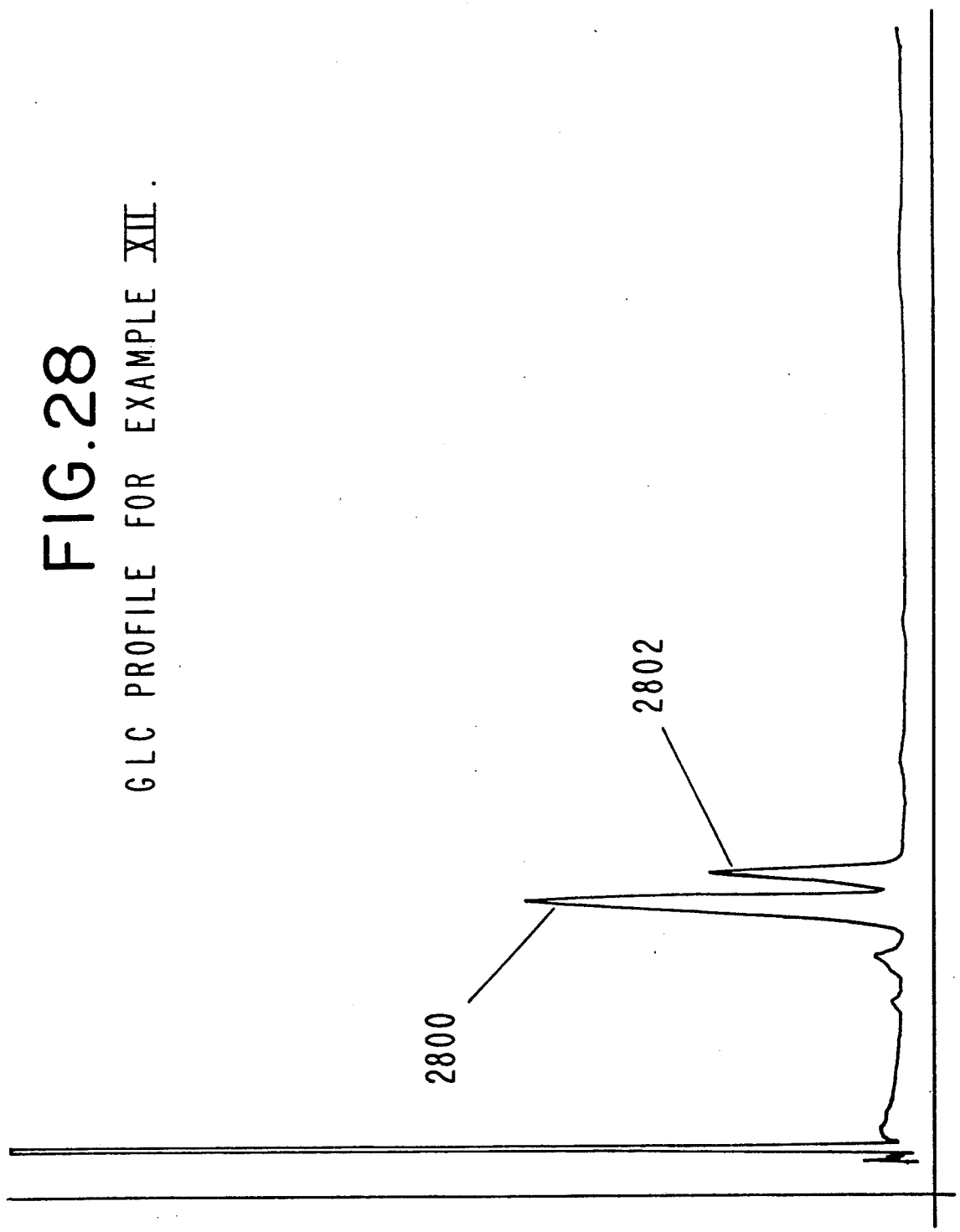

FIG. 28 is the GLC profile for the reaction product of Example XII containing the compounds having the structures:

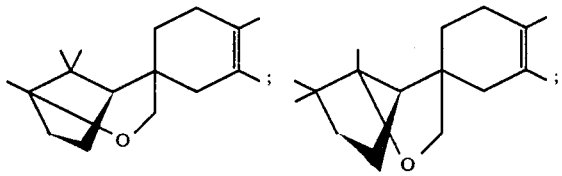

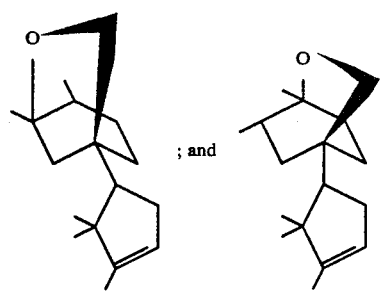

FIG. 29 is the NMR spectrum for the peak indicated by reference numeral 2802 of FIG. 28 for one or both of the compounds having the structures:

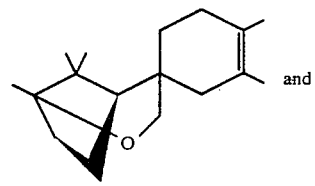

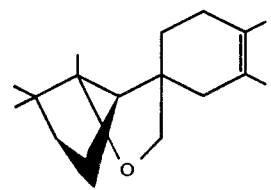

FIGS. 29A, 29B and 29C are detailed sections of the NMR spectrum of FIG. 29.

FIG. 30 is the infra-red spectrum for the peak indicated by reference numeral 2802 of FIG. 28 for one or both of the compounds having the structures:

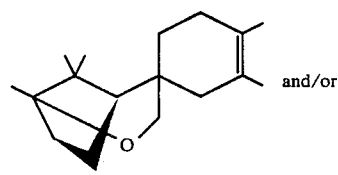

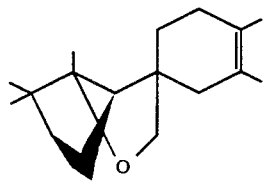

FIG. 31 is the NMR spectrum for the peak indicated by reference numeral 2800 of FIG. 28 for one or both of the compounds having the structures:

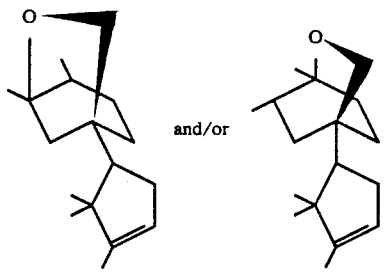
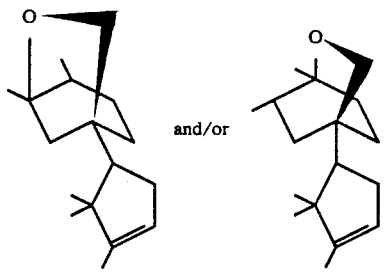

FIGS. 31A, 31B and 31C are detailed sections of the NMR spectrum of FIG. 31.

FIG. 32 is the infra-red spectrum for the peak indicated by reference numeral 2800 of FIG. 28 for one or both of the compounds having the structures:

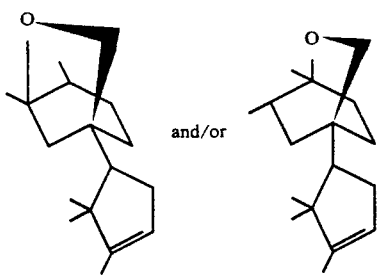

DETAILED DESCRIPTION OF THE DRAWINGS

Figure 1:
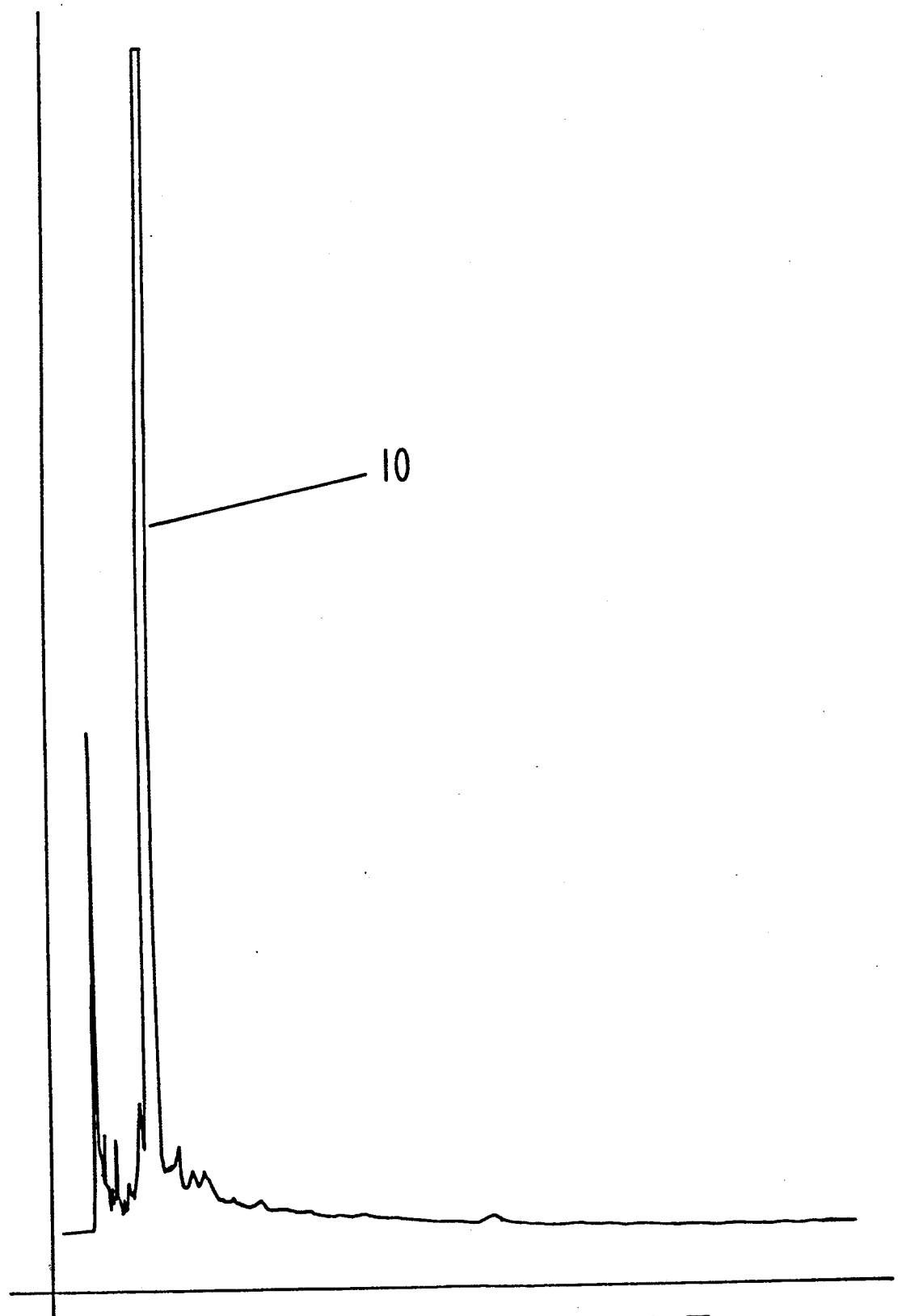
FIG. 1 is the GLC profile for the reaction product of Example I containing the compound having the structure.

FIG. 1 is the GLC profile for the reaction product of Example I containing the compound having the structure:

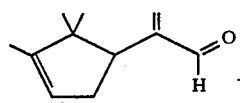

The peak indicated by reference numeral 10 is the peak for the compound having the structure:

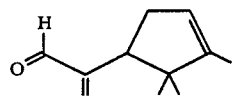

(Conditions: Carbowax column programmed at 220° C. isothermal).

FIG. 2 is the GLC profile for the reaction product of Example II containing the compounds having the structures:

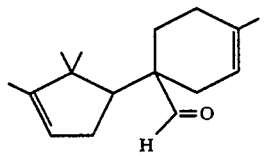

and

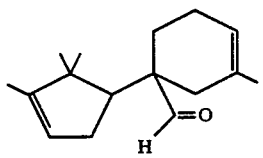

The group of peaks indicated by reference numeral 20 are peaks for isomers of the compounds having the structures:

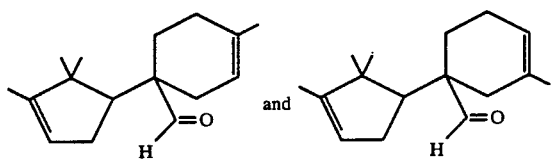

FIG. 4 is the GLC profile for the reaction product of Example III containing the compounds having the structures:

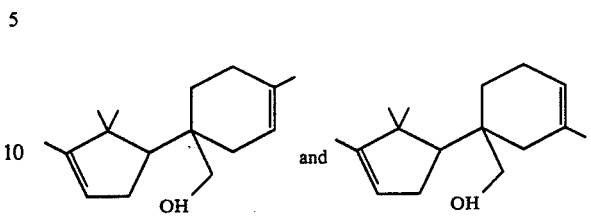

(Conditions: Carbowax column programmed at 150°-220° C.).

The peaks indicated by reference numerals 40, 42 and 44 are peaks for isomers of the compounds having the structures:

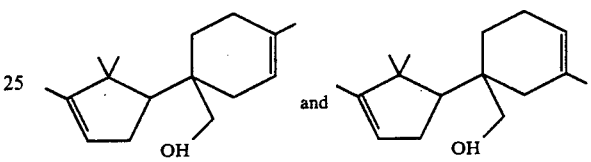

FIG. 6 is the NMR spectrum for the mixture of compounds having the structures:

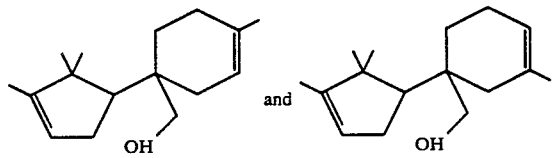

prepared according to Example III. Sections of the NMR spectrum indicated by the references 6A, 6B and 6C, respectively, are set forth in detail in FIGS. 6A, 6B and 6C.

FIG. 7 is the GLC profile for the reaction product of Example IV containing the compounds having the structures:

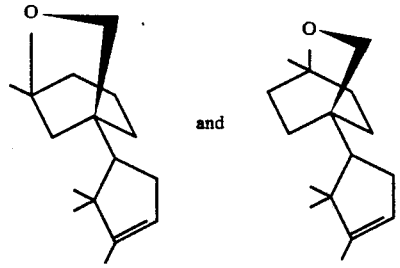

(Conditions: Carbowax column programmed at 220° C. isothermal).

The peaks indicated by reference numerals 70, 72 and 74 are peaks for isomers of the compounds having the structures:

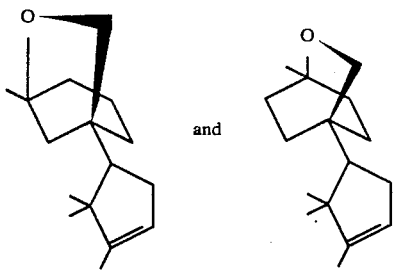

FIG. 10 is the GLC profile for the reaction product of Example V containing the compounds having the structures:

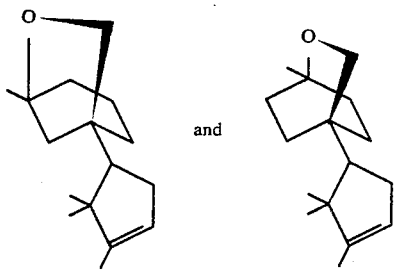

(Conditions: Carbowax column programmed at 200° C. isothermal).

The peaks indicated by reference numerals 100, 102, 104 and 106 are peaks for isomers or the compounds having the structures:

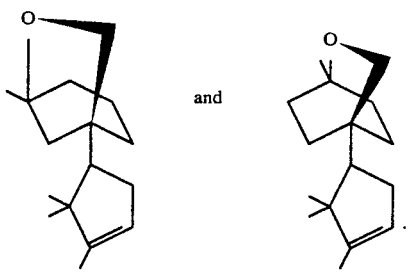

Referring to FIGS. 11 and 12, the apparatus used in producing polymeric fragrances containing at least one of the camphonyl spirocyclooxaoctane-containing compositions of our invention comprises a device for forming scented polyolefin (for example) pellets which comprises a vat or container 212 into which a mixture of polyolefins such as polyethylene or an aromatic substance or scented material containing or consisting of at least one of the camphonyl spirocyclooxaoctane-containing compositions of our invention is placed. The container is closed by an air tight lid 228 and clamped to the container by bolts 265. A stirrer 273 traverses the lid or cover 228 in air tight manner and is rotated in a suitable manner. A surrounding cylinder 212 having heating coils which are supplied with electric current through cable 224 from a rheostat or control 216 is operated to maintain the temperature inside the container 212 such that polyethylene or other thermoplastic polymer in the container will be maintained in a molten or liquid state. It has been found advantageous to employ a colorless, odorless polymer (e.g., polyethylene) with a viscosity ranging between 180 and 220 Saybolt seconds and having a melting point in the range of 220°-280° F. The heater 212-A is operated to maintain the upper portion of the container 212 within a temperature range of from 250°-350° F. The bottom portion of the container 212 is heated by means of heating coils 212-A heated through a control 220 connected thereto through a connecting wire 226 to maintain the lower portion of the container 212 within a temperature range of from 250°-350° F.

Thus, polymer (e.g. polyolefin) added to the container 212 is heated from 10-12 hours whereafter a scent or aroma imparting material which contains or consists of at least one of the camphonyl spirocyclooxaoctane-containing compositions of our invention is quickly added to the melt. The material must be compatible with the polyolefin and forms a homogeneous liquid melt therewith. The scented material containing or consisting of at least one of the camphonyl spirocyclooxaoctane-containing compositions of our invention is of a type for the particular aroma desired and formulated specifically for the scenting purpose for which the polyolefin will be employed. The heat resisting coils and aromatic materials in some instances in solid or powdered form may be employed or added to the polyolefin in the container 212. Generally about 10-30% by weight of the scenting material is added to the polyolefin.

After the scent imparting material containing or consisting of at least one of the camphonyl spirocyclooxaoctane-containing compositions of our invention is added to the container 212, the mixture is stirred for a few minutes, for example, 5-15 minutes and maintained within the temperature ranges indicated previously by the heating coils 212-A and 218, respectively. The controls 216 and 220 are connected through cables 224 and 226 to a suitable supply of electric current for supplying the power for heating purposes. The controls 216 and 220 are connected to the heating coils 212-A, respectively, through wires 214 and 222.

Thereafter, the valve "V" is opened permitting the mass to flow outwardly through conduit 232 having a multiplicity of orifices 234 adjacent to the lower side thereof. The outer end of the conduit 232 is closed so that the liquid polymer (e.g., polyolefin) and aroma imparting mixture (containing or consisting of at least one of the camphonyl spirocyclooxaoctane-containing compositions of our invention) will continuously drop through the orifices 234 downwardly from the conduit 232. During this time, the temperature of the polymer (e.g., polyolefin) and aroma mixture containing or consisting of at least one of the camphonyl spirocyclooxaoctane-containing compositions of our invention in the container 212 is accurately controlled so that a temperature in the range of from about 210°-275° F. will exist in the conduit 232. The regulation of the temperature through the control 216 and the control 220 is essential in order to insure temperature balance to provide for the continuous dropping or dripping of molten polymer (e.g. polyolefin) and scenting material containing or consisting of at least one of the camphonyl spirocyclooxaoctane-containing compositions of our invention through the orifices 234 at a rate which will insure the formation of droplets 236 which will fall downwardly onto a moving conveyor belt 238 trained to run between conveyor wheels 240 and 242 beneath the conduit 232.

When the droplets 236 fall onto the conveyor 238, they form pellets 244 which harden almost instantaneously and fall off the end of the conveyor 238 into a container 245 which is advantageously filled with water or some other suitable cooling liquid in order to insure the rapid cooling of each of the pellets. The pellets 244 are then collected from the container 245 and utilized in a process as illustrated infra.

A feature of this aspect of the process of our invention is in the provision for moistening the conveyor belt 238 to insure rapid formation of the solid polymer (e.g., polyolefin) scented pellets 244 without sticking to the belt. The belt 238 is advantageously of a material which will not normally stick to a melted plastic but the moistening means 248 insures a sufficiently cold temperature of the belt surface for the adequate formation of the pellets 244. The moistening means comprises a container 250 which is continuously fed with water 254 to maintain a level for moistening a sponge element 256 which bears against the exterior surface of the belt 238.

Referring to FIG. 13, FIG. 13 is the GLC profile for the reaction product of Example VII. The peak indicated by reference numeral 130 is the peak for the compound having the structure:

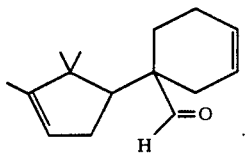

The peak indicated by reference numeral 132 is the peak for the starting material having the structure:

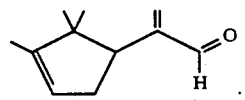

FIG. 14 is the NMR spectrum for the compound having the structure:

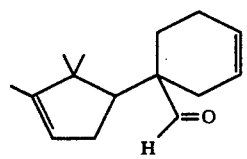

prepared according to Example VII. Sections of the NMR spectrum indicated by the references A, B and C, respectively, are set forth in detail in FIGS. 14A, 14B and 14C.

FIG. 15 is the GLC profile for the reaction product of Example VIII. The peak indicated by reference numeral 150 is the peak for the compound having the structure:

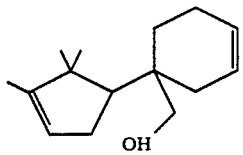

FIG. 16 is the NMR spectrum for the compound having the structure:

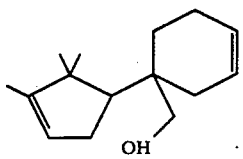

Sections of the NMR spectrum indicated by references A, B and C are set forth in detail in FIGS. 16A, 16B and 16C.

FIG. 17 is the GLC profile for the reaction product of Example IX. The peaks indicated by reference numerals 172 and 174 are peaks for one or both of the compounds having the structures:

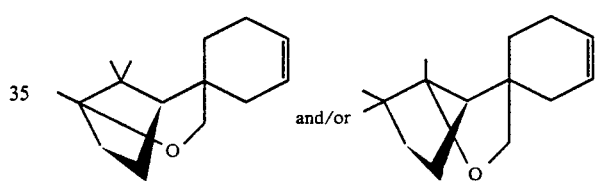

FIG. 18 is the NMR spectrum for the peak indicated by reference numeral 174 of FIG. 17. Sections of the NMR spectrum indicated by the references A, B and C, respectively, are set forth in detail in FIGS. 18A, 18B and 18C.

FIG. 20 is the NMR spectrum for the peak indicated by reference numeral 172 of FIG. 17. Sections of the NMR spectrum indicated by the references A, B and C, respectively, are set forth in detail in FIGS. 20A, 20B and 20C.

FIG. 22 is the GLC profile for the reaction product of Example X. The peak indicated by reference numeral 2200 is the peak for the compound having the structure:

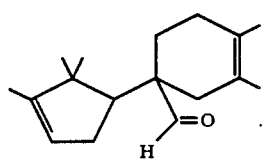

FIG. 23 is the NMR spectrum for the compound having the structure:

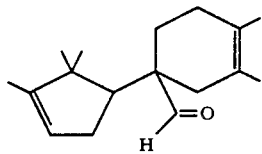

Sections of the NMR spectrum indicated by the references A, B and C, respectively, are set forth in detail in FIGS. 23A, 23B and 23C.

FIG. 25 is the GLC profile for the reaction product of Example XI containing the compound having the structure:

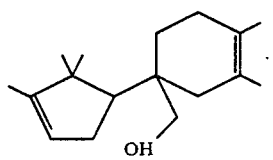

FIG. 26 is the NMR spectrum for the compound having the structure:

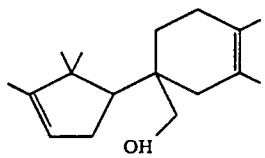

prepared according to Example XI. Sections of the NMR spectrum indicated by the references A, B and C, respectively, are set forth in detail in FIGS. 26A, 26B and 26C.

FIG. 28 is the GLC profile for the reaction product of Example XII. The peak indicated by reference numeral 2800 is the peak for one or both of the compounds having the structures:

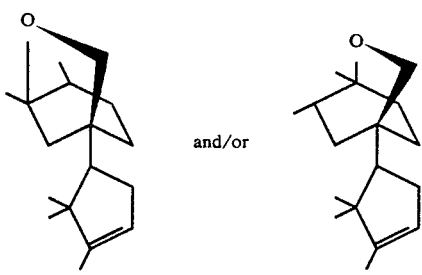

The peak indicated by reference numeral 2802 is the peak for one or both of the compounds having the structures:

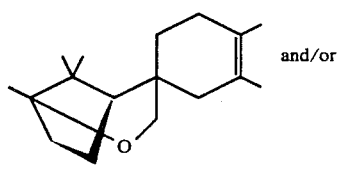

FIG. 29 is the NMR spectrum for the peak indicated by reference numeral 2802 FIG. 28 for one or both of the compounds having the structures:

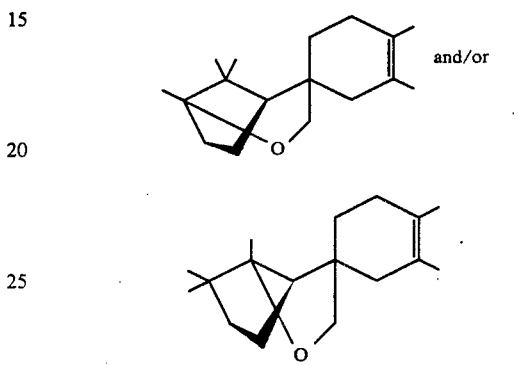

Sections of the NMR spectrum indicated by the references A, B and C, respectively, are set forth in detail in FIGS. 29A, 29B and 29C.

FIG. 31 is the NMR spectrum for the peak indicated by reference numeral 2800 of FIG. 28 for one or both of the compounds having the structures:

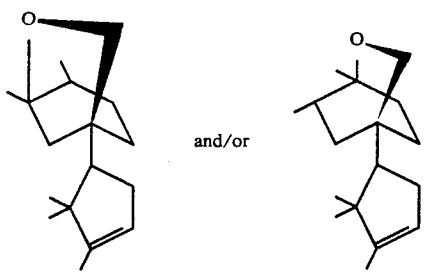

Sections of the NMR spectrum indicated by the references A, B and C, respectively, are set forth in detail in FIGS. 31A, 31B AND 31C.

THE INVENTION

The instant invention provides camphonyl spirocyclooxaoctane-containing compositions defined according to the generic structures:

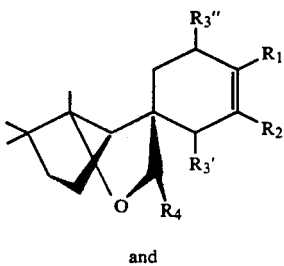

and

-continued

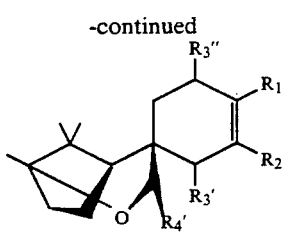

and mixtures containing compounds having the structures:

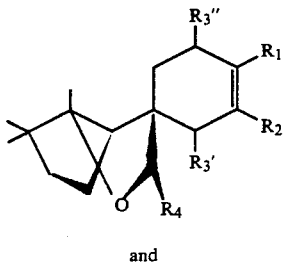

and

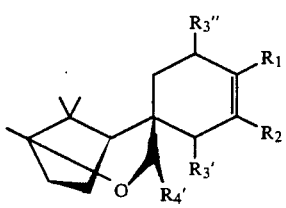

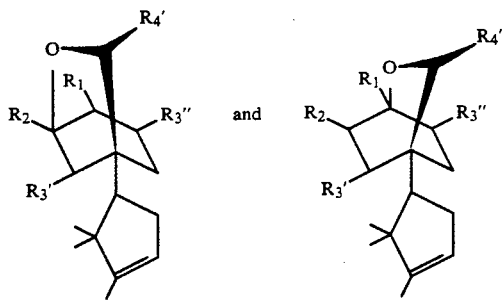

wherein $R_1$, $R_2$, $R_3'$, and $R_3''$ each represents hydrogen or methyl and $R_4$ is hydrogen or $C_1$-$C_5$ alkyl with the provisos:

(A) with regard to compounds defined according to the structures:

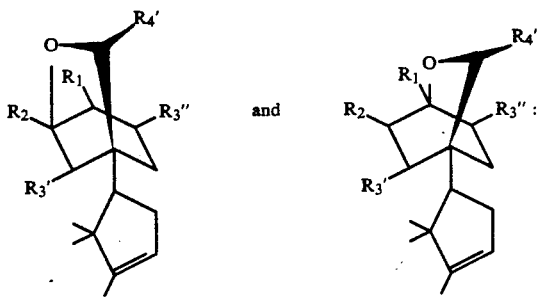

(i) one or two of $R_1$, $R_2$, $R_3'$, and $R_3''$ represents methyl;
(ii) $R_1$ and/or $R_2$ are methyl;

(iii) at least one or $R_3'$ and $R_3''$ is hydrogen; and
(iv) when $R_1$ or $R_2$ is methyl then each of $R_3'$ and $R_3''$ is hydrogen;

(B) with regard to the compounds defined according to the structures:

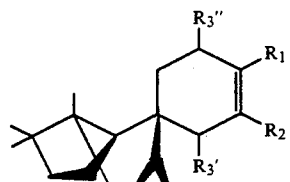

and

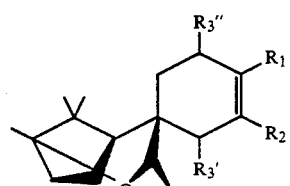

(i) at least one or $R_3'$ and $R_3''$ is hydrogen
(ii) when $R_1$ or $R_2$ is methyl then each of $R_3'$ and $R_3''$ is hydrogen.

The camphonyl spirocyclooxaoctane-containing compositions of our invention are useful in augmenting or enhancing the aroma of perfume compositions, colognes and perfumed articles (including but not limited to solid or liquid anionic, cationic, nonionic or zwitterionic detergents, perfumed polymers, fabric softener compositions and fabric softener articles, cosmetic powders, hair preparations and the like).

Briefly, our invention also employs the camphonyl spirocyclooxaoctane-containing compositions of our invention to impart, augment and/or enhance cassis, Black currant, piney, balsamic, animalic, camphoraceous, woody and/or pepper aromas with animalic, piney, fruity, camphoraceous, woody, peppery, balsamic, terpenic and/or cassis topnotes in or to perfume compositions, colognes and perfumed articles (e.g., solid or liquid anionic, cationic, nonionic or zwitterionic detergents, perfumed polymers, fabric softener compositions, fabric softener articles, hair preparations, cosmetic powders and the like).

Briefly, the camphonyl spirocyclooxaoctane-containing compositions of our invention may be prepared by first forming the compound having the structure:

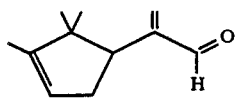

utilizing the reaction:

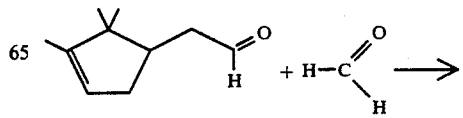

-continued

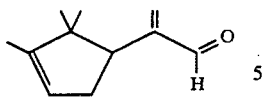

or using the reaction as set forth in U.S. Pat. No. 4,610,813 at reaction scheme "3" or "5" at columns 5 and 6 or at Example 4(f) at column 13, lines 32–53 and exemplified in Example I, infra.

The resulting compound having the structure:

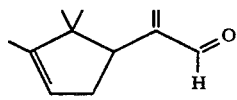

is then reacted with a diene defined according to the generic structure:

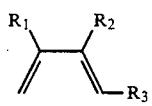

ps wherein $R_1$, $R_2$ and $R_3$ are the same or different methyl or hydrogen with the proviso that when $R_1$ and $R_2$ are both methyl then $R_3$ is hydrogen. The Diels-Alder reaction is shown, generically, according to the following reaction:

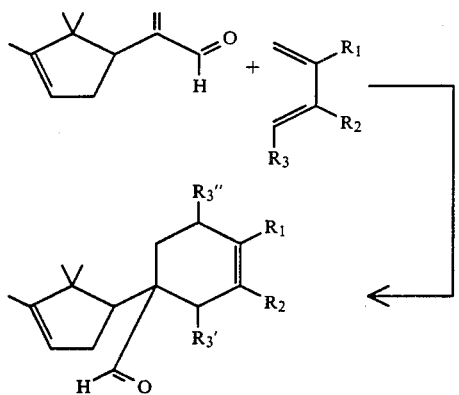

The resulting carboxaldehydes defined according to the generic structure:

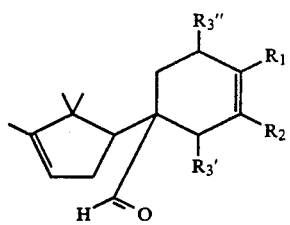

may be used "as is" for their organoleptic properties and thus they may be purified as by fractional distillation, or they may be further reacted by reduction to form the compounds defined according to the generic structure:

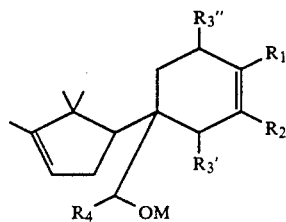

or they may be reacted via electrophilic addition to form the compounds defined according to the generic structure:

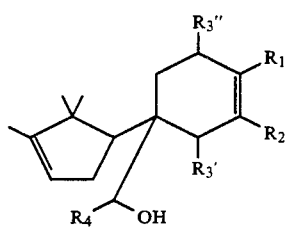

which compounds are further hydrolyzed to form the compounds defined according to the generic structure:

(wherein M represent MgX or Li and wherein X represents chloro, bromo or iodo). The reduction reaction is as follows:

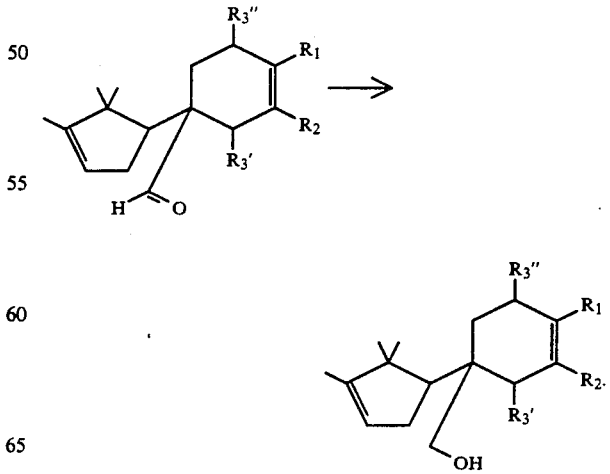

The electrophilic addition reactions are as follows:

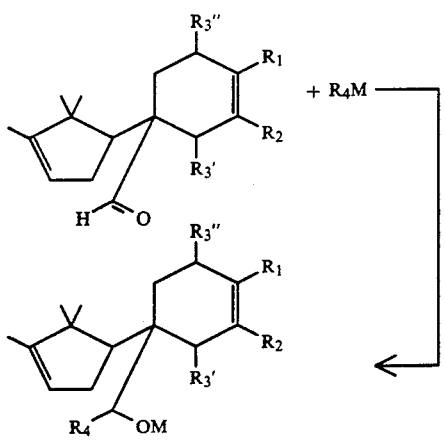

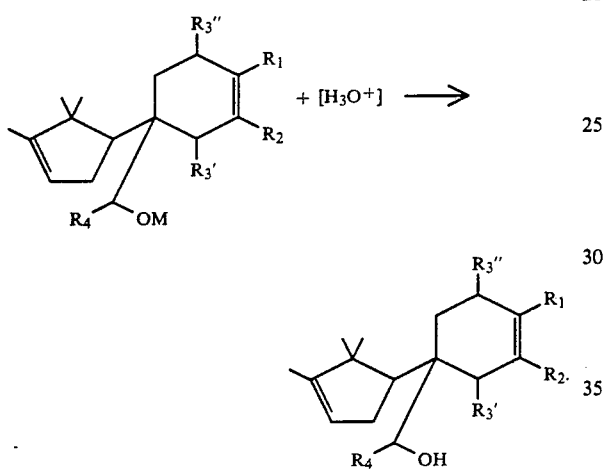

The resulting hydroxyl derivatives defined according to the generic structure:

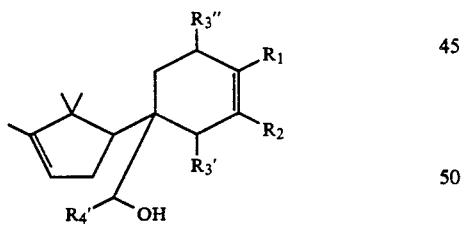

wherein R₄' represent hydrogen or $C_1$-$C_5$ alkyl may be used "as is" for their organoleptic properties (and thus fractionally distilled) or, in the situation wherein at least one of $R_1$ or $R_2$ is methyl, they may be further reacted by means of cyclization according to the reaction:

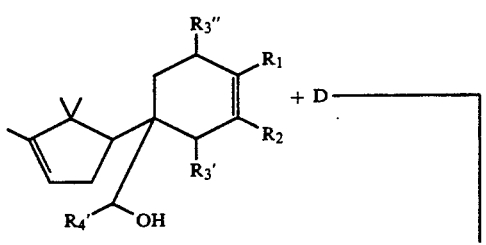

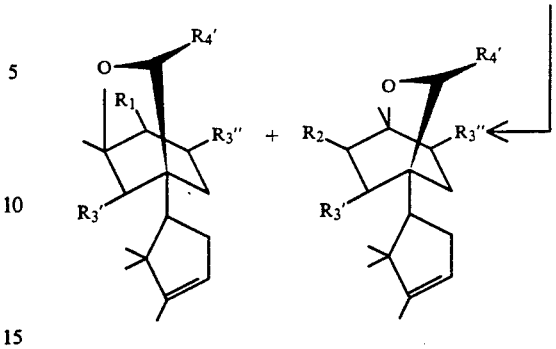

whereby the compounds having the structures:

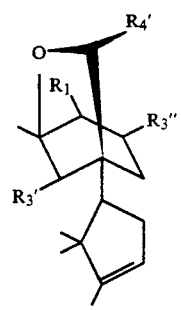

and

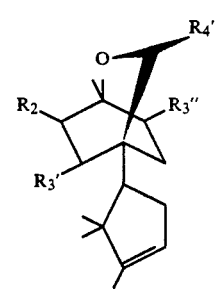

are formed in admixture with small amounts of compounds having the structures:

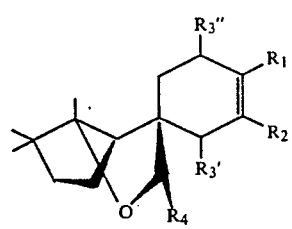

and

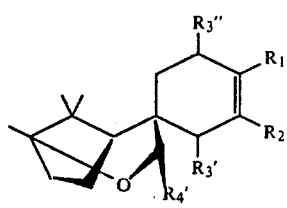

The compounds having the structures:

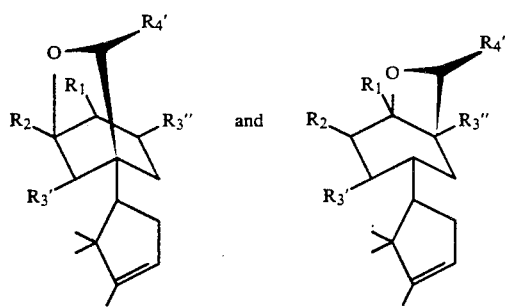 and in the case of where $R_1$ and $R_2$ are not both hydrogen or where at least one of $R_1$ or $R_2$ is methyl; can be further reacted with a material such as methane sulfonic acid to form additional quantities of the compounds having the structures:

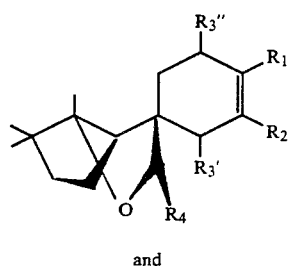

and

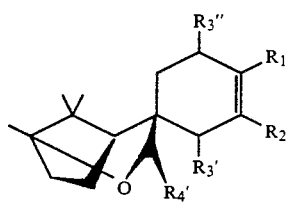

according to the reaction:

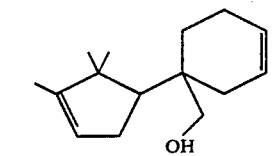

may be further reacted according to the reaction:

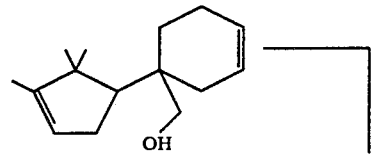

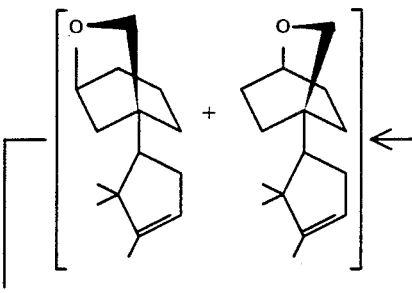

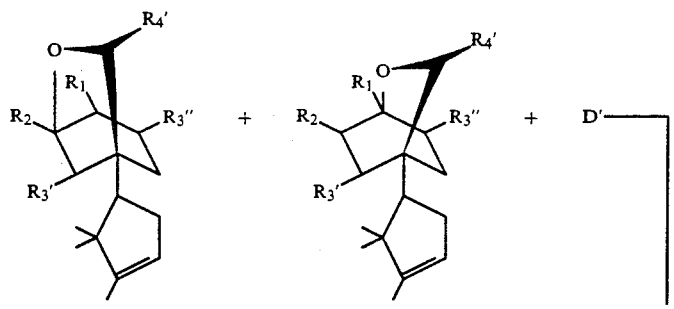

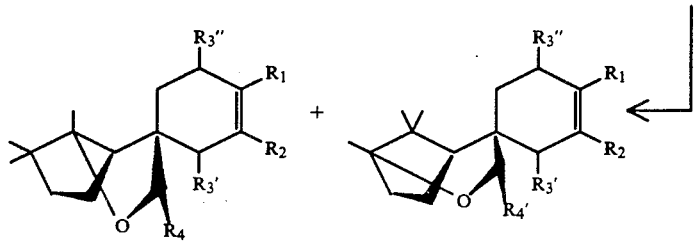

In the case where each of $R_1$, $R_2$, $R_3'$ and $R_3''$ are hydrogen, the compound having the structure:

-continued

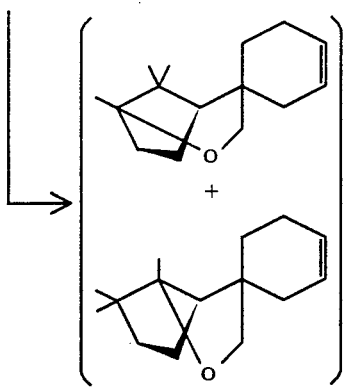

In this case, any intermediates that might be formed cannot be isolated, and the reaction goes completely to form the compounds having the structures:

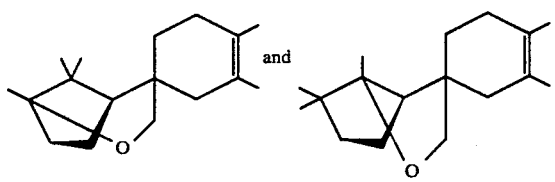

The above reaction sequences; that is, the Diels-Alder reaction; the alcohol formation reactions (either reduction or electrophilic addition) and the cyclization reactions are carried out using conditions substantially the same as those set forth in U.S. Pat. Nos. 4,269,862 and 4,267,067, the specifications for which are incorporated by reference herein. The conditions set forth in the above stated U.S. Pat. Nos. 4,269,862 and 4,267,067 are for the reaction schemes:

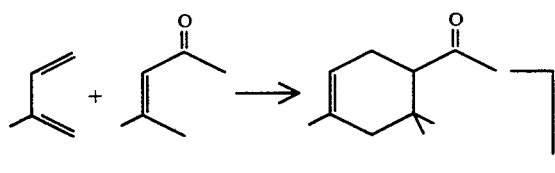

and

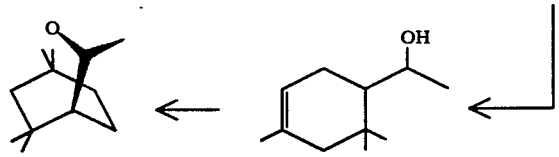

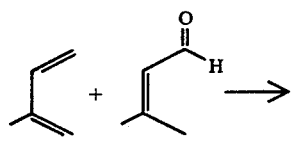

-continued

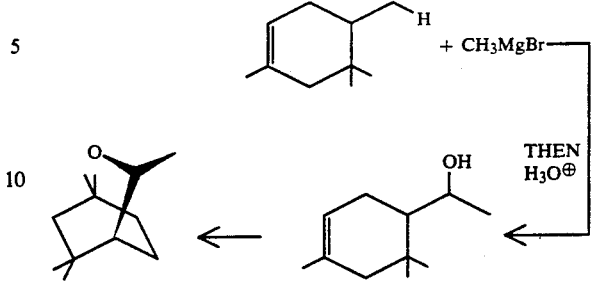

said conditions are set forth at column 5, lines 50–68, column 6, lines 1–62, column 7, lines 1–68 and column 8, lines 1–34 of U.S. Pat. No. 4,269,862 as well as column 5, lines 41–68, column 6, column 7 and column 8, lines 1–29 of U.S. Pat. No. 4,267,067.

Thus, the Diels-Alder reaction of the alpha, beta-unsaturated aldehyde defined according to the structure:

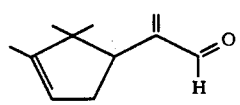

with the conjugated diene having the generic structure:

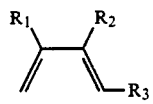

is, in general, a procedure known in the prior art. The reaction may be carried out in the presence of Lewis acid catalysts such as zinc chloride, aluminum chloride or aluminum bromide; or it may be carried out in the absence of catalysts at higher temperatures, e.g., up to 200° C. When carrying out the Diels-Alder reaction in the presence of catalysts lower temperatures, e.g. −10° C. up to 30° C. may be utilized. The Diels-Alder reaction may be carried out in the presence of or in the absence of a solvent. When solvents are used, it is preferred to use such solvents as xylene or tetralin.

It should be noted that when using Lewis acid catalyst such as zinc chloride, the isomer mix of aldehydes having the structure:

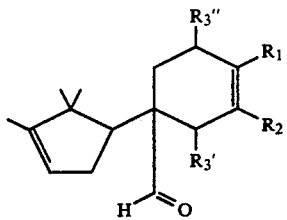

will be different from the isomer mix produced when carrying out the reaction in the absence of catalysts at higher temperature.

That part of the reaction sequence whereby the cyclohexene carboxaldehyde (the compounds defined according the genus:

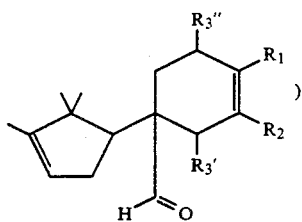

is reacted with the compound R-M (e.g., a Grignard reagent such as the $C_1$–$C_5$ alkyl magnesium halide or a $C_1$–$C_5$ alkyl lithium) to form the cyclohexene carbinol organometallic salt defined according the to the generic structure:

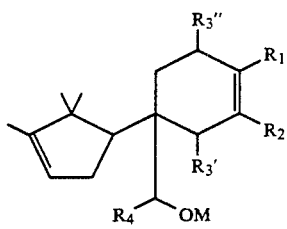

followed by hydrolysis of the cyclohexene carbinol organometallic salt to form the cyclohexene carbinol having the generic structure:

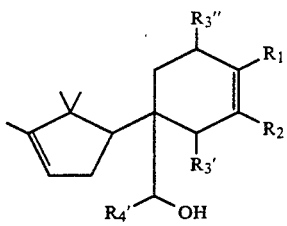

followed by cyclization of the resulting cyclohexene carbinol to form oxabicyclooctanes defined according to the generic structures:

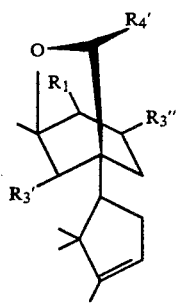

and

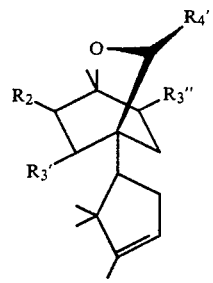

and small amounts of compound having the generic structures:

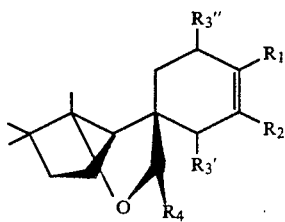

and

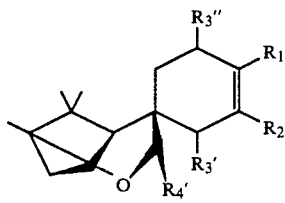

(wherein at least one of $R_1$ or $R_2$ is methyl) followed by additional cyclization of the resulting oxabicyclooctanes to form camphonyl spirocyclooxactane-containing compositions defined according to the generic structures:

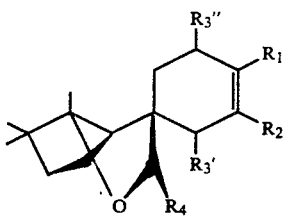

and

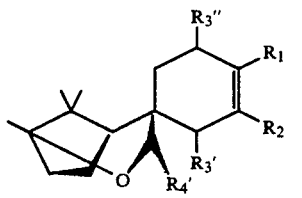

or in the case wherein each of $R_1$, $R_2$, $R_3'$ and $R_3''$ are hydrogen, where the cyclization of the resulting cyclohexene carbinol forms the compounds having the structures:

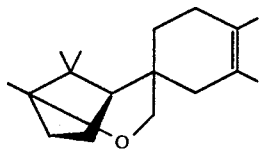

and

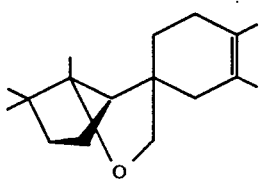

may be carried out either in one step or two steps.

In carrying out the "two-step reaction" whereby the cyclohexene carbinol is first isolated and then cyclized in the first step, that is, in the reaction of the compound R-M (e.g. a Grignard reagent) with the cyclohexene carboxaldehyde, the reaction of the R-M with the cyclohexene carboxaldehyde takes place in an ether solvent such as diethyl ether, tetrahydrofuran or di-n-butyl ether or another inert solvent such as toluene, chloroform to benzene to which two equivalents of ether has been added. The temperature of reaction preferably is between 0° and 100° C. with the most preferred temperature range for this reaction being from 35° C. up to 45° C.

In the two-step reaction, the resulting cyclohexene carbinol is then isolated as by distillation. The resulting cyclohexene carbinol is actually formed by means of hydrolysis of the organometallic salt defined according to the structure:

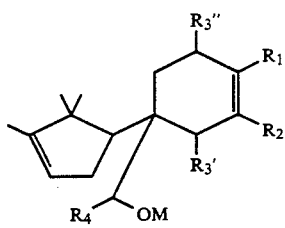

wherein M is MgX or Li and X is chloro,bromo or iodo.

In the two step reaction, the resulting cyclohexene carbinol evolved from the hydrolysis reaction is then isolated as by fractional distillation. The resulting cyclohexene carbinol is then cyclized at a temperature in the range of from 25° C. up to 150° C. in the presence of an acid such as methane sulfonic acid, aqueous hydrochloric acid or sulfuric acid or phosphoric acid. The acid may be used in combination with a polar solvent such as nitromethane, toluene, methylene dichloride, 1,2-dichloroethane, 1-nitropropane or 2-nitropropane. The cyclization in the alternative may be carried out using a Lewis Acid such as borontrifluoride, aluminum trichloride, zinc chloride, stannic chloride or zinc bromide in the presence of a solvent such as toluene, chloroform or xylene.

As stated above, the reaction of the cyclohexene carboxaldehyde to form the cyclohexene carbinol followed by cyclization may take place in a single reactor without separation of the cyclohexene carbinol. The conditions are the same as stated above for the two-step reaction.

When carrying out that part of the reaction sequence whereby the cyclohexene carboxaldehyde defined according to the generic structure:

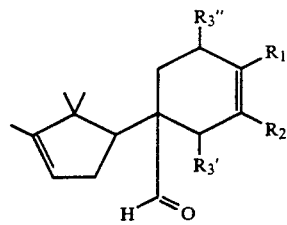

is reduced to form the compounds defined according to the generic structure:

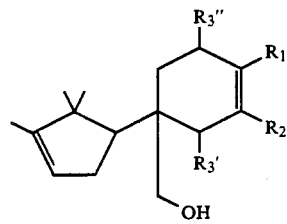

according to the reaction:

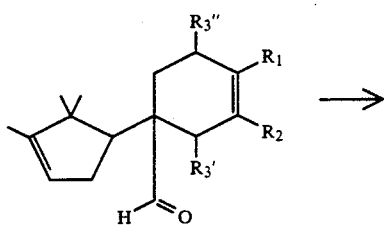

the reaction takes place in the presence of a solvent such as isopropanol, tetrahydrofuran, dioxane, diethyl ether, or diglyme using the reducing agent such as sodium borohydride, lithium aluminum hydride or VITRIDE ® (registered trademark for the compound having the structure:

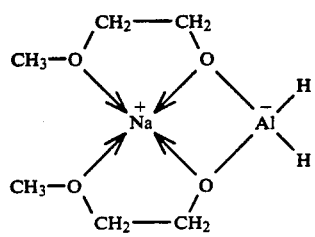

of the Hexcel Company).

In the reaction (in the case where at least one of $R_1$ or $R_2$ is methyl):

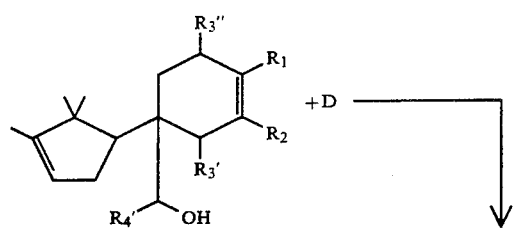 +D →

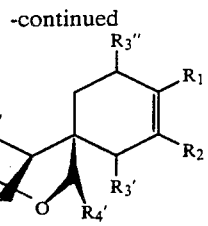

-continued are formed. The reaction however can proceed with additional time or at higher temperatures in the presence of a cyclization reagent such as methane sulfonic acid, sulfuric acid or xylene sulfonic acid or para-toluene sulfonic acid according to the reaction:

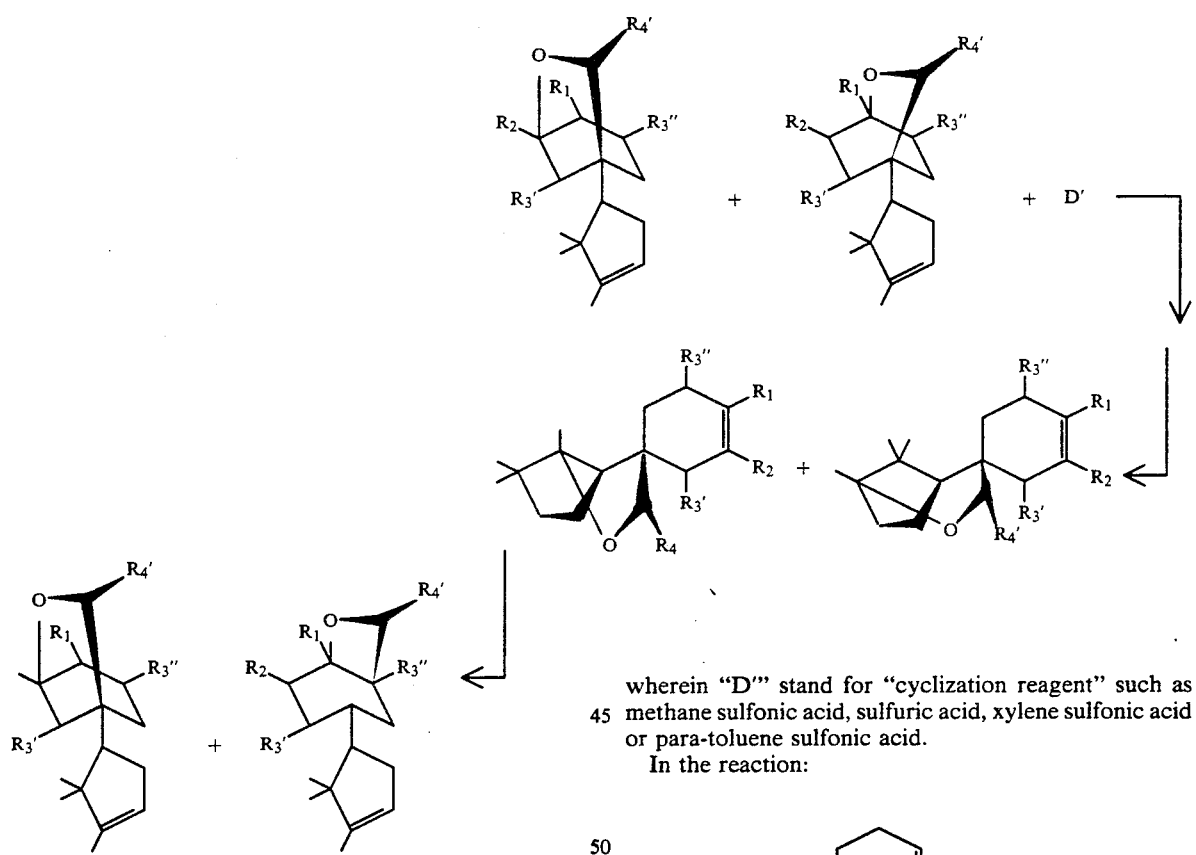

wherein "D'" stand for "cyclization reagent" such as methane sulfonic acid, sulfuric acid, xylene sulfonic acid or para-toluene sulfonic acid.

In the reaction:

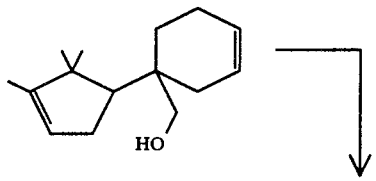

"D" stands for "cyclization reagent" such as methane sulfonic acid or sulfuric acid.

In this reaction wherein at least one of $R_1$ or $R_2$ is methyl, a small amount of compounds having the structures:

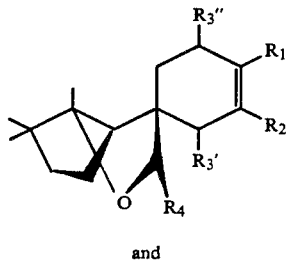

and

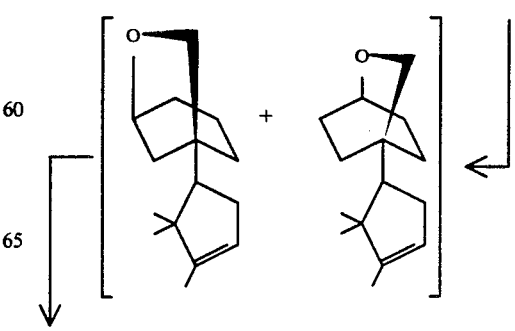

33
-continued

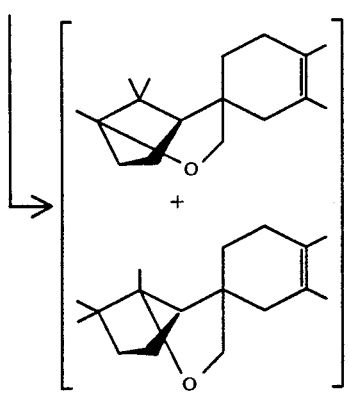

in actuality no intermediate has been isolated and the reaction proceeds directly, for example, when using methane sulfonic acid as follows:

34
-continued

The cyclization reagent used in this reaction may also be methane sulfonic acid, sulfuric acid, xylene sulfonic acid or para-toluene sulfonic acid.

The reactions, to wit:

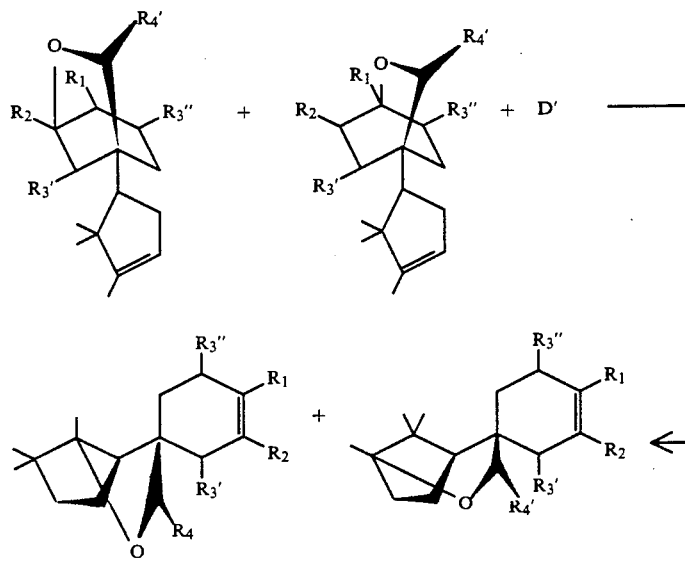

(when at least one of $R_1$ or $R_2$ is methyl) and the reaction:

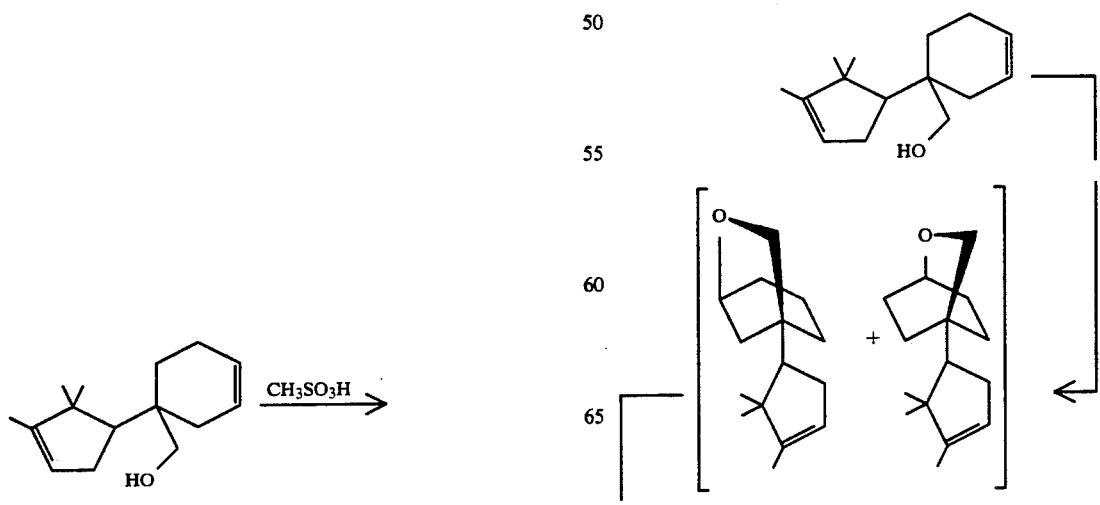

-continued

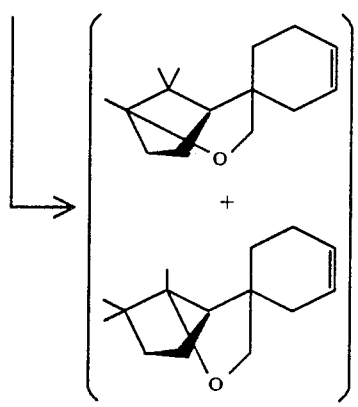

preferably takes place in the presence of a solvent such as nitroethane. The percent sulfonic acid catalyst or Lewis acid catalyst (which may also be used) may vary from about 1% up to about 5% by weight of the compound having the structure:

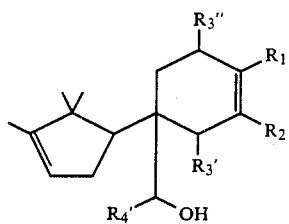

The concentration of reactant having the structure:

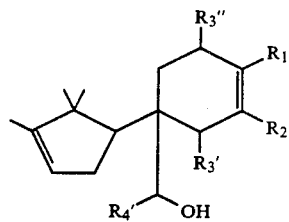

in the reaction mass may vary from about 1 mole per liter up to about 6 moles per liter. The reaction temperature may vary from about 50° C. up to about 80° C. The reaction time may vary from about 2 hours up to about 20 hours.

The following table sets forth specific products produced according to the invention of application for U.S. Letters Patent, Ser. No. 588,825 filed on Sep. 27, 1990 and their perfumery properties.

TABLE I

| Product Identification | Perfumery Properties |
|---|---|
| Mixture of compounds having the structures:<br><br>prepared according to Example V, bulked distillation fractions 9-17. | A cassis, camphoraceous, sweaty, borneol aroma with parsley, basil, cassis, sweaty, borneol-like, camphoraceous and eucalyptus bud-like topnotes. |
| Mixture of compounds having the structures:<br><br>and<br><br>prepared according to Example IV, bulked distillation fractions 6-8. | A cassis, woody and piney aroma with hemlock, piney, and cassis topnotes. |

The following Table II sets forth specific products produced according to our invention and their perfumery properties:

TABLE II

| Product Identification | Perfumery Properties |
|---|---|
| Mixture of compounds having the structures: [structure] and [structure] produced according to Example IX, bulked distillation fractions 3-6. | A cassis, Black currant, piney and balsamic aroma, with animalic, piney, fruity, camphoraceous, woody, peppery and balsamic topnotes. |
| Mixture of compounds having the structures: [structure] [structure] [structure] and [structure] prepared according to Example XII, bulked distillation fractions 3-10. | A cassis, animalic, camphoraceous, woody and peppery aroma, with cassis and terpenic topnotes. |

At least one of the camphonyl spirocyclooxaoctane-containing compositions of our invention and one or more auxiliary perfume ingredients including, for example, alcohols, aldehydes, ketones, terpenic hydrocarbons, esters, lactones, ethers (other than the ethers of our invention), natural essential oils and synthetic essential oils may be admixed so that the combined odors of the individual components produce a pleasant and desired fragrance, particularly and preferably in the cassis and pine fragrance areas. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling fresh smelling materials.

In perfume compositions, it is the individual components which contribute to their particular olfactory characteristics, however, the over-all sensory effect of the perfume composition will be at least the sum total of the effects of each of the ingredients. Thus, at least one of the camphonyl spirocyclooxaoctane-containing compositions of our invention can be used to alter, modify or enhance the aroma characteristics of a perfume composition, for example, by utilizing or moderating the olfactory reaction contributed by another ingredient in the composition.

The amount of one or more of the camphonyl spirocyclooxaoctane-containing compositions of our invention which will be effective in the perfume compositions as well as in the perfume articles and colognes depends on many factors including the other ingredients, their amounts and the effects which are desired. It has been found that perfume compositions containing as little as 0.01% of at least one of the camphonyl spirocyclooxaoctane-containing compositions of our invention and even less (e.g. 0.005%) can be used to impart, augment or enhance cassis, Black currant, piney, balsamic, animalic, camphoraceous, woody and pepper aromas with animalic, piney, fruity, camphoraceous, woody, peppery, balsamic, terpenic and cassis topnotes to soaps, cosmetics, solid or liquid anionic, cationic, nonionic or zwitterionic detergents, fabric softener compositions, fabric softener articles, hair preparations and perfumed polymers. The amount employed can range up to 70% of the fragrance components and will depend on considerations of cost, nature of the end product, the effect desired on the finished product and the particular fragrance sought.

One or more of the camphonyl spirocyclooxaoctane-containing compositions of our invention are useful (taken alone or together with other ingredients in perfume compositions) as (an) olfactory component(s) in detergents and soaps, space odorants, and deodorants, perfumes, colognes, toilet water, bath preparations such as creams, deodorants, hand lotions and sun screens; powders such as talcs, dusting powders, face powders and the like. When used as (an) olfactory component(s) as little as 1% of at least one of the camphonyl spirocyclooxaoctane-containing compositions of our invention or even less will suffice to impart intense and substantive cassis, Black currant, piney, balsamic, animalic, camphoraceous, woody and pepper aromas, with animalic, piney, fruity, camphoraceous, woody, peppery, balsamic, terpenic and cassis topnotes to pine formulations and to cassis formulations. Generally, no more than 20% of at least one of the camphonyl spirocyclooxaoctane-containing compositions of our invention based on the ultimate end product is required in the perfume composition.

Accordingly, in perfume compositions and colognes from about 0.01% up to about 70% of the perfume compositions may be at least one of the camphonyl spirocyclooxaoctane-containing compositions of our invention. In perfumed articles, the quantity of at least one of the camphonyl spirocyclooxaoctane-containing compositions of our invention in a perfumed article may vary from about 0.005% up to about 25% by weight of the perfumed article, in the case of perfumed polymers, for example; and up to about 8% by weight of the perfumed article in the case of solid or liquid anionic, cationic, nonionic or zwitterionic detergents, for example.

In addition, the perfume composition or fragrance composition of our invention can contain a vehicle or carrier for at least one of the camphonyl spirocyclooxaoctane-containing compositions of our invention. The vehicle can be a liquid such as a non-toxic alcohol such as ethyl alcohol or a non-toxic glycol such as propylene glycol or the like. The carrier can also be an absorbent solid, such as a gum (e.g., gum arabic, xanthan gum, or guar gum or mixtures of same) or components for encapsulating the composition (such as gelatin as by means of coacervation or such as a urea-formaldehyde prepolymer when a polymeric wall is intended to be formed around a liquid perfume composition center).

The following Examples I-XII serve to illustrate processes for preparing the camphonyl spirocyclooxaoctane-containing compositions of our invention. Examples following Example XII (Example XIII, et seq) illustrate organoleptic utilities of the camphonyl spirocyclooxaoctane-containing compositions of our invention.

All parts and percentages given herein are by weight unless otherwise specified.

EXAMPLE I
PREPARATION OF ALPHA-METHYLENE CAMPHOLENIC ALDEHYDE

Reaction:

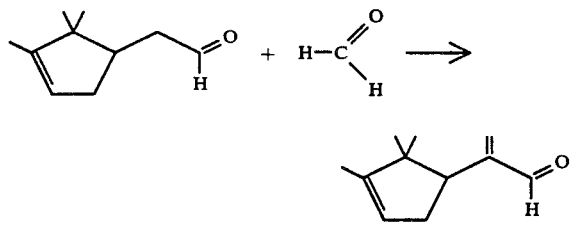

Into a twelve liter Morton flask equipped with stirrer, thermometer, reflux condenser, heating mantle, and addition funnel are placed 89 grams (0.69 moles) of di-n-butyl amine and 42 grams (0.69 moles) of acetic acid. The resulting reaction mass temperature rises to 50° C. (as a result of salt formation to form di-n-butyl amine acetate). The reaction mass is cooled to 38° C. and rapidly, 1600 grams (19.74 moles) of 37% formaldehyde (effective weight 592 grams) is added to the reaction mass.

The reaction mass is heated to 70° C. While maintaining the reaction temperature at between 70° and 72° C., over a period of 5 hours, 2000 grams (13.2 moles) of campholenic aldehyde is added to the reaction mass. The reaction mass is then stirred for an additional period of 8 hours while maintaining the reaction mass at 70° C.

The reaction mass now exists in two phases; an organic phase and an aqueous phase. The organic phase is washed with 2 liters of water followed by saturated sodium chloride; followed by 500 ml 10% sodium bicarbonate followed by 1000 ml saturated sodium chloride.

The organic phase is filtered through anhydrous magnesium sulfate and rushed over to yield 1601 grams of product. The resulting product is then fractionally distilled yielding the following fractions:

| Fraction No. | Vapor Temp. (°C.) | Liquid Temp. (°C.) | Vacuum mm/Hg. Pressure | Weight of Fraction |
|---|---|---|---|---|
| 1 | 48/80 | 78/89 | 3.72/4.22 | 655 |
| 2 | 78 | 97 | 3.56 | 691 |
| 3 | 94 | 160 | 3.20 | 391 |
| 4 | 110 | 163 | 2.42 | 15. |

FIG. 1 is the GLC profile of the reaction product. The peak indicated by reference numeral 10 is the peak for the compound having the structure:

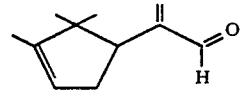

(Conditions: Carbowax column programmed to 200° C. isothermal).

EXAMPLE II
PREPARATION OF FORMYL CYCLOPENTENYL CYCLOHEXENE

Reaction:

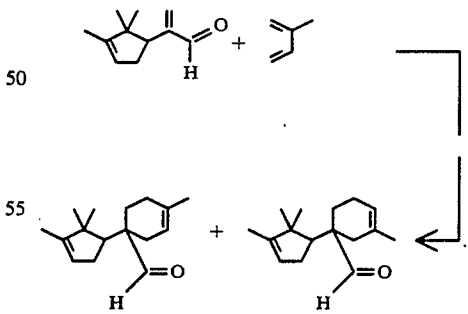

Into a two liter Parr Bomb is charged 590 grams (3.73 moles) of the compound having the structure:

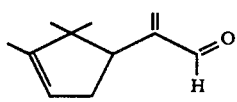

prepared according to Example I and 305 grams (4.48 moles) of isoprene having the structure:

The Parr Bomb is closed and the temperature is raised to 140° C. and the pressure is raised to 180 psig. The Parr Bomb is maintained a 140° C. at 180 psig for a period of 0.5 hours. The bomb is then heated to 170° C. while maintaining the pressure at 180 psig and maintained at that temperature and pressure for 12 hours. The Parr Bomb is then cooled and opened and the resulting product is fractionally distilled on an 18 inch×1.5 inch Goodloe distillation column yielding the following fractions:

| Fraction No. | Vapor Temp. (°C.) | Liquid Temp. (°C.) | Vacuum mm/Hg. Pressure | Reflux Ratio |
| --- | --- | --- | --- | --- |
| 1 | 60/140 | 145/150 | 0.895/0.72 | 9/1 |
| 2 | 128 | 145 | 0.69 | 9/1 |
| 3 | 128 | 146 | 0.685 | 9/1 |
| 4 | 127 | 148 | 0.740 | 9/1 |
| 5 | 128 | 148 | 1.0 | 9/1 |
| 6 | 128 | 145 | 0.978 | 2/1 |
| 7 | 148 | 152 | 0.918 | — |
| 8 | 141 | 149 | 0.918 | 2/1 |
| 9 | 122 | 147 | 0.984 | 2/1 |
| 10 | 113 | 145 | 0.972 | 2/1 |
| 11 | 112 | 147 | 0.954 | 2/1 |
| 12 | 110 | 155 | 0.954 | 2/1 |
| 13 | 109 | 178 | 0.960 | 2/1 |
| 14 | 95 | 200 | 0.960 | 2/1 |
| 15 | 95 | 210 | 0.918 | 2/1. |

Fractions 8, 9 and 10 are bulked. The bulked fractions 8, 9 and 10 have a green, ozoney and piney aroma profile. The resulting product is a mixture of compounds having the structures:

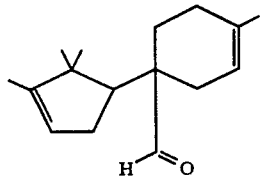

and

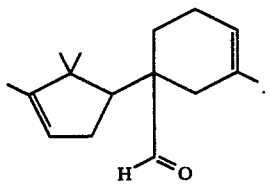

FIG. 2 is the GLC profile for the reaction product. The peaks indicated by reference numeral 20 are the peaks for the compounds having the structures:

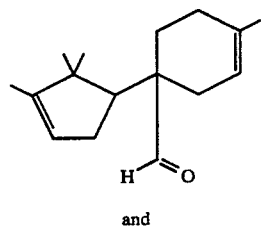

and

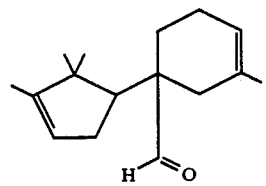

and isomers thereof. (Conditions: Carbowax column programmed at 220° C. isothermal).

FIG. 3 is the NMR spectrum for the mixture of compounds having the structures:

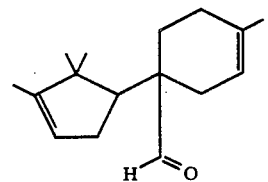

and

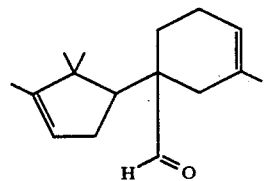

EXAMPLE III

PREPARATION OF CYCLOPENTENYL HYDROXYMETHYL CYCLOHEXENE DERIVATIVE

Reaction:

-continued

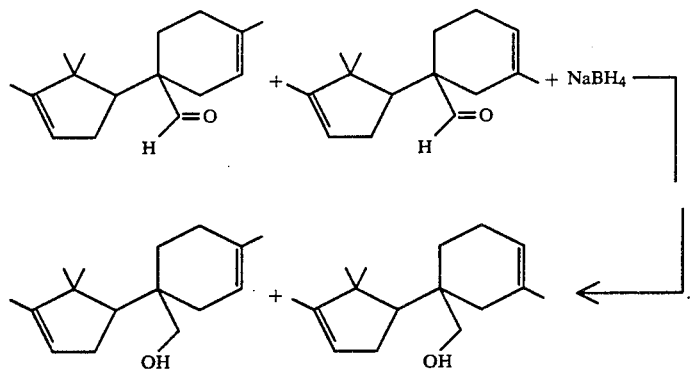

Into an one liter reaction flask equipped with stirrer, thermometer, reflux condenser, heating mantle and addition funnel is placed 19 grams (0.50 moles) of sodium borohydride and a mixture of 200 ml isopropyl alcohol and 150 ml water. The resulting mixture with stirring is maintained at 24° C. While maintaining the resulting mixture at 24° C., the mixture of compounds having the structures:

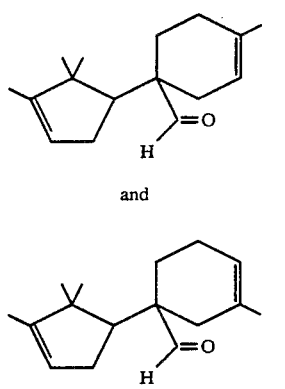

prepared according to Example II is added to the reaction mass (230 grams, 0.99 moles) over a period 2 hours. The temperature is allowed to rise to 472° C.

The reaction mass is then aged for a period of 6.5 hours while it cools to room temperature on its own.

The reaction mass now exists in two phases; an organic phase and an aqueous phase. The aqueous phase is drawn off and the organic phase is washed with 400 ml saturated sodium chloride and then filtered through anhydrous magnesium sulfate. The reaction mass is then concentrated to yield 225 grams of crude product (0.96 moles, 97%).

FIG. 4 is the GLC profile for the reaction product containing the compounds having the structures:

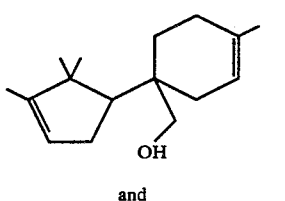

and

-continued

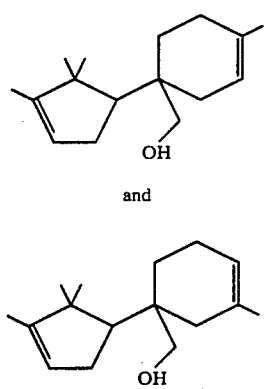

(Conditions: Carbowax column programmed at 150°-220° C.). The peaks indicated by reference numerals 40, 42 and 44 are the peaks for the isomers of the compounds having the structures:

FIG. 5 is the infra-red spectrum for the mixture of compounds having the structures:

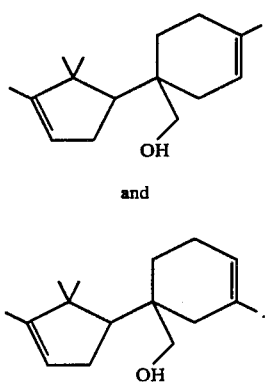

FIG. 6 is the NMR spectrum for the mixture of compounds having the structures:

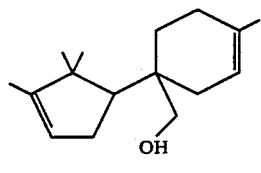

and

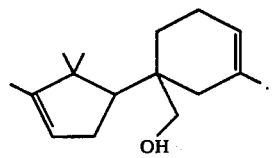

The sections of the spectrum marked in detail as "6-A", "6-B" and "6-C" are shown in detail in FIGS. 6-A, 6-B and 6-C.

EXAMPLE IV

PREPARATION OF OXABICYCLOOCTANE DERIVATIVE

Reaction:

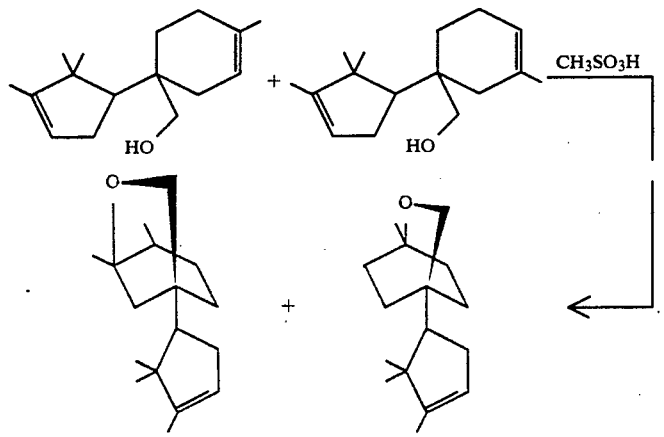

Into an one liter reaction flask equipped with stirrer, thermometer, reflux condenser, heating mantle and addition funnel is placed 225 grams (0.96 moles) of the mixture of the compounds having the structures:

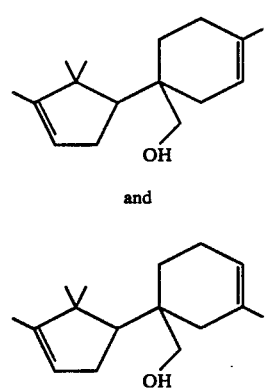

prepared according Example III and 300 ml of nitromethane. The reaction mass is maintained at 25°-26° C. Slowly over a period of 5 minutes, 2.76 grams (0.028 moles) of methane sulfonic acid is added to the reaction mass.

The reaction mass, with stirring is then heated to 60° C. and maintained at 60° C. for a period of 5 hours. At the end of the 5 hour period 200 ml of 10% sodium bicarbonate is added to the reaction mass. The reaction mass is then stirred for an additional 30 minutes. The reaction mass is then aged for 72 hours. At the end of the 72 hours period, 250 ml water followed by 50 ml toluene is added to the reaction mass. The organic phase is separated from the aqueous phase and the organic phase is washed with 250 ml of saturated sodium chloride. The reaction mass is then filtered through anhydrous magnesium sulfate and rushed over to yield 165 grams (0.71 moles) of product (73% yield). The reaction mass is then fractionally distilled yielding the following fractions:

| Fraction No. | Vapor Temp. (°C.) | Liquid Temp. (°C.) | Vacuum mm/Hg. Pressure |
|---|---|---|---|
| 1 | 32/45 | 45/93 | 105/267 |
| 2 | 110 | 738 | 2.87 |
| 3 | 126 | 740 | 2.52 |
| 4 | 130 | 140 | 2.67 |
| 5 | 130 | 142 | 2.56 |
| 6 | 132 | 143 | 2.63 |
| 7 | 134 | 144 | 2.76 |
| 8 | 134 | 146 | 2.76 |
| 9 | 134 | 153 | 2.76 |
| 10 | 131 | 162 | 2.87 |
| 11 | 132 | 173 | 2.70 |
| 12 | 110 | 233 | 3.10. |

FIG. 7 is the GLC profile for the reaction product prior to distillation containing the compounds having the structures:

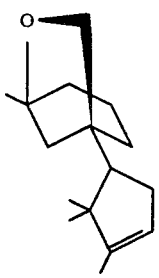

and

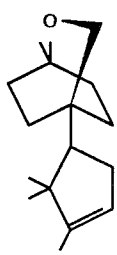

(Conditions: Carbowax column programmed at 220° C. isothermal). The peaks indicated by reference numerals 70, 72 and 74 are for the compounds and their isomers having the structures:

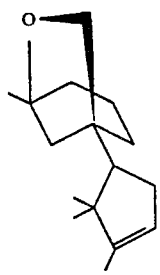

and

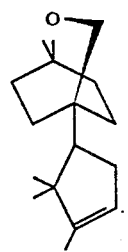

FIG. 8 is the infra-red spectrum for the mixture of compounds having the structures:

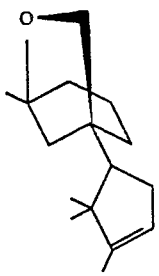

and

FIG. 9 is the NMR spectrum for the mixture of compounds having the structures:

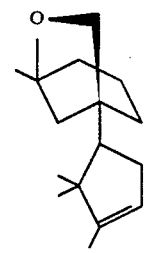

and

Both distillation fractions 6–8 having a cassis, woody and piney aroma with hemlock, piney and cassis topnotes.

EXAMPLE V

PREPARATION OF OXABICYCLOOCTANE DERIVATIVE

Reaction:

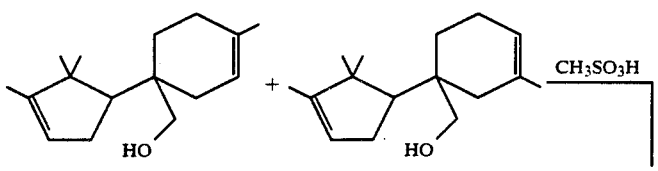

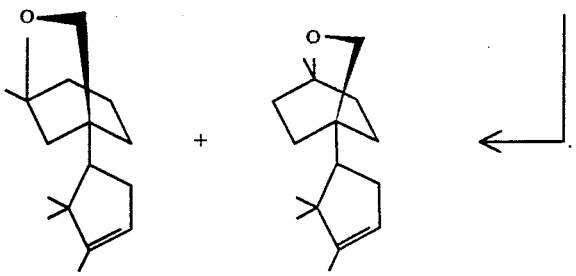

-continued

Into a three liter reaction flask equipped with stirrer, thermometer, reflux condenser and additional funnel is placed 660 grams (2.82 moles) of the mixture of compounds having the structures:

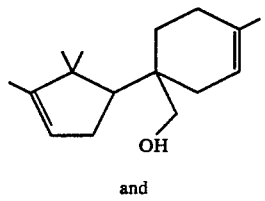

and

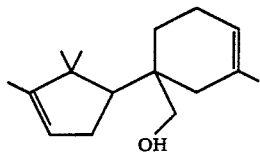

prepared according to the procedure of Example III and 600 ml of nitromethane. While maintaining the reaction temperature at 34° C., 13.50 grams (0.14 moles) of methane sulfonic acid is added to the reaction mass. The reaction mass is then heated to 60° C. and maintained at 60° C. with stirring for a period of 5.5 hours. At the end of the 5.5 hour period, 600 ml, 10% sodium bicarbonate is added to the reaction mass and the reaction mass is stirred for a period of 0.5 hours at 60° C. The reaction mass then partitions into three layers upon cooling. The aqueous phase is drawn off as is the nitromethane phase. The aqueous phase is extracted with 100 ml diethyl ether. The organic phase and the diethyl ether extract are combined and washed with 500 ml saturated sodium chloride; and then dried over anhydrous magnesium sulfate and filtered and concentrated to 593 grams (2.53 moles). The resulting product is distilled yielding 477 grams of product (2.04 moles) and yielding the following fractions:

| Fraction No. | Vapor Temp. (°C.) | Liquid Temp. (°C.) | Vacuum mm/Hg. Pressure |
| --- | --- | --- | --- |
| 1 | 55/118 | 129/130 | 2.79/2.77 |
| 2 | 120 | 131 | 2.74 |
| 3 | 120 | 132 | 2.73 |
| 4 | 120 | 133 | 2.70 |
| 5 | 120 | 133 | 2.69 |
| 6 | 121 | 133 | 2.69 |
| 7 | 120 | 133 | 2.69 |
| 8 | 120 | 134 | 2.67 |
| 9 | 121 | 134 | 2.66 |
| 10 | 120 | 135 | 2.66 |

-continued

| Fraction No. | Vapor Temp. (°C.) | Liquid Temp. (°C.) | Vacuum mm/Hg. Pressure |
| --- | --- | --- | --- |
| 11 | 120 | 135 | 2.66 |
| 12 | 121 | 136 | 2.64 |
| 13 | 120 | 136 | 2.63 |
| 14 | 122 | 137 | 2.63 |
| 15 | 122 | 138 | 2.63 |
| 16 | 122 | 145 | 2.63 |
| 17 | 122 | 145 | 2.63 |
| 18 | 122 | 148 | 2.61 |
| 19 | 122 | 156 | 2.61 |
| 20 | 115 | 200 | 2.60. |

Bulked fractions 9-17 have a cassis, camphoraceous, sweaty, borneol aroma with parsely, basil, cassis, sweaty, borneol like, camphoraceous and eucalyptus bud-like topnotes.

FIG. 10 is the GLC profile of the reaction product (Conditions: Carbowax column programmed at 220° C. isothermal). The peaks indicated by reference numerals 102, 104, 106 and 100 are the peaks for the compounds having the structures:

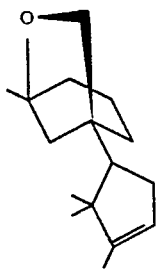

and

and their isomers.

EXAMPLE VI

PREPARATION OF METHYL CAMPHOLENYL SPIROCYCLOOXAOCTANE

Reaction:

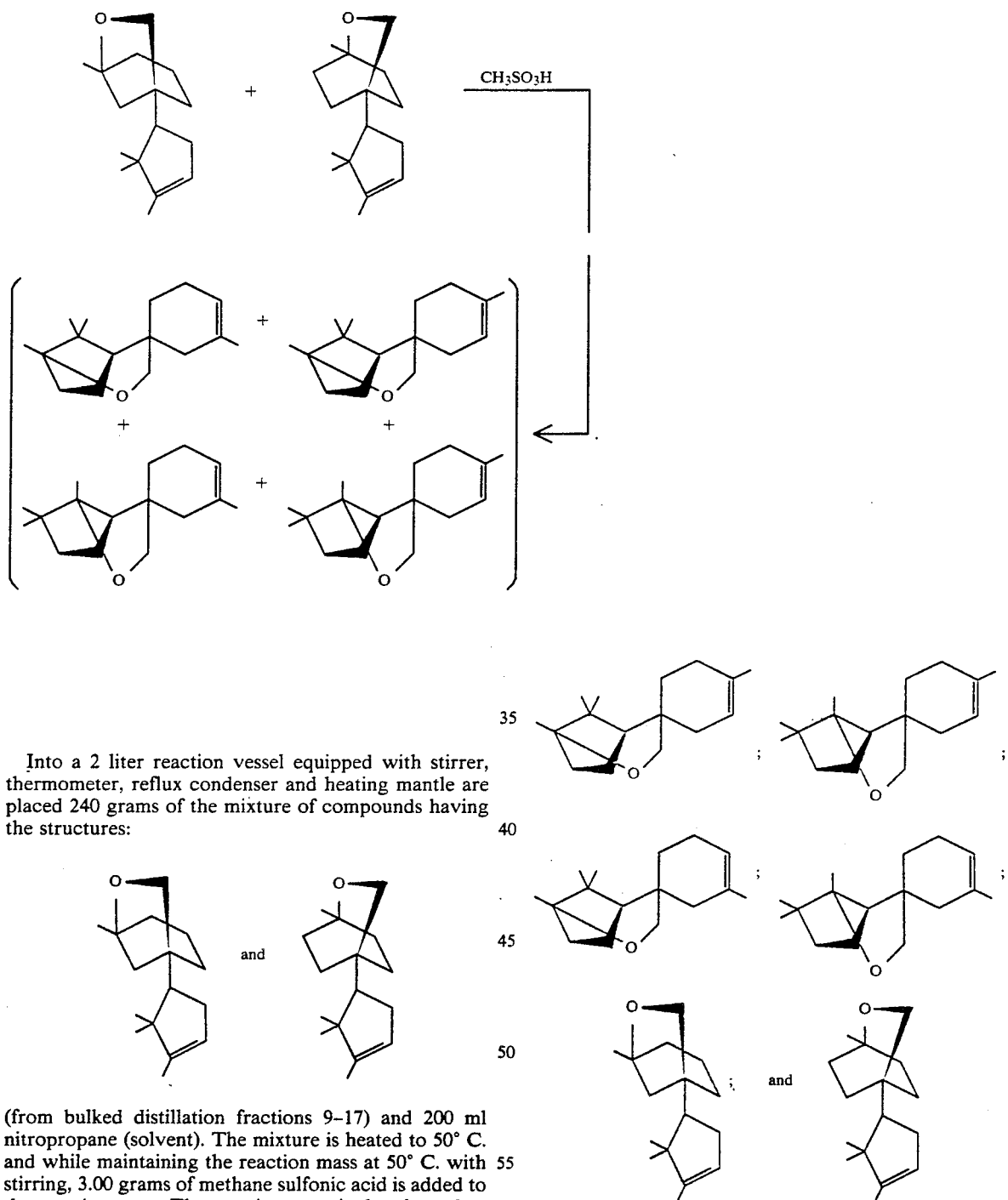

Into a 2 liter reaction vessel equipped with stirrer, thermometer, reflux condenser and heating mantle are placed 240 grams of the mixture of compounds having the structures:

(from bulked distillation fractions 9–17) and 200 ml nitropropane (solvent). The mixture is heated to 50° C. and while maintaining the reaction mass at 50° C. with stirring, 3.00 grams of methane sulfonic acid is added to the reaction mass. The reaction mass is then heated to 60° C. and maintained at 60° C. for a period of 15 hours.

The reaction mass is then neutralized with a 10% aqueous solution of sodium bicarbonate 250 ml).

The organic phase is separated from the aqueous phase and the aqueous phase is extracted with toluene. The toluene extract and the organic phase are combined and washed with 600 ml saturated sodium chloride. The resulting product is then filtered through anhydrous magnesium sulfate and fractionally distilled to yield 100 grams of product containing the compounds having the structures:

with the percentage of compounds having the structures:

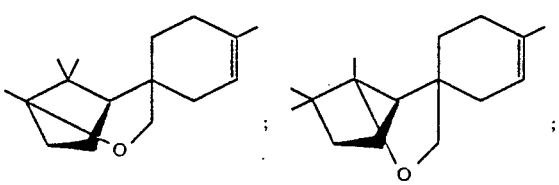

-continued

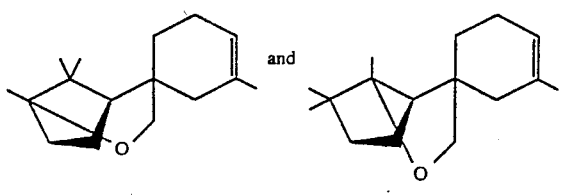

being 95% and the percentage of compounds having the structures:

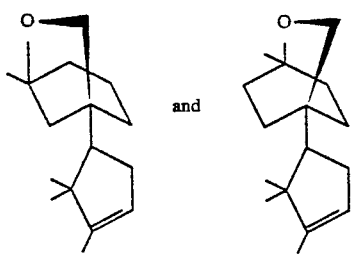

being 5% of the mixture. The resulting product has an intense cassis and balsamic aroma with fruity topnotes.

EXAMPLE VII

PREPARATION OF FORMYL CYCLOPENTENYL CYCLOHEXENE

Reaction:

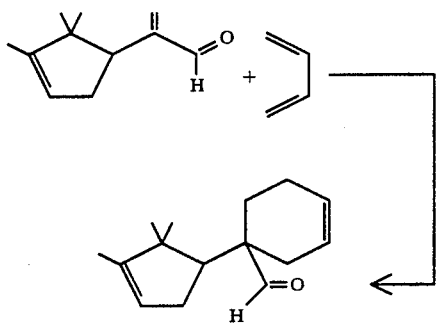

Into a 2 liter Parr Bomb is charged 692 grams of the compound having the structure:

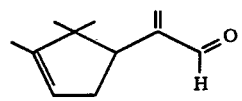

prepared according to Example I and 336 grams of butadien-1,3.

The Parr Bomb is closed and the temperature is raised to 150° C. and the pressure is raised to 270 psig. The Parr Bomb is maintained at 150°–155° C. and 270 psig for a period of 12 hours. The Parr Bomb is then cooled and opened and the resulting product is fractionally distilled on a fractional distillation column yielding the following fractions:

| Fraction No. | Vapor Temp. (°C.) | Liquid Temp. (°C.) | Vacuum mm/Hg. Pressure |
|---|---|---|---|
| 1 | 22/54 | 51/91 | 5.04/3.44 |
| 2 | 63 | 96 | 2.80 |
| 3 | 73 | 105 | 2.77 |
| 4 | 85 | 110 | 2.77 |
| 5 | 93 | 120 | 2.77 |
| 6 | 105 | 125 | 2.76 |
| 7 | 111 | 130 | 2.76 |
| 8 | 114 | 132 | 2.76 |
| 9 | 117 | 135 | 2.77 |
| 10 | 120 | 140 | 2.77 |
| 11 | 120 | 152 | 2.76 |
| 12 | 120 | 175 | 2.76 |
| 13 | 122 | 210 | 2.76. |

465 Grams (2.13 moles) of product are recovered having the structure:

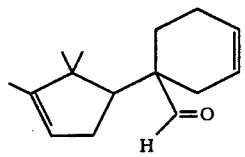

Fractions 7–13 are bulked for further reaction.

FIG. 13 is the GLC profile for the crude reaction product prior to distillation. The peak indicated by reference numeral 132 is the peak for the starting material having the structure:

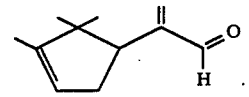

The peak indicated by reference numeral 130 is the peak for the desired product having the structure:

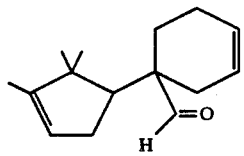

FIG. 14 is the NMR spectrum for the compound having the structure:

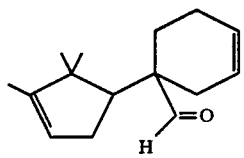

FIG. 15 is the infra-red spectrum for the compound having the structure:

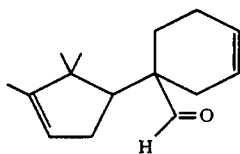

EXAMPLE VIII

PREPARATION OF CYCLOPENTENYL HYDROXYMETHYL CYCLOHEXENE DERIVATIVE

Reaction:

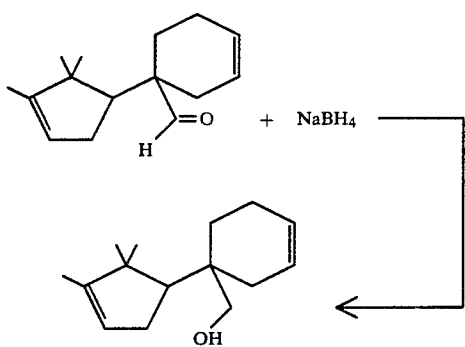

Into a 3 liter reaction flask equipped with stirrer, thermometer, reflux condenser, heating mantle and addition funnel are placed 47 grams (1.24 moles) of sodium borohydride, 200 ml isopropyl alcohol and 400 ml water. The reaction mass is heated to 28° C. and while maintaining the reaction mass at 28° C., over a 2 hour period, 555 grams of the compound having the structure:

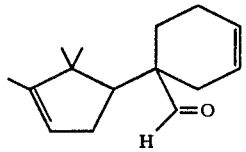

prepared according to Example VII is added to the reaction mass. The reaction mass is then heated to 46°–48° C. and while maintaining the reaction mass at 46°–48° C. the reaction mass is stirred with no further addition of product.

The reaction mass now exists in two phases; an organic phase and an aqueous phase. The organic phase is separated from the aqueous phase and washed with 500 ml saturated sodium chloride and then filtered through anhydrous magnesium sulfate.

The resulting product is distilled at atmospheric pressure and 200° C. to recover the isopropyl alcohol.

The reaction mass is then distilled at 15 mm/Hg. and 170° C. to recover "light" fractions.

The resulting product (465 grams) has 98% purity and is the compound having the structure:

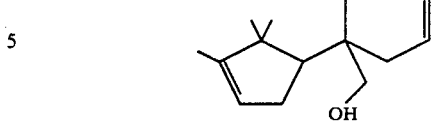

FIG. 15 is the GLC profile of the reaction product prior to distillation. The peak indicated by reference numeral 150 is the peak for the compound having the structure:

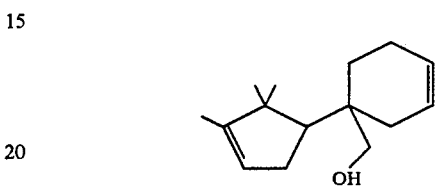

FIG. 16 is the NMR spectrum for the compound having the structure:

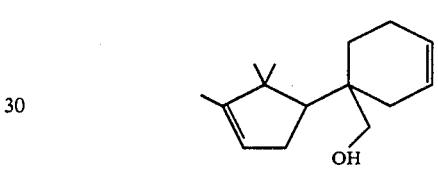

EXAMPLE IX

PREPARATION OF CAMPHOLENYL SPIROCYCLOOXAOCTANE

Reaction:

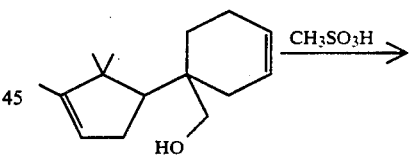

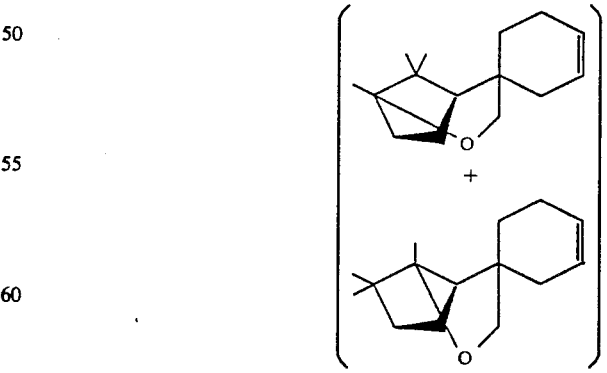

Into a 3 liter reaction vessel equipped with stirrer, thermometer, reflux condenser and heating mantle are placed 465 grams of the compound having the structure:

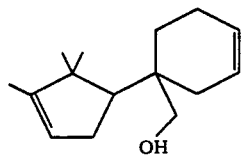

prepared according to Example VIII and 400 ml of mitromethane. The reaction mass is heated to 40° C.

While maintaining the reaction mass at 40° C., 5.95 grams (0.062 moles) of methane sulfonic acid is added to the reaction mass.

The reaction mass is heated to 50° C. and maintained at 50° C. for a period of 2 hours. The reaction mass is then heated to 60° C. and maintained at 60° C. for a period of 10 hours. At the end of the 10 hour period, the reaction mass is cooled to room temperature and 10% aqueous sodium bicarbonate 250 ml) is added to the reaction mass. The reaction mass now exists in two phases. The organic phase is separated from the aqueous phase. The aqueous phase is washed with toluene (400 ml) and the toluene extract is combined with the organic phase. The resulting product is then washed with 600 ml saturated sodium chloride and filtered through anhydrous magnesium sulfate. The resulting product is then fractionally distilled to yield the following fractions:

| Fraction No. | Vapor Temp. (°C.) | Liquid Temp. (°C.) | Vacuum mm/Hg. Pressure |
|---|---|---|---|
| 1 | 40/44 | 45/86 | 100/2.91 |
| 2 | 111 | 129 | 2.85 |
| 3 | 112 | 131 | 2.84 |
| 4 | 113 | 133 | 2.84 |
| 5 | 115 | 137 | 2.82 |
| 6 | 115 | 140 | 2.82 |
| 7 | 117 | 158 | 2.80 |
| 8 | 125 | 183 | 2.77 |
| 9 | 110 | 200 | 2.18. |

Distillation fractions 3–6 are bulked. Bulked distillation fractions 3–6 have a cassis, Black currant, piney and balsamic aroma, with animalic, piney, fruity, camphoraceous, woody, peppery and balsamic topnotes.

FIG. 17 is the GLC profile for the reaction product prior to distillation. The peaks indicated by reference numerals 172 and 174 are peaks for the compounds having the structures:

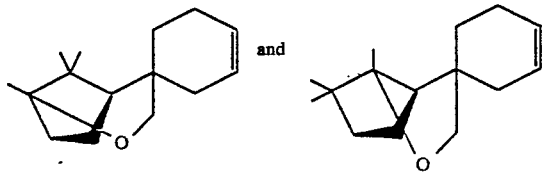

FIG. 18 is the NMR spectrum for the peak indicated by reference numeral 174 of FIG. 17, for one or both of the compounds having the structures:

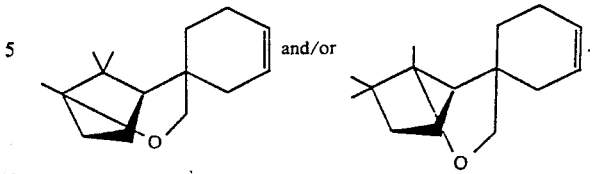

FIG. 19 is the infra-red spectrum for the peak indicated by reference numeral 174 of FIG. 17, for one or both of the compounds having the structures:

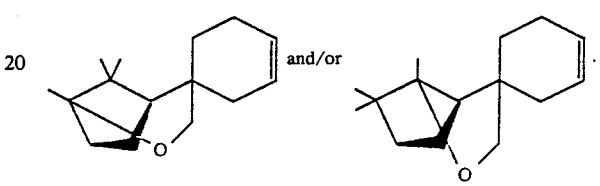

FIG. 20 is the NMR spectrum for the peak indicated by reference numeral 172 of FIG. 17, for one or both of the compounds having the structures:

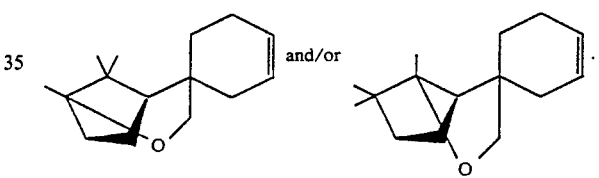

FIG. 21 is the infra-red spectrum for the peak indicated by reference numeral 172 of FIG. 17, for one or both of the compounds having the structures:

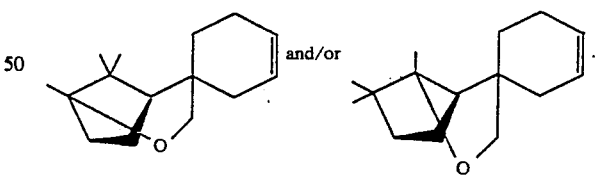

EXAMPLE X

PREPARATION OF
3,4-DIMETHYL-1-(2,2,3-TRIMETHYL)-3-CYCLO-PENTEN-1-YL-3-CYCLOHEXENE-1-CARBOX-ALDEHYDE

Reaction:

-continued

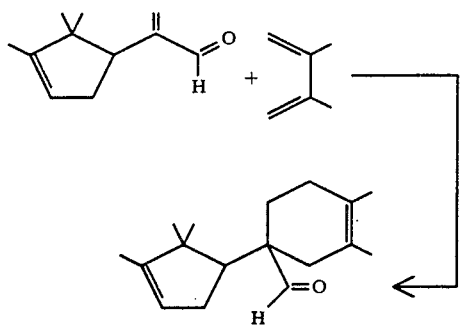

Into a 2 liter Parr Bomb is charged 769 grams of the compound having the structure:

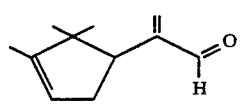

prepared according to Example I and 451 grams (5.39 moles) of 2,3-dimethyl-1,3-butadiene.

The Parr Bomb is closed and the temperature is raised to 186° C. and the pressure is raised to 70 psig. The Parr Bomb temperature is then allowed to drop to 150° C. over a period of 3 hours and is then maintained at 155°-180° C. for a period of 3 hours; and is then maintained at 175° C. for a period of 9 hours.

The reaction mass is then cooled to room temperature and the Parr Bomb is opened. The reaction mass is filtered and distilled yielding the following fractions:

| Fraction No. | Vapor Temp. (°C.) | Liquid Temp. (°C.) | Vacuum mm/Hg. Pressure |
|---|---|---|---|
| 1 | 29/65 | 94/115 | 3.36/3.20 |
| 2 | 90 | 132 | 2.33 |
| 3 | 112 | 138 | 2.59 |
| 4 | 124 | 142 | 2.80 |
| 5 | 130 | 143 | 2.41 |
| 6 | 130 | 145 | 2.43 |
| 7 | 128 | 142 | 2.02 |
| 8 | 128 | 145 | 2.00 |
| 9 | 133 | 148 | 2.40 |
| 10 | 133 | 149 | 2.40 |
| 11 | 133 | 145 | 2.40 |
| 12 | 133 | 145 | 2.39 |
| 13 | 131 | 142 | 2.39 |
| 14 | 131 | 142 | 2.38 |
| 15 | 131 | 145 | 2.37 |
| 16 | 180 | 110 | 2.34. |

Fractions 5-16 are bulked for the next reaction.

FIG. 22 is the GLC profile for the reaction product containing the compound having the structure:

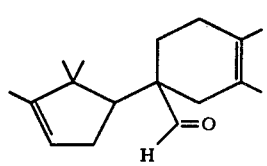

The peak indicated by reference numeral 2200 is the peak for the compound having the structure:

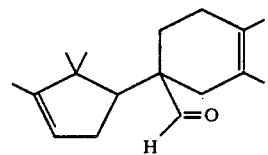

FIG. 23 is the NMR spectrum for the compound having the structure:

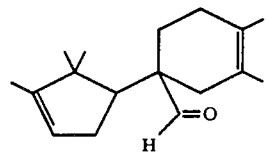

FIG. 24 is the infra-red spectrum for the compound having the structure:

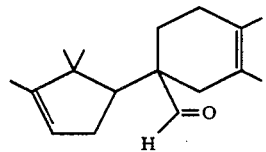

EXAMPLE XI

PREPARATION OF 3,4-DIMETHYL-1-(2,2,3-TRIMETHYL-3-CYCLO-PENTEN-1-YL)-3-CYCLOHEXENE-1-METHANOL

Reaction:

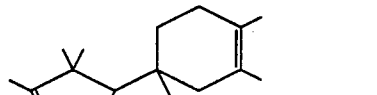

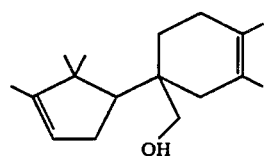

Into a 3 liter reaction flask equipped with stirrer, thermometer, reflux condenser, heating mantle and addition funnel are placed 63 grams (1.66 moles) of sodium borohydride, 700 ml water and 500 ml isopropyl alcohol. The reaction mass, while being maintained at 21°-22° C. is admixed with a mixture of 200 ml isopropyl alcohol and 679 grams of the compound having the structure:

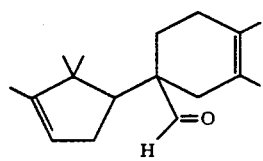

(addition taking place over a 1.5 hour period).

The reaction mass is then heated to 40° C. and maintained at 32°–40° C. for a period of 2 hours with stirring.

At the end of the reaction the reaction mass exists in two phases; an organic phase and an aqueous phase. The organic phase is washed with 500 ml saturated sodium chloride. The resulting organic phase is then filtered through anhydrous magnesium sulfate and concentrated to yield 658 grams of product (96% yield) containing the compound having the structure:

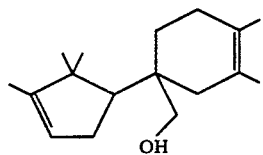

FIG. 25 is the GLC profile for the resulting product. The peak indicated by reference numeral 2500 is the peak for the compound having the structure:

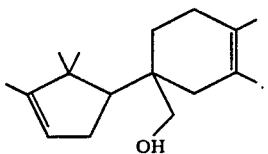

FIG. 26 is the NMR spectrum for the compound having the structure:

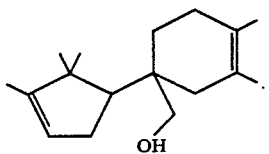

FIG. 27 is the infra-red spectrum for the compound having the structure:

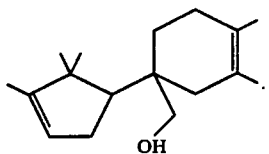

EXAMPLE XII

PREPARATION OF CAMPHOLENYL DIMETHYL SPIROBICYCLOOXAOCTANE

Reaction:

-continued

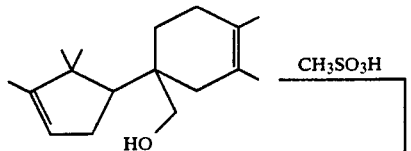

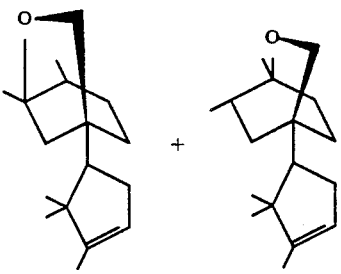

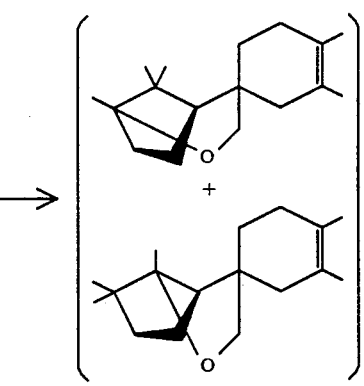

Into a 5 liter reaction vessel equipped with stirrer, thermometer, reflux condenser, heating mantle and addition funnel are placed 113 grams (2.47 moles) of the compound having the structure.

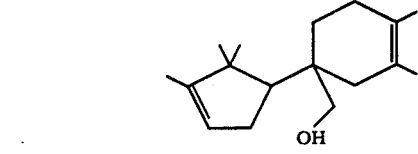

prepared according to Example XI and 600 ml nitroethane. The reaction mass is heated to 40° C. and while maintained at 40° C., 7.12 grams (0.074 moles) of methane sulfonic acid is added to the reaction mass. The reaction mass with stirring is heated to 70° C. and maintained at 70° C. for a period of 3 hours.

At the end of the 3 hour period, the reaction mass is cooled to room temperature and 300 ml of a 10% aqueous sodium bicarbonate solution is added to the reaction mass.

The organic phase is separated from the aqueous phase and the organic phase is washed with 500 ml saturated sodium chloride.

The resulting organic phase is then filtered over anhydrous magnesium sulfate and then fractionally distilled yielding the following fractions:

| Fraction No. | Vapor Temp. (°C.) | Liquid Temp. (°C.) | Vacuum mm/Hg. Pressure |
|---|---|---|---|
| 1 | 39/30 | 53/91 | 11.5/2.9 |
| 2 | 127 | 145 | 2.3 |
| 3 | 122 | 143 | 1.5 |
| 4 | 125 | 141 | 1.6 |
| 5 | 125 | 140 | 1.6 |
| 6 | 126 | 140 | 1.6 |
| 7 | 125 | 140 | 1.56 |
| 8 | 120 | 138 | 1.55 |
| 9 | 120 | 139 | 1.55 |
| 10 | 120 | 141 | 1.55 |
| 11 | 120 | 147 | 1.29 |
| 12 | 102 | 200 | 0.655. |

Fractions 3-10 are bulked. Bulked distillation fractions 3-10 contains a mixture containing 95% by weight of the compounds having the structures:

 and 

and 5% by weight of a mixture of compounds having the structures:

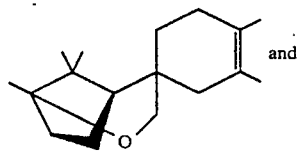 and 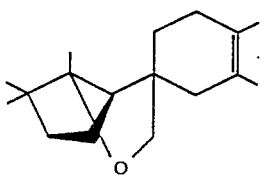

The resulting mixture has a cassis, animalic, camphoraceous, woody and peppery aroma, with cassis and terpenic topnotes.

FIG. 28 is the GLC profile for the reaction product prior to distillation. The peak indicated by reference numeral 2800 is the peak for the mixture of compounds having the structures:

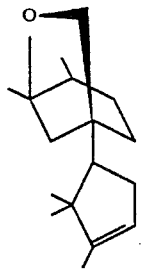 and 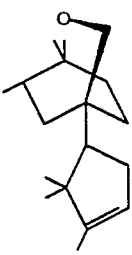

The peak indicated by reference numeral 2802 is the peak for the mixture of compounds having the structures:

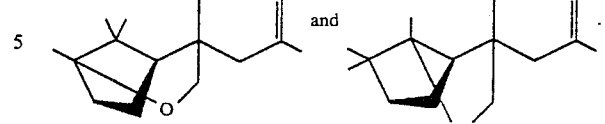

FIG. 29 is the NMR spectrum for the peak indicated by reference numeral 2802 of FIG. 28 for one or both of the compounds having the structures:

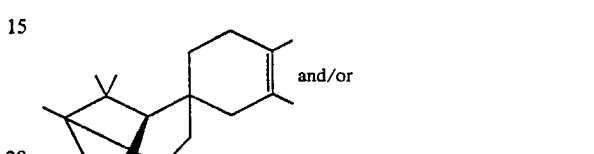

FIG. 30 is the infra-red spectrum for the peak indicated by reference numeral 2802 for one or both of the compounds having the structures:

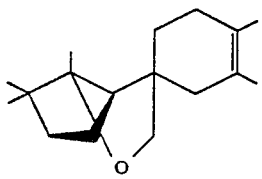

and/or

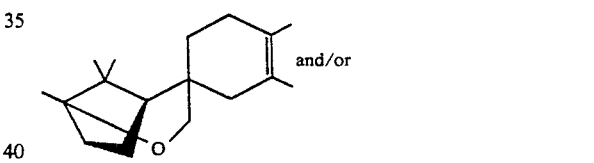

FIG. 31 is the NMR spectrum for the peak indicated by reference numeral 2800 of FIG. 28 for the mixture of compounds having the structures:

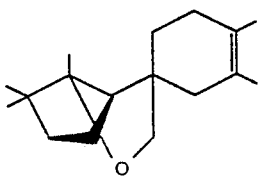

FIG. 32 is the infra-red spectrum for the peak indicated by reference numeral 2800 of FIG. 28 for the mixture of compounds having the structures:

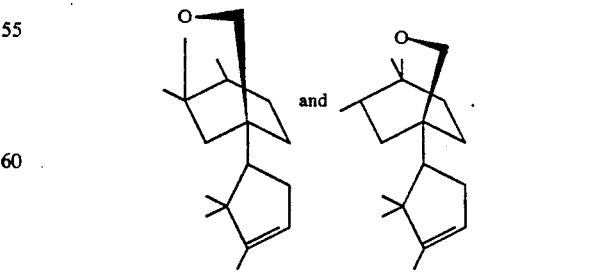

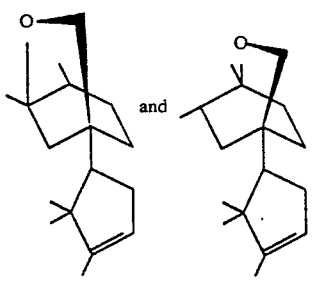

EXAMPLE XIII

The camphonyl spirocyclooxactane-containing compositions of our invention produced according to Examples VI, IX and XII inclusive have very long lasting cassis, Black currant, piney, balsamic, animalic, camphoraceous, woody and pepper aromas, with animalic, piney, fruity, camphoraceous, woody, peppery, balsamic, terpenic and cassis topnotes. These aroma nuances may be utilized to a great extent in inexpensive functional products. The following pine fragrance demonstrates the use of these materials in perfume compositions:

| Ingredients | Parts by Weight | | |
|---|---|---|---|
| | Example XIII(A) | Example XIII(B) | Example XIII(C) |
| Isobornyl acetate | 100 | 100 | 100 |
| Camphor | 10 | 10 | 10 |
| Terpineol | 25 | 25 | 25 |
| Fir Balsam Absolute (50% in Diethyl Phthalate) | 20 | 20 | 20 |
| Coumarin | 4 | 4 | 4 |
| Linalool | 30 | 30 | 30 |
| Anethol | 2 | 2 | 2 |
| Fenchyl Alcohol | 10 | 10 | 10 |
| Lemon Terpenes Washed | 50 | 50 | 50 |
| Borneol | 5 | 5 | 5 |
| Galbanum Oil | 5 | 5 | 5 |
| Turpentine Russian | 150 | 150 | 150 |
| Pinus Pumilionus | 50 | 50 | 50 |
| Eucalyptol | 50 | 50 | 50 |
| 2,2,6-trimethyl-1-cyclohexene-1-carboxaldehyde | 5 | 5 | 5 |
| Maltol (1% in Diethyl Phthalate) | 5 | 5 | 5 |
| Mixture of compounds having the structures: 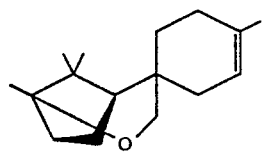 and 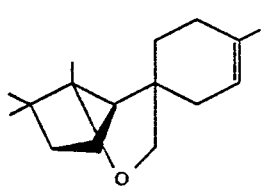 | 12 | 0 | 0 |
| 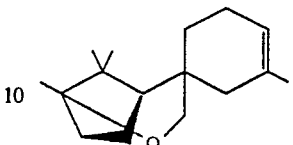 and 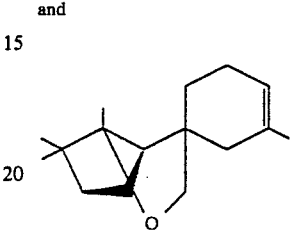 prepared according to Example VI. Mixture of compounds having the structures: 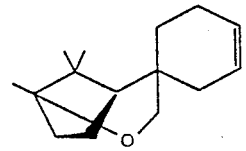 and 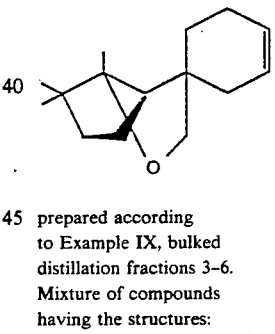 prepared according to Example IX, bulked distillation fractions 3–6. Mixture of compounds having the structures: 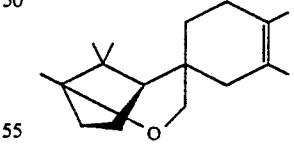 and 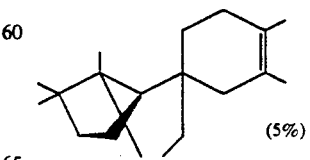 (5%) and | 0 | 12 | 0 |
| | 0 | 0 | 12 |

-continued

| | Parts by Weight | | |
|---|---|---|---|
| Ingredients | Example XIII(A) | Example XIII(B) | Example XIII(C) |

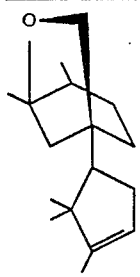

and

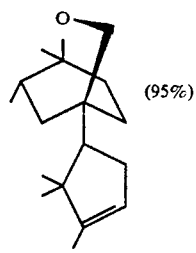 (95%)

prepared according to
Example XII, bulked
distillation fractions 3-10.

The mixture of compounds having the structure:

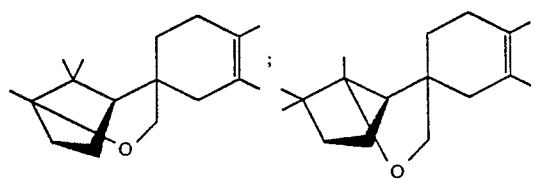

prepared according to Example VI adds to this pine fragrance cassis and balsamic undertones, with animalic topnotes. Accordingly, the fragrance of Example XIII(A) can be described as "piney, with cassis and balsamic undertones and animalic topnotes".

The mixture of compounds having the structures:

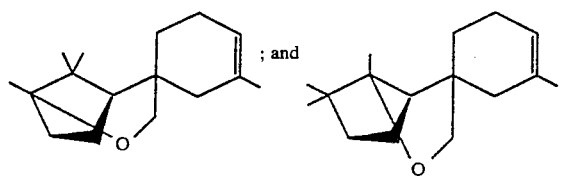

prepared according to Example IX (bulked distillation fractions 3-6) adds to this piney fragrance, cassis, Black currant, and balsamic undertones, and animalic, fruity, camphoraceous, woody, peppery and balsamic topnotes. Accordingly, the fragrance of Example XIII(B) can be described as "piney, with cassis, Black currant and balsamic undertones and animalic, fruity, camphoraceous, woody, peppery and balsamic topnotes".

The mixture of compounds having the structures:

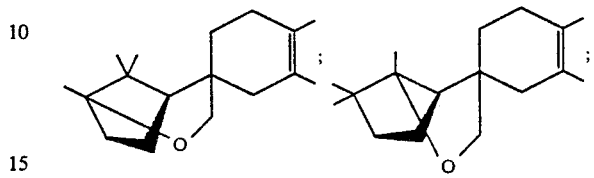

prepared according to Example XII, bulked distillation fractions 3-10 adds to this pine fragrance cassis, animalic, camphoraceous, woody and peppery undertones, with cassis and terpenic topnotes. Accordingly, the fragrance of Example XIII(C) can be described as "piney, with cassis, animalic, camphoraceous, woody and peppery undertones, with cassis and terpenic topnotes".

EXAMPLE XIV

COSMETIC POWDER PREPARATION

A cosmetic powder is prepared by mixing in a ball mill 100 grams of talcum powder with 0.25 grams of one of the substances set forth in Table III below containing at least one of the camphonyl spirocyclooxaoctane-containing compositions of our invention. Each of the cosmetic powders has an excellent aroma as described in Table III below.

TABLE III

| Perfumery Substance | Aroma Nuance |
|---|---|
| Mixture of compounds having the structures: 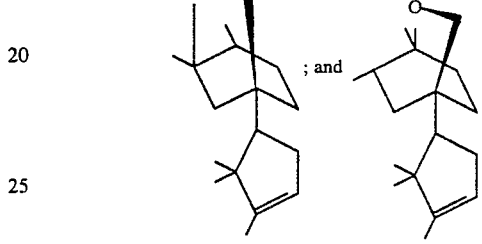 | A cassis and balsamic aroma with animalic undertones. |

TABLE III-continued

| Perfumery Substance | Aroma Nuance |
|---|---|
| 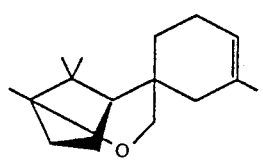<br>and<br>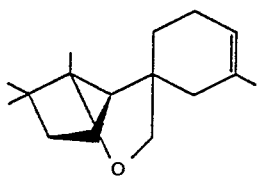<br>prepared according to Example VI. | |
| Mixtures of compounds having the structures:<br>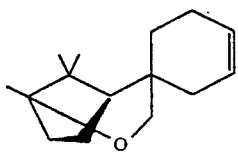<br>and<br>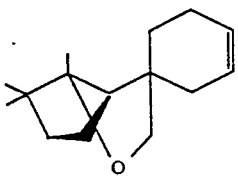<br>prepared according to Example IX, bulked distillation fractions 3–6. | A cassis, Black currant, piney and balsamic aroma, with animalic, piney, fruity, camphoraceous, woody, peppery and balsamic topnotes. |
| Mixture of compounds having the structures:<br>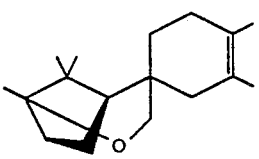<br>and<br>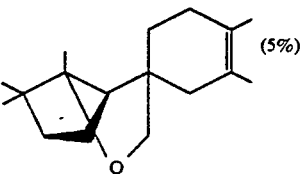 (5%)<br>and | A cassis, animalic, camphoraceous, woody and peppery aroma, with cassis and terpenic topnotes. |

TABLE III-continued

| Perfumery Substance | Aroma Nuance |
|---|---|
| 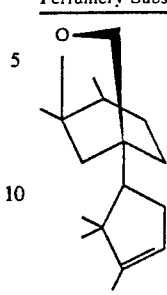<br>and<br>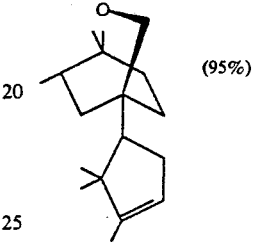 (95%)<br>prepared according to Example XII, bulked distillation fractions 3–10. | |
| Perfume composition of Example XIII(A). | Piney, with cassis and balsamic undertones and animalic topnotes |
| Perfume composition of Example XIII(B). | Piney, with cassis, Black currant and balsamic undertones and animalic, fruity, camphoraceous, woody, peppery and balsamic topnotes. |
| Perfume composition of Example XIII(C). | Piney, with cassis, animalic, camphoraceous, woody and peppery undertones, with cassis and terpenic topnotes. |

EXAMPLE XV

PERFUMED LIQUID DETERGENT

Concentrated liquid detergents (Lysine salt of n-dodecylbenzene sulfonic acid as more specifically described in U.S. Pat. No. 3,948,818 issued on Apr. 6, 1976, the specification for which is incorporated herein) with aromas with set forth in Table III of Example XIV, supra are prepared containing 0.10%, 0.15, 0.02%, 0.25%, 0.30% and 0.35% of each of the substances of Table III of Example XIV. They are prepared by adding and homogeneously admixing the appropriate quantity of one of the substances of Table III of Example XIV in the liquid detergent. The detergents all possess excellent aromas as set forth in Table III of Example XIV.

EXAMPLE XVI

PREPARATION OF A COLOGNE AND HANDKERCHIEF PERFUME

The substances set forth in Table III of Example XIV are incorporated separately into colognes at concentrations of 2.0%, 2.5%, 3.0%, 3.5%, 4.0%, 4.5% and 5.0% in 75%, 80%, 85% and 90% aqueous food grade ethanol solutions; and into handkerchief perfumes at concentrations of 15%, 20%, 25% and 30%, in 80%, 85%, 90% and 95% aqueous food grade ethanol solutions. Distinctive aromas as set forth in Table III of Example XIV, supra are imparted to the colognes and to the handkerchief perfume compositions at all levels indicated.

EXAMPLE XVII

PREPARATION OF SOAP COMPOSITION

One hundred grams of soap chips (IVORY ®, produced by the Procter & Gamble Company, of Cincinnati, Ohio) are admixed with 1 gram of each of the substances of Table III of Example XIV, supra until homogeneous compositions are obtained. The homogeneous compositions are each separated then heated under 3 atmospheres pressure at 180° C. for a period of 3 hours and the resulting liquid samples are place in soap molds. The resulting soap cake, on cooling, manifest excellent long-lasting aromas as set forth in Table III of Example XIV, supra.

EXAMPLE XVIII

PREPARATION OF SOLID DETERGENT COMPOSITIONS

Detergents are prepared from the following ingredients according to Example II of Canadian Pat. No. 1,007,948 the specification for which is incorporated by reference herein:

| Ingredients | Parts by Weight |
| --- | --- |
| Neodol ® 45-11 (a $C_{14}$—$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a phosphate-free detergent. A total of 100 grams of said detergent is admixed separately with 0.10, 0.15, 0.20 and 0.25 grams of each of the substances of Table III of Example XIV. Each of the detergent samples has an excellent aromas as set forth in Table III of Example XIV.

EXAMPLE XIX

DRYER-ADDED FABRIC SOFTENER ARTICLE

Utilizing the procedure of Example II at column 15 of U.S. Pat. No. 3,623,396, the specification for which is incorporated by reference herein, a non-woven cloth substrate useful as a dryer-added fabric softening article of manufacture is prepared wherein the substrate, the substrate coating and the outer coating and the perfuming material are as follows:
1. A water "dissolvable" paper ("Dissolvo Paper")
2. Adogen 448 (m.p. about 140° F.) as the substrate coating; and
3. An outer coating have the following formulation (m.p. about 150° F.)
    57% $C_{20-22}$ HAPS
    22% isopropyl alcohol
    20% antistatic agent
    1% of one of the substances of Table III of Example XIV, supra.

Fabric softening compositions containing one of the substances of Table III of Example XIV consist essentially of a substrate having a weight of about 3 grams per 100 square inches of substrate coating having a weight of about 1.85 grams per 100 square inches; and an outer coating having a weight of about 1.4 grams per 100 square inches thereby providing a total aromatized substrate and outer coating weight ratio of about 1:1 by weight of the substrate.

Pleasant aromas as set forth in Table III of Example XIV are imparted to the head space in the dryer on operation thereof using the said drier-added fabric softening non-woven fabric.

What is claimed is:

1. A camphonyl spirocyclooxaoctane composition comprising at least one of the compounds defined according to a structure selected from the group consisting of:

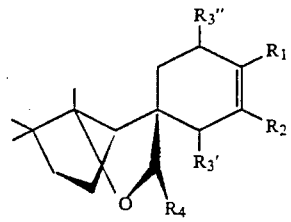

and

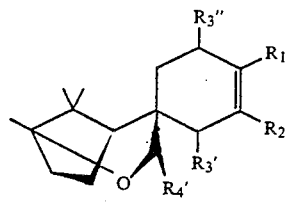

wherein $R_1$, $R_2$, $R_3'$ and $R_3''$ each represents hydrogen or methyl and $R_4'$ represents hydrogen or $C_1$–$C_5$ alkyl with the provisos:
   (i) at least one of $R_3'$ and $R_3''$ is hydrogen; and
   (ii) when $R_1$ or $R_2$ is methyl then each of $R_3'$ and $R_3''$ is hydrogen.

2. The composition of claim 1 having admixed therewith at least one cyclopentenyl oxabicyclooxaoctane defined according to a structure selected from the group consisting of:

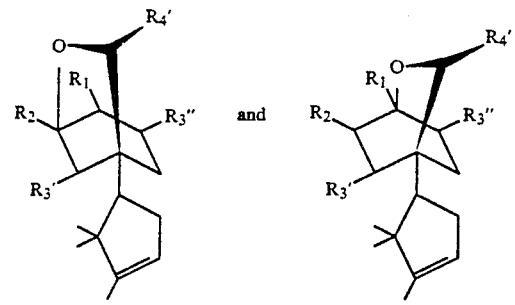

wherein $R_1$, $R_2$, $R_3'$ and $R_3''$ each represents hydrogen or methyl and $R_4'$ represents hydrogen or $C_1$–$C_5$ alkyl with the provisos:
   (i) one or two of $R_1$, $R_2$, $R_3'$ and $R_3''$ represents methyl;
   (ii) $R_1$ and/or $R_2$ each represents methyl;
   (iii) at least one or $R_3'$ and $R_3''$ is hydrogen; and (iv) when $R_1$ or $R_2$ methyl then each of $R_3'$ and $R_3''$ is hydrogen.

3. The composition of claim 1 which is the mixture of compounds having the structures:

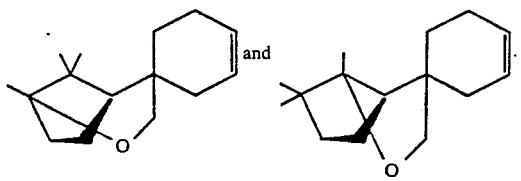

4. The composition of claim 2 containing a mixture of compounds having the structures:

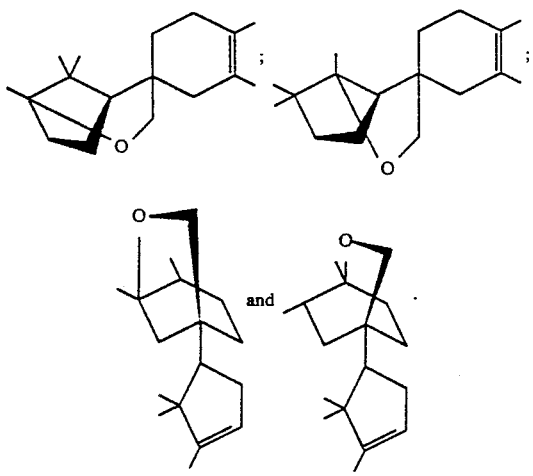

5. A perfume composition comprising a perfume base and intimately admixed therewith, an aroma imparting, augmenting or enhancing quantity of at least one of the compounds defined according to claim 1.

6. A perfume composition comprising a perfume base and intimately admixed therewith, an aroma imparting, augmenting or enhancing quantity of at least one of the compounds defined according to claim 2.

7. A perfumed article comprising a perfume article base and intimately admixed therewith, an aroma imparting, augmenting or enhancing quantity of at least one of the compositions of matter defined according to claim 1.

8. A perfumed article comprising a perfume article base and intimately admixed therewith, an aroma imparting, augmenting or enhancing quantity of at least one of the compositions of matter defined according to claim 2.

9. A perfumed polymer comprising a microporous polymer and intimately admixed therewith, an aroma augmenting, imparting or enhancing quantity of at least one composition of matter defined according to claim 1.

10. A perfumed polymer comprising a microporous polymer and intimately admixed therewith, an aroma augmenting, imparting or enhancing quantity of at least one composition of matter defined according to claim 2.

11. A process for augmenting or enhancing the aroma of a consumable material selected from the group consisting of perfume compositions, colognes and perfumed articles comprising the step of intimately admixing with a perfume composition, a cologne or a perfume article, an aroma imparting, augmenting or enhancing quantity of at least one composition of matter defined according to claim 1.

12. A process for augmenting or enhancing the aroma of a consumable material selected from the group consisting of perfume compositions, colognes and perfumed articles comprising the step of intimately admixing with a perfume composition, a cologne or a perfumed article, an aroma imparting, augmenting or enhancing quantity of at least one composition of matter defined according to claim 2.

13. A process for augmenting or enhancing the aroma of a consumable material selected from the group consisting of perfume compositions, colognes and perfumed articles comprising the step of intimately admixing with a perfume composition, a cologne or a perfumed article, an aroma imparting, augmenting or enhancing quantity of at least one composition of matter defined according to claim 4.

14. A process for augmenting or enhancing the aroma of a consumable material selected from the group consisting of perfume compositions, colognes and perfume articles comprising the step of intimately admixing with a perfume composition, a cologne or a perfume article, an aroma imparting, augmenting or enhancing quantity of at least one composition of matter defined according to claim 5.

15. A process for preparing a composition of matter defined according to a structure selected from the group consisting of:

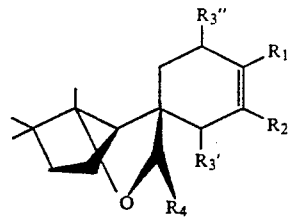

and

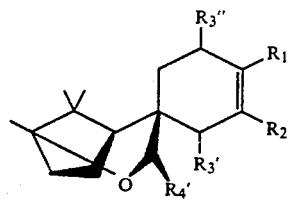

comprising the steps of:

(i) carrying out the reaction:

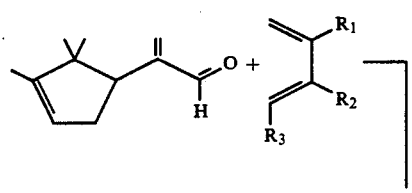

-continued

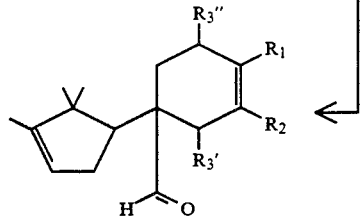

in the presence of a Lewis acid catalyst at −10° C. up to 30° C. or in the absence of a catalyst at a temperature less than 200° C.;

(ii) then carrying out in the alternative the reaction:

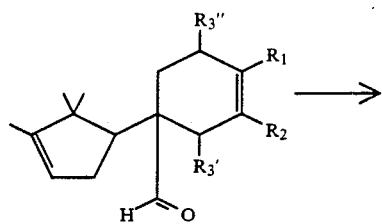

in the presence of an inert solvent and a hydride reducing agent or the reactions:

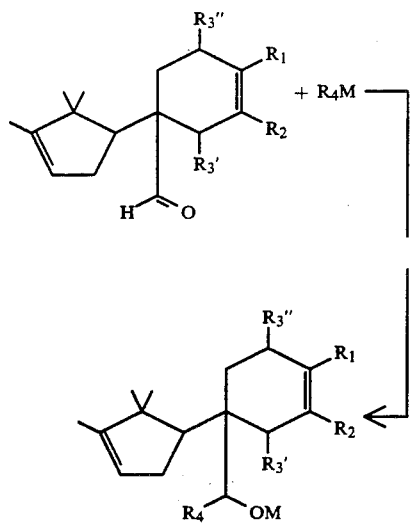

and

-continued

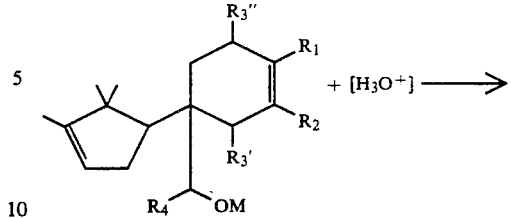

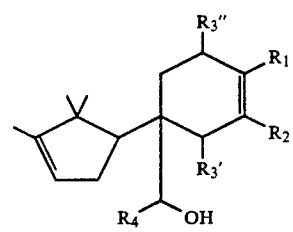

(iii) isolating the resulting alcohol by distillation;
(iv) then carrying out the reaction:

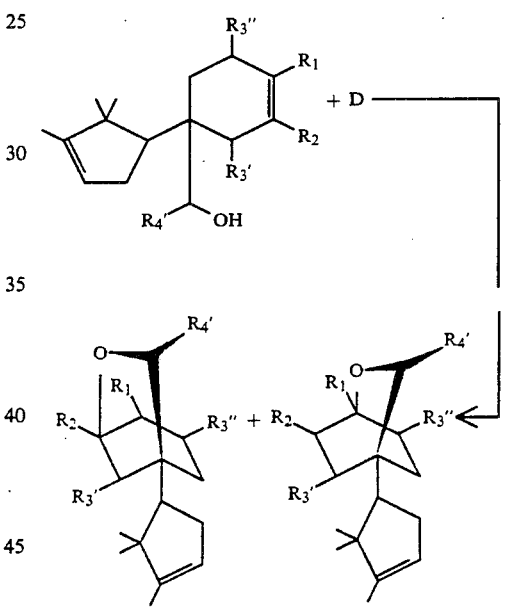

wherein D is a sulfonic acid cyclization reagent, at a temperature of from 25° C. up to 150° C. in the presence of a polar solvent or a Lewis acid catalyst for a time of from 2 up to 20 hours with a concentration of reactant having the structure:

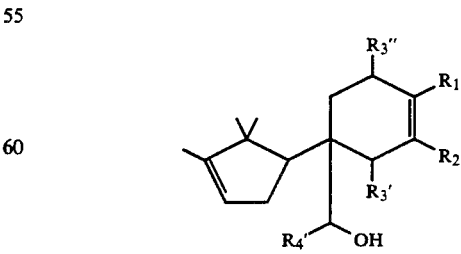

being from about 1 mole per liter up to about 6 moles per liter and thereafter or simultaneously carrying out the reaction:

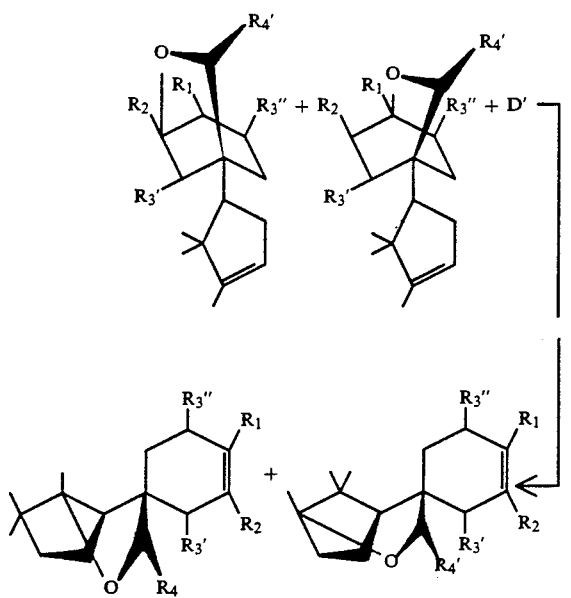

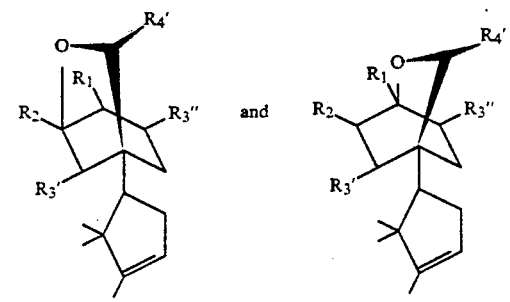

wherein D' is a sulfonic acid cyclization reagent at a temperature of 25°–150° C. over a time period of from 2–20 hours wherein $R_1$, $R_2$, $R_3'$ and $R_3''$ each represents hydrogen or methyl and $R_4$ is hydrogen or $C_1$–$C_5$ alkyl with the provisos:

(A) with regard to the components defined according to the structures:
(i) one or two of $R_1$, $R_2$, $R_3'$ and $R_3''$ represents methyl;
(ii) $R_1$ and/or $R_2$ are methyl;
(iii) at least one of $R_3'$ and $R_3''$ is hydrogen; and
(iv) when $R_1$ or $R_2$ is methyl then each of $R_3'$ and $R_3''$ is hydrogen; and (B) with regard to the compounds defined according to the structures:

(i) at least one of $R_3'$ and $R_3''$ is hydrogen; and
(ii) when $R_1$ and $R_2$ is methyl then each of $R_3'$ and $R_3''$ is hydrogen and M represents lithium, MgBr or MgCl; and $R_4$ represents $C_1$–$C_5$ alkyl.

* * * * *